US008232584B2

(12) United States Patent
Lieber et al.

(10) Patent No.: US 8,232,584 B2
(45) Date of Patent: Jul. 31, 2012

(54) NANOSCALE SENSORS

(75) Inventors: Charles M. Lieber, Lexington, MA (US); Fernando Patolsky, Rehovot (IL); Gengfeng Zheng, Dorchester, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 325 days.

(21) Appl. No.: 12/536,269

(22) Filed: Aug. 5, 2009

(65) Prior Publication Data

US 2010/0112546 A1    May 6, 2010

Related U.S. Application Data

(63) Continuation of application No. 11/501,466, filed on Aug. 9, 2006, now abandoned, which is a continuation-in-part of application No. 11/137,784, filed on May 25, 2005, now abandoned.

(60) Provisional application No. 60/707,136, filed on Aug. 9, 2005.

(51) Int. Cl.
*G01N 27/403* (2006.01)
*G01N 33/566* (2006.01)

(52) U.S. Cl. ........................................ 257/253; 436/501

(58) Field of Classification Search .................... None
See application file for complete search history.

(56) References Cited

U.S. PATENT DOCUMENTS

| 3,873,359 | A | 3/1975 | Lando |
|---|---|---|---|
| 3,873,360 | A | 3/1975 | Lando |
| 3,900,614 | A | 8/1975 | Lando |
| 4,673,474 | A | 6/1987 | Ogawa |
| 4,939,556 | A | 7/1990 | Eguchi et al. |
| 5,023,139 | A | 6/1991 | Birnboim et al. |
| 5,089,545 | A | 2/1992 | Pol |
| 5,252,835 | A | 10/1993 | Lieber et al. |
| 5,274,602 | A | 12/1993 | Glenn |
| 5,453,970 | A | 9/1995 | Rust et al. |
| 5,475,341 | A | 12/1995 | Reed |

(Continued)

FOREIGN PATENT DOCUMENTS

EP    1 087 413 A2    3/2001

(Continued)

OTHER PUBLICATIONS

Agarwal, R., et al., "Lasing in Single Cadmium Sulfide Nanowire Optical Cavities," *Nano Letters*, vol. 5, No. 5, pp. 917-920 (2005).

(Continued)

*Primary Examiner* — Samuel Woolwine
(74) *Attorney, Agent, or Firm* — Wolf, Greenfield & Sacks, P.C.

(57) ABSTRACT

Various aspects of the invention relate to nanoscale wire devices and methods of use for detecting analytes. In one aspect, the invention relates to a nanoscale electrical sensor array device, comprising at least one n-doped semiconductor nanoscale wire and at least one p-doped semiconductor nanoscale wire, each having a reaction entity immobilized thereon. Binding of an analyte to the immobilized reaction entity causes a detectable change in the electrical property of the nanoscale wire. In some embodiments, the reaction entity can be a nucleic acid that may interact with other nucleic acids, proteins, etc. In a specific embodiment, the nucleic acid may interact with an enzyme such as telomerase, which can extend the nucleic acid. In other embodiments, the analyte to be detected can be a toxin, virus or small molecule. Systems and methods of using such nanoscale devices are also disclosed, for example, within a microarray.

15 Claims, 36 Drawing Sheets

U.S. PATENT DOCUMENTS

| | | | |
|---|---|---|---|
| 5,512,131 A | 4/1996 | Kumar et al. |
| 5,537,075 A | 7/1996 | Miyazaki |
| 5,539,214 A | 7/1996 | Lynch et al. |
| 5,581,091 A | 12/1996 | Moskovits et al. |
| 5,589,692 A | 12/1996 | Reed |
| 5,607,876 A | 3/1997 | Biegelsen et al. |
| 5,620,850 A | 4/1997 | Bamdad et al. |
| 5,640,343 A | 6/1997 | Gallagher et al. |
| 5,726,524 A | 3/1998 | Debe |
| 5,739,057 A | 4/1998 | Tiwari et al. |
| 5,747,180 A | 5/1998 | Miller et al. |
| 5,751,156 A | 5/1998 | Muller et al. |
| 5,776,748 A | 7/1998 | Singhvi |
| 5,824,470 A | 10/1998 | Baldeschwieler et al. |
| 5,830,538 A | 11/1998 | Gates et al. |
| 5,840,435 A | 11/1998 | Lieber et al. |
| 5,847,565 A | 12/1998 | Narayanan |
| 5,858,862 A | 1/1999 | Westwater et al. |
| 5,864,823 A | 1/1999 | Levitan |
| 5,897,945 A | 4/1999 | Lieber et al. |
| 5,900,160 A | 5/1999 | Whitesides et al. |
| 5,903,010 A | 5/1999 | Flory et al. |
| 5,908,692 A | 6/1999 | Hamers et al. |
| 5,916,642 A | 6/1999 | Chang |
| 5,942,443 A | 8/1999 | Parce et al. |
| 5,997,832 A | 12/1999 | Lieber et al. |
| 6,036,774 A | 3/2000 | Lieber et al. |
| 6,038,060 A | 3/2000 | Crowley |
| 6,060,121 A | 5/2000 | Hidber et al. |
| 6,060,724 A | 5/2000 | Flory et al. |
| 6,069,380 A | 5/2000 | Chou et al. |
| 6,123,819 A | 9/2000 | Peeters |
| 6,128,214 A | 10/2000 | Kuekes et al. |
| 6,143,184 A | 11/2000 | Martin et al. |
| 6,149,819 A | 11/2000 | Martin et al. |
| 6,159,742 A | 12/2000 | Lieber et al. |
| 6,180,239 B1 | 1/2001 | Whitesides et al. |
| 6,187,165 B1 | 2/2001 | Chien et al. |
| 6,190,634 B1 | 2/2001 | Lieber et al. |
| 6,203,864 B1 | 3/2001 | Zhang et al. |
| 6,207,392 B1 | 3/2001 | Weiss et al. |
| 6,231,744 B1 | 5/2001 | Ying et al. |
| 6,256,767 B1 | 7/2001 | Kuekes et al. |
| 6,270,074 B1 | 8/2001 | Rasmussen et al. |
| 6,278,231 B1 | 8/2001 | Iwasaki et al. |
| 6,286,226 B1 | 9/2001 | Jin |
| 6,287,765 B1 | 9/2001 | Cubicciotti |
| 6,314,019 B1 | 11/2001 | Kuekes et al. |
| 6,325,904 B1 | 12/2001 | Peeters |
| 6,340,822 B1 | 1/2002 | Brown et al. |
| 6,346,189 B1 | 2/2002 | Dai et al. |
| 6,355,198 B1 | 3/2002 | Kim et al. |
| 6,359,288 B1 | 3/2002 | Ying et al. |
| 6,437,329 B1 | 8/2002 | Yedur et al. |
| 6,440,637 B1 | 8/2002 | Choi et al. |
| 6,451,113 B1 | 9/2002 | Givargizov |
| 6,459,095 B1 | 10/2002 | Heath et al. |
| 6,465,132 B1 | 10/2002 | Jin |
| 6,468,657 B1 | 10/2002 | Hou et al. |
| 6,503,375 B1 | 1/2003 | Maydan et al. |
| 6,528,020 B1 | 3/2003 | Dai et al. |
| 6,538,367 B1 | 3/2003 | Choi et al. |
| 6,559,468 B1 | 5/2003 | Kuekes et al. |
| 6,586,095 B2 | 7/2003 | Wang et al. |
| 6,628,053 B1 | 9/2003 | Den et al. |
| 6,716,409 B2 | 4/2004 | Hafner et al. |
| 6,741,019 B1 | 5/2004 | Filas et al. |
| 6,743,408 B2 | 6/2004 | Lieber et al. |
| 6,756,025 B2 | 6/2004 | Colbert et al. |
| 6,756,795 B2 | 6/2004 | Hunt et al. |
| 6,760,256 B2 | 7/2004 | Imamiya |
| 6,781,166 B2 | 8/2004 | Hunt et al. |
| 6,803,840 B2 | 10/2004 | Kowalcyk et al. |
| 6,808,746 B1 | 10/2004 | Dai et al. |
| 6,815,706 B2 | 11/2004 | Li et al. |
| 6,846,565 B2 | 1/2005 | Korgel et al. |
| 6,872,645 B2 | 3/2005 | Duan et al. |
| 6,882,051 B2 | 4/2005 | Majumdar et al. |
| 6,882,767 B2 | 4/2005 | Yang et al. |
| 6,902,720 B2 | 6/2005 | McGimpsey |
| 6,946,197 B2 | 9/2005 | Yadav et al. |
| 6,958,216 B2 | 10/2005 | Kelley et al. |
| 6,962,823 B2 | 11/2005 | Empedocles et al. |
| 6,974,706 B1 | 12/2005 | Melker et al. |
| 6,996,147 B2 | 2/2006 | Majumdar et al. |
| 7,048,903 B2 | 5/2006 | Colbert et al. |
| 7,129,554 B2 | 10/2006 | Lieber et al. |
| 7,254,151 B2 | 8/2007 | Lieber et al. |
| 7,256,466 B2 | 8/2007 | Lieber et al. |
| 7,301,199 B2 | 11/2007 | Lieber et al. |
| 7,303,875 B1 | 12/2007 | Bock et al. |
| 7,335,908 B2 | 2/2008 | Samuelson et al. |
| 7,399,691 B2 | 7/2008 | Lieber et al. |
| 2001/0054709 A1 | 12/2001 | Heath et al. |
| 2002/0013031 A1 | 1/2002 | Chen |
| 2002/0040805 A1 | 4/2002 | Swager |
| 2002/0055239 A1 | 5/2002 | Tuominen et al. |
| 2002/0084502 A1 | 7/2002 | Jang et al. |
| 2002/0086335 A1 | 7/2002 | Massey et al. |
| 2002/0112814 A1 | 8/2002 | Hafner et al. |
| 2002/0117659 A1 | 8/2002 | Lieber et al. |
| 2002/0122766 A1 | 9/2002 | Lieber et al. |
| 2002/0130311 A1 | 9/2002 | Lieber et al. |
| 2002/0130353 A1 | 9/2002 | Lieber et al. |
| 2002/0146714 A1 | 10/2002 | Lieber et al. |
| 2002/0158342 A1 | 10/2002 | Tuominen et al. |
| 2002/0172820 A1 | 11/2002 | Majumdar et al. |
| 2002/0175408 A1 | 11/2002 | Majumdar et al. |
| 2002/0179434 A1 | 12/2002 | Dai et al. |
| 2002/0187504 A1 | 12/2002 | Reich et al. |
| 2003/0001091 A1 | 1/2003 | Nakayama et al. |
| 2003/0003300 A1 | 1/2003 | Korgel et al. |
| 2003/0032892 A1 | 2/2003 | Erlach et al. |
| 2003/0048619 A1 | 3/2003 | Kaler et al. |
| 2003/0073071 A1 | 4/2003 | Fritz et al. |
| 2003/0089899 A1 | 5/2003 | Lieber et al. |
| 2003/0098488 A1 | 5/2003 | O'Keeffe et al. |
| 2003/0113713 A1 | 6/2003 | Glezer et al. |
| 2003/0113940 A1 | 6/2003 | Erlanger et al. |
| 2003/0121764 A1 | 7/2003 | Yang et al. |
| 2003/0124509 A1 | 7/2003 | Kenis et al. |
| 2003/0124717 A1 | 7/2003 | Awano et al. |
| 2003/0134267 A1 | 7/2003 | Kang et al. |
| 2003/0134433 A1 | 7/2003 | Gabriel et al. |
| 2003/0135971 A1 | 7/2003 | Liberman et al. |
| 2003/0156992 A1 | 8/2003 | Anderson et al. |
| 2003/0186522 A1 | 10/2003 | Duan |
| 2003/0186544 A1 | 10/2003 | Matsui et al. |
| 2003/0189202 A1 | 10/2003 | Li et al. |
| 2003/0197456 A1 | 10/2003 | Den et al. |
| 2003/0200521 A1 | 10/2003 | DeHon et al. |
| 2004/0005723 A1 | 1/2004 | Empedocles et al. |
| 2004/0026684 A1 | 2/2004 | Empedocles |
| 2004/0067530 A1 | 4/2004 | Gruner |
| 2004/0095658 A1 | 5/2004 | Buretea et al. |
| 2004/0106203 A1 | 6/2004 | Stasiak et al. |
| 2004/0112964 A1 | 6/2004 | Empedocles et al. |
| 2004/0113138 A1 | 6/2004 | DeHon et al. |
| 2004/0113139 A1 | 6/2004 | DeHon et al. |
| 2004/0118448 A1 | 6/2004 | Scher et al. |
| 2004/0136866 A1 | 7/2004 | Pontis et al. |
| 2004/0146560 A1 | 7/2004 | Whiteford et al. |
| 2004/0157414 A1 | 8/2004 | Gole et al. |
| 2004/0213307 A1 | 10/2004 | Lieber et al. |
| 2005/0037374 A1 | 2/2005 | Melker et al. |
| 2005/0064185 A1 | 3/2005 | Buretea et al. |
| 2005/0064731 A1 | 3/2005 | Park et al. |
| 2005/0066883 A1 | 3/2005 | Dubrow et al. |
| 2005/0072213 A1 | 4/2005 | Besnard et al. |
| 2005/0079533 A1 | 4/2005 | Samuelson et al. |
| 2005/0079659 A1 | 4/2005 | Duan et al. |
| 2005/0100960 A1 | 5/2005 | Dai et al. |
| 2005/0101026 A1 | 5/2005 | Sailor et al. |
| 2005/0109989 A1 | 5/2005 | Whiteford et al. |
| 2005/0110064 A1 | 5/2005 | Duan et al. |
| 2005/0117441 A1 | 6/2005 | Lieber et al. |
| 2005/0161662 A1 | 7/2005 | Majumdar et al. |

| | | |
|---|---|---|
| 2005/0181587 A1 | 8/2005 | Duan et al. |
| 2005/0201149 A1 | 9/2005 | Duan et al. |
| 2005/0202615 A1 | 9/2005 | Duan et al. |
| 2005/0212079 A1 | 9/2005 | Stumbo et al. |
| 2005/0214967 A1 | 9/2005 | Scher et al. |
| 2005/0219788 A1 | 10/2005 | Chow et al. |
| 2005/0230356 A1 | 10/2005 | Empedocles et al. |
| 2005/0253137 A1 | 11/2005 | Whang et al. |
| 2005/0266662 A1 | 12/2005 | Yi |
| 2005/0287717 A1 | 12/2005 | Heald et al. |
| 2006/0008942 A1 | 1/2006 | Romano et al. |
| 2006/0009003 A1 | 1/2006 | Romano et al. |
| 2006/0019472 A1 | 1/2006 | Pan et al. |
| 2006/0160246 A1 | 7/2006 | Massey et al. |
| 2006/0269927 A1 | 11/2006 | Lieber et al. |
| 2007/0252136 A1 | 11/2007 | Lieber et al. |
| 2007/0281156 A1 | 12/2007 | Lieber et al. |
| 2008/0191196 A1 | 8/2008 | Lu et al. |
| 2009/0004852 A1 | 1/2009 | Lieber et al. |

FOREIGN PATENT DOCUMENTS

| | | |
|---|---|---|
| JP | 11/11917 A2 | 1/1999 |
| JP | 2000/31462 | 1/2000 |
| WO | WO 91/06036 A1 | 5/1991 |
| WO | WO 95/02709 A2 | 1/1995 |
| WO | WO 96/29629 A2 | 9/1996 |
| WO | WO 97/33737 A1 | 9/1997 |
| WO | WO 97/34025 A1 | 9/1997 |
| WO | WO 98/39250 A1 | 9/1998 |
| WO | WO 98/42620 A1 | 10/1998 |
| WO | WO 98/48456 A1 | 10/1998 |
| WO | WO 99/63347 A2 | 12/1999 |
| WO | WO 00/09443 A1 | 2/2000 |
| WO | WO 00/17101 A1 | 3/2000 |
| WO | WO 00/19494 A1 | 4/2000 |
| WO | WO 00/29617 A3 | 5/2000 |
| WO | WO 00/51186 A2 | 8/2000 |
| WO | WO 01/03208 A1 | 1/2001 |
| WO | WO 01/44796 A1 | 6/2001 |
| WO | WO 02/17362 A2 | 2/2002 |
| WO | WO 02/31183 A1 | 4/2002 |
| WO | WO 02/48701 A2 | 6/2002 |
| WO | WO 02/080280 A1 | 10/2002 |
| WO | WO 02/086480 A1 | 10/2002 |
| WO | WO 03/005450 A2 | 1/2003 |
| WO | WO 03/016901 A1 | 2/2003 |
| WO | WO 03/053851 A2 | 7/2003 |
| WO | WO 03/054931 A1 | 7/2003 |
| WO | WO 03/063208 A2 | 7/2003 |
| WO | WO 2004/003535 A1 | 1/2004 |
| WO | WO 2004/010552 A1 | 1/2004 |
| WO | WO 2004/032190 A2 | 4/2004 |
| WO | WO 2004/032193 A2 | 4/2004 |
| WO | WO 2004/034025 A2 | 4/2004 |
| WO | WO 2005/089165 A2 | 9/2005 |
| WO | WO 2005/093831 A1 | 10/2005 |
| WO | WO 2005/094440 A2 | 10/2005 |
| WO | WO 2005/114282 A2 | 12/2005 |
| WO | WO 2005/119753 A2 | 12/2005 |
| WO | WO 2006/107312 A1 | 10/2006 |
| WO | WO 2007/145701 A2 | 12/2007 |
| WO | WO 2008/027078 A2 | 3/2008 |
| WO | WO 2008/033303 A2 | 3/2008 |
| WO | WO 2008/123869 A2 | 10/2008 |
| WO | WO 2008/127314 A1 | 10/2008 |

OTHER PUBLICATIONS

Chen, J., et al., "Large On-Off Ratios and Negative Differential Resistance in a Molecular Electronic Device," *Science*, vol. 286, pp. 1550 (1999).

Chen, R.J., et al, "Noncovalent functionalization of carbon nanotube for highly specific electronic biosensors," *PNAS*, vol. 100, No. 9, pp. 4984-4989 (2003).

Cheung, C.L., et al., "Diameter Controlled Synthesis of Carbon Nanotubes," *J. Phys. Chem B*, 106, (2002), pp. 2429/2433.

Choi, K.J., et al., "Enhancement of Ferroelectricity in Strained $BaTiO_3$ Thin Films," *Science*, vol. 306, pp. 1005 (2004).

Chung, S. W, et al., "Silicon nanowire devices," *App. Phy. Letters*, vol. 76, No. 15, pp. 2068 (2000).

Collier, C.P., et al., "Electronically Configurable Molecular/Based Logic Gates", *Science*, vol. 285, Jul. 16, 1999, pp. 391/394.

Cui, et al., "Nanowire nanosensors for highly sensitive and selective detection of biological and chemical species", *Science*, Aug. 17, 2001, vol. 293, pp. 1289/1292.

Cui, Yi, et al. "Doping and Electrical Transport in Silicon Nanowires", *The Journal of Physical Chemistry*, vol. 104, No. 22, Jun. 8, 2000, pp. 5213/5216.

Cui, Yi, et al., "Diameter/controlled synthesis of single/crystal silicon nanowires", *Applied Physics Letters*, vol. 78, No, 15, Apr. 9, 2001, pp. 2214/2216.

Cui, Yu, et al., "Functional Nanoscale Electronic Devices Assembled Using Silicon Nanowire Building Blocks", *Science*, vol. 291, Feb. 2, 2001, pp. 851/853.

Duan, X., et al., "High-performance thin-film transistors using semiconductor nanowires and nanoribbons," *Letters to Nature*, vol. 425, pp. 274 (2002).

Duan, X., et al., "Nonvolatile Memory and Programmable Logic from Molecule/Gated Nanowires," *Nano Letters*, 2(5), (2002), pp. 487/490.

Duan, X., et al., "Single/nanowire electrically driven lasers," *Nature*, 421, (2003), pp. 241/245.

Duan, X., et al., "Synthesis and optical properties of gallium arsenide nanowires," *App. Phys. Letters*, vol. 76, No. 9, pp. 1116 (2000).

Duan, Xiangfeng, et al., "General Synthesis of Compound Semiconductor Nanowires", *Adv. Materials. 2000*, 12, No. 4, pp. 298/302, published on Web Feb. 17, 2000.

Duan, Xiangfeng, et al., "Indium phosphide nanowires as building blocks for nanoscale electronic and optoelectronic devices", *Nature*, vol. 409, Jan. 4, 2001, pp. 66/69.

Duan, Xiangfeng, et al., "Laser/Assisted Catalytic Growth of Single Crystal GaN Nanowires", *J. Am. Chem. Soc. 2000*, 122, Oct. 18, 1999, pp. 188/189; published on Web Dec. 18, 1999.

Esfarjani, K., et al., "Electronic and transport properties of N-P doped nanotubes," *App. Phys. Letters*, Vol, 74, No. 1, pp. 79 (1999).

Friedman, R.S., et al., "High-speed integrated nanowire circuits," *Nature*, vol. 434, pp. 1085 (2005).

Givargizov, E.I., et al., "Fundamental Aspects of VLS Growth," *J. Crystal Growth*, 31, (1975), pp. 20/30.

Gradecak, S., et al., "GaN nanowire lasers with low lasing thresholds," *App. Phys. Letters*, vol. 87, pp. 173111-1 (2005).

Gudiksen et al., "Growth of nanowire superlattice structures for nanoscale photonics and electronics", *Nature*, 2002, vol. 415, pp. 617/620.

Gudiksen, M.S., et al., "Size/Dependent Photoluminescence from Single Indium Phosphide Nanowires," *J. Phys. Chem. B*, 106, (2002), pp. 4036/4039.

Gudiksen, M.S., et al., "Synthetic Control of the Diameter and Length of Single Crystal Semiconductor Nanowires," *J. Phys. Chem. B*, 105, (2001), pp. 4062/4064.

Gudiksen, Mark S., et al. "Diameter/Selective Synthesis of Semiconductor Nanowires", *J. Am. Chem. Soc. 2000*, 122, Jun. 6, 2000, pp. 8801/8802.

Guo, L., et al., "A Silicon Single-Electron Transistor Memory Operating at Room Temperature," *Science*, vol. 275, pp. 649 (1997).

Guo, L., et al., "Nanoscale silicon field effect transistors fabricated using imprint lithography," *Appl. Phys. Lett.*, vol. 71, pp. 1881 (1997).

Hahm, J., et al,, "Direct Ultrasensitive Electrical Detection of DNA and DNA Sequence Variations Using Nanowire Nanosensors," *Nano Letters*, vol. 4, No. 1, pp. 51-54 (2004).

Haraguchi et al, "Polarization dependence of light emitted from GaAs p/n junctions in quantum wire crystals", *Journal of Applied Physics*, Apr. 1994, vol. 75, No. 8, pp. 4220/4225.

Haraguchi, K., et al, "GaAs p-n junction formed in quantum wire crystals," *Appl. Phys. Lett.*, vol. 60, pp. 745 (1992).

Heath, J.R., et al., "A liquid solution synthesis of single crystal germanium quantum wires," *Chemical Physics Letters*, vol. 208, No. 3, 4, pp. 263 (1993).

Hiruma, K., et al., "GaAs fr e-standing quantum-siz wires," *J Appl. Phys.*, vol. 74, pp. 3162 (1993).

Hiruma, K., et al., "Self/organized growth of GaAs/InAs heterostructure nanocylinders by organometallic vapor phase epitaxy," *J. Crystal Growth*, 163, (1996), pp. 226/231.

Holmes, et al., Control of Thickness and Orientation of Solution/Grown Silicon Nanowires, Science, 287, (2000), pp. 1471/1473.

Hu, et al., "Serpentine Superlattice Nanowire-Array Lasers," *Journal of Quantum Electronics*, vol. 31, No. 8, pp. 1380-1388 (1995).

Hu, J., et al., "Chemistry and Physics in One Dimension: Synthesis and Properties of Nanowires and Nanotubes," *Acc. Chem. Res.*, 32, (1999), pp. 435/445.

Hu, J., et al., "Controlled growth and electrical properties of heterojunctions of carbon nanotubes and silicon nanowires," *Nature*, 399, (1999), pp. 48/51.

Huang et al., "Logic gates and computation from assembled nanowire building blocks", *Science*, 2000, vol. 287, pp. 624/625.

Huang, M., et al., "Room/Temperature Ultraviolet Nanowire Nanolasers," *Science*, 292, (2001), pp. 1897/1898.

Huang, Y., et al., "Gallium Nitride Nanowire Nanodevices," *Nano Letters*, 2(2), (2002), pp. 101/104.

Huang, Yu, et al., "Directed Assembly of One/dimensional Nanostructures into Functional Networks", *Science*, vol. 291, Jan. 26, 2001, pp. 630/633.

"IBM creates highest performing nanotube transistors", IBM News, 2002.

Javey, A., et al., "Ballistic carbon nanotube field-effect transistors," *Nature*, vol. 424, pp. 654 (2003).

Jin, S., et al., "Scalable Interconnection and Integration of Nanowire Devices without Registration," *Nano Letters*, vol. 4, No, 5, pp. 915-919 (2004).

Johnson, J.C., et al., "Single gallium nitride nanowire lasers," *Nature Materials*, 1, (2002), pp. 106/110.

Johnson, J.C., et al., "Single Nanowire Lasers," *J. Phys. Chem.*, 105(46), (2001), pp. 11387/11390.

Joselevich, E., et al., "Vectorial Growth of Metallic and Semiconducting Single/Wall Carbon Nanotubes," *Nano Letters*, 2(10), (2002), pp. 1137/1141.

Kanjanachuchai et al., "Coulomb blockade in strained/Si nanowires on leaky virtual substrates", *Semiconductor Science and Technology*, 2001, vol. 16, pp. 72/76.

Kong et al. "Nanotube molecular wires as chemical sensors", *Science*, Jan. 28, 2000, vol. 287, pp. 622/625.

Kong, J., et al., "Chemical vapor deposition of methane for single/walled carbon nanotubes," *Chem. Physics Letters*, 292, (1998), pp. 567/574.

Kong, J., et al., "Synthesis of individual single/walled carbon natubes on patterned silicon wafers," *Nature*, 395, (1998), pp. 878/881.

Lahoun et al., "Epitaxial core/shell and core/multishell nanowire heterostructures", *Nature*, 2002, vol. 420, pp. 57/61.

Lahoun, L.J., et al., "Semiconductor nanowire heterostructures," *Phil. Trans. R. Soc. Lond.*, vol. 362, pp. 1247-1260 (2004).

Law, M., et al., "Nanoribbon Waveguides for Subwavelength Photonics Integration," *Science*, vol. 305, pp. 1269-1273 (2004).

Leff, D.V., et al., "Thermodynamic Control of Gold Nanocrystal Size: Experiment and Theory," *J. Phys. Chem.*, vol. 99, pp. 7036-7041 (1995).

Lei, B., et al., "Nanowire transistors with ferroelectric gate dielectrics: Enhanced performance and memory effects," *Applied Physics Letters*, Vol, 84, No. 22, pp. 4553-4555 (2004).

Lieber, C.M., "Nanoscale Science and Technology Building a Big Future from Small Things," *MRS Bulletin*, July, pp. 486-491 (2003).

Lieber, C,M., "Nanowire Superlattices," *Nano Letters*, vol. 2, No. 2, pp. 81-82 (2002).

Lu, W., et al., "One-dimensional hole gas in germanium/silicon nanowire heterostructures," *PNAS*, vol. 102, No. 29, pp. 10046-10051 (2005).

Martel, R., et al., "Single/ and multi/wall carbon nanotube field/effect transistors," *Apl Phys Lett*, 73(17), (1998), pp. 2447/2449.

McAlpine, M.C., et al., "High-Performance Nanowire Electronics and Photonics on Glass and Plastic Substrates," *Nano Letters*, vol. 3, No. 11, pp. 1531-1535 (2003).

McAlpine, M.C., et al., "High-Performance Nanowire Electronics and Photonics and Nanoscale Patterning on Flexible Plastic Substrates," *Proceedings of the IEEE*, vol. 93, No. 7, pp. 1357-1363 (2005).

McAlpine, M.C., et al., "Nanoimprint Lithography for Hybrid Plastic Electronics," *Nano Letters*, vol. 3, No. 4, pp. 443-445 (2003).

Menon, V.P., et al., "Fabrication and Evaluation of Nanoelectrode Ensembles," *Anal., Chem.*, vol. 67, pp. 1920-1928 (1995).

Mizutani, T., et al., "Fabrication and characterization of carbon nanotube FETs," *Proceedings of SPIE*, vol. 5732, pp. 28-36 (2005).

Morales, A.M., et al., "A Laser Ablation Method for the Synthesis of Crystalline Semiconductor Nanowires," *Science*, vol. 279, pp. 208-211 (1998).

Musin, R.N., et al., "Structural and electronic properties of epitaxial core-shell nanowire heterostructures," *Physical Review*, vol. 71, pp. 155318-1155381-4 (2005).

Nosho, Y., et al., "*n*-type carbon nanotube field-effect transistors fabricated by using Ca contact electrodes," *Applied Physics Letters*, vol. 86, pp. 073105 (2005).

Padeste, C., et al., "Modular Amperometric Immunosensor Devices," *Transducers*, pp. 487-490 (1995).

Patolsky, F., et al., "Electrical detection of single viruses," *PNAS*, vol. 101, No. 39, pp. 14017-14022 (2004).

Patolsky, F., et al., "Nanowire Nanosensors," *Materials Today*, pp. 20-28 (2005).

Patolsky, Fernando et al. "Nanowire-Based Biosensors" Analytical Chemistry, Jul. 1, 2006, pp. 4261-4269.

Pavesi, L., et al., "Optical gain in silicon nanocrystals," *Nature*, vol. 408, pp. 440-444 (2000).

Qi, P., et al., "Toward Large Arrays of Multiplex Functionalized Carbon Nanotube Sensors for Highly Sensitive and Selective Molecular Detection," *Nano Letters*, vol. 3, No. 3, pp. 347-351 (2003).

Rueckes, T., et al., "Carbon Nanotube/Based Nonvolatile Random Access Memory for Molecular Computing," *Science*, 298, (2000), pp. 94/97.

Shi, Y. et al. "Long Si Nanowires With Millimeter-Scale Length by Modified Thermal Evaporation From Si Powder" Appl. Phys. A 80, 1733-1736 (2005).

Star et al., "Preparation and properties of polymer/wrapped single/walled carbon nanotubes", *Angew. Chem. Int.*, 2001, vol. 40, No. 9, pp. 1721/1725.

Takayama, S., et al., "Patterning cells and their environments using multiple laminar fluid flows in capillary networks," *Proc. Natl. Acad. Sci.*, vol. 96, pp. 5545-5548 (1999).

Tans, S.J., et al., "Room-temperature transistor based on a single carbon nanotube," *Nature*, vol. 393, pp. 49-52 (1998).

Thess, A., et al., "Cyrstalline Ropes of Metallic Carbon Nanotubes," *Science*, 273, (1996), pp. 483/487.

Tiefenauer, L.X., et al., "Towards amperometric immunosensor devices," *Biosensors & Bloelectronics*, Vol. 12, No. 3, pp. 213-223 (1997).

Tong, L., et al., "Subwavelength-diameter silica wires for low-loss optical wave guiding," *Nature*, vol. 426, pp. 816-819 (2003).

Urban, J,J., et al., "Single-Crystalline Barium Titanate Nanowires," *Adv. Mat.*, vol. 15, No. 5, pp. 423-426 (2003).

Vossmeyer, T., et al., "Combinatorial approaches toward patterning nanocrystals," *J. of Applied Physics*, vol. 84, No. 7, pp. 3664-3670 (1998).

Wang et al., "Highly polarized photoluminescence and photodetection from single indium phosphide nanowires", *Science*, 2001, vol. 293, pp. 1455/1457.

Wang, D. et al. "Rational Growth of Branched and Hyperbranched Nanowire Structures" Nano Letters, 2004, vol. 4, No. 5, pp. 871-874.

Wang, N., et al., "$SiO_2$/enhanced synthesis of Si nanowires by laser ablation," *App. Physics Letters*, 73(26), (1998), pp. 3902/3904.

Wang, W.U., et al., "Label-free detection of small-molecule-protein interactions by using nanowire nanosensores," *PNAS*, vol. 102, No. 9, pp. 3208-3212 (2005).

Wei, Q., et al., "Synthesis of Single Crystal Bismuth/Telluride and Lead/Telluride Nanowires for New Thermoelectric Materials," *Mat. Res. Soc. Symp. Proc.*, 581, (2000), pp. 219/223.

Whang, D., et al., "Large-Scale Hierarchical Organization of Nanowire Arrays for Integrated Nanosystems," *Nano Letters*, vol. 3, No. 9, pp. 1255-1259 (2003).
Whang, D., et al., "Nanolithography Using Hierarchically Assembled Nanowire Masks," *Nano Letters*, vol. 3, No. 7, pp. 951-954 (2003).
Wolf, S., et al., "Silicon Processing for the VLSI Era," *Lattice Press*, vol. 1, pp. 12-13 (2000).
Wong, S., et al., "Covalently funtionalized nanotubes as nanometre/sized probes in chemistry and biology," *Nature*, 394, (1998), pp. 52/55.
Wu et al., "Block/by/block growth of single/crystalline Si/SiGe superlattice nanowires", web release date, Jan. 19, 2002, http://pubs.acs.org/hotartcl/nalefd/2002/nl0156888_rev.html.
Wu, Y., et al, "Controlled Growth and Structures of Molecular-Scale Silicon Nanowires," *Nano Letters*, vol. 4, No. 3, pp. 433-436 (2004).
Wu, Y., et al., "Single-crystal metallic nanowires and metal/semiconductor nanowire heterostructures," *Nature*, vol. 430, pp. 61-65 (2004).
Xiang, J., et al., "Ge/Si nanowire heterostructures as high-performance field-effect transistors," *Nature*, vol. 441, pp. 489-493 (2006).
Yamada, T., "Analysis of submicron carbon nanotube field-effect transistors," *Applied Physics Letters*, vol. 76, No. 5, pp. 628-630 (2000).
Yang, P., "Wires on water," *Nature*, vol. 425, pp. 243-244 (2003).
Yang, P., et al., "Controlled Growth of ZnO Nanowires and Their Optical Properties," *Adv. Funct. Mater.*, Vol, 12, No. 5, pp. 323-331 (2002).
Yu, D.P., et al., "Nanoscale silicon wires synthesized using simple physical evaporation," *Applied Physics Letters*, vol. 72, No. 26, pp. 3458-3460 (1998).
Yu, J. et al. "One-Dimensional Silicon Nanostructures Fabricated by Thermal Evaporation" Materials Science & Engineering C26 (2006), pp. 800-804.
Zhang, Y.F. et al. "Bulk-Quantity Si Nanowires Synthesized by SiO Sublimation" Journal of Crystal Growth, 212 (2000) pp. 115-118.
Zheng, G., et al., "Multiplexed electrical detection of cancer markers with nanowire sensor arrays," *Nature*, vol. 23, No. 10, pp. 1294-1301 (2005).
Zheng, G., et al., "Synthesis and Fabrication of High-Performance n-Type Silicon Nanowire Transistors," *Advanced Materials*, Vol, 16, No. 21, pp. 1890-1893 (2004).
Zhong, Z., et al., "Coherent Single Charge Transport in Molecular-Scale Silicon Nanowires," *Nano Letters*, vol. 5, No. 6, pp. 1143-1146 (2005).
Zhong, Z., et al., "Nanowire Crossbar Arrays as Address Decoders for Inegrated Nanosystems," *Science*, vol. 302, pp. 1377-1379 (2003).
Zhong, Z., et al., "Synthesis of p-Type Gallium Nitride Nanowires for Electronic and Photonic Nanodevices," *Nano Letters*, vol. 3, No. 3, pp. 343-346 (2003).
Zhou, G., et al., "Growth morphology and micro/structural aspects of Si nanowires synthesized by laser ablation," *J. of Crystal Growth*, 197, (1999), pp. 129/135.
Office Action mailed Sep. 2, 2003 in U.S. Appl. No. 09/935,776, filed Aug. 22, 2001.
Office Action mailed Sep. 15, 2004 in U.S. Appl. No. 09/935,776, filed Aug. 22, 2001.
Office Action mailed Mar. 11, 2005 in U.S. Appl. No. 09/935,776, filed Aug. 22, 2001.
Office Action mailed Aug. 30, 2005 in U.S. Appl. No. 09/935,776, filed Aug. 22, 2001.
Office Action mailed May 16, 2006 in U.S. Appl. No. 09/935,776, filed Aug. 22, 2001.
Office Action mailed Jan. 15, 2003 in U.S. Appl. No. 10/020,004, filed Dec. 11, 2001.
Office Action mailed Jun. 25, 2004 in U.S. Appl. No. 10/020,004, filed Dec. 11, 2001.
Office Action mailed Mar. 14, 2005 in U.S. Appl. No. 10/020,004, filed Dec. 11, 2001.
Office Action mailed Aug. 30, 2005 in U.S. Appl. No. 10/020,004, filed Dec. 11, 2001.
Office Action mailed Jun. 30, 2004 in U.S. Appl. No. 10/196,337, filed Jul. 16, 2002.
Office Action mailed Jan. 3, 2005 in U.S. Appl. No. 10/196,337, filed Jul. 16, 2002.
Office Action mailed May 25, 2005 in U.S. Appl. No. 10/196,337, filed Jul. 16, 2002.
Office Action mailed Feb. 23, 2006 in U.S. Appl. No. 10/196,337, filed Jul. 16, 2002.
Office Action mailed Nov. 2, 2006 in U.S. Appl. No. 10/196,337, filed Jul. 16, 2002.
Office Action mailed Nov. 29, 2005 in U.S. Appl. No. 10/995,075, filed Nov. 22, 2004.
Office Action mailed Apr. 7, 2006 in U.S. Appl. No. 10/734,086, filed Dec. 11, 2003.
Office Action mailed Oct. 27, 2006 in U.S. Appl. No. 10/734,086, filed Dec. 11, 2003.
Office Action mailed Dec. 20, 2006 in U.S. Appl. No. 11/012,549, filed Dec. 15, 2004.
International Search Report in PCT Application No. PCT/US03/22061 filed Jul. 16, 2003.
International Search Report in PCT Application No. PCT/01/48230, filed Dec. 11, 2001.
International Prelim. Exam. Report from PCT Application No. PCT/01/48230, filed Dec. 11, 2001.
Written Opinion from Int. Apl. No. PCT Application No. PCT/01/48230, filed Dec. 11, 2001.
International Search Report from Int. Apl. No. PCT/US2005/004459, filed Feb. 14, 2005.
Written Opinion from Int. Apl. No. PCT/US2005/004459, filed Feb. 14, 2005.
International Search Report from Int. Apl. No. PCT/US03/22753, filed Jul. 21, 2003.
International Search Report from Int. Apl. No. PCT/US2005/026759, filed Jul. 28, 2005.
Written Opinion from Int. Apl. No. PCT/US2005/026759, filed Jul. 28, 2005.
Written Opinion from Int. Apl. No. PCT/US2005/020974, filed Jun. 15, 2005.
International Search Report from PCT/US2005/020974, filed Jun. 15, 2005.
International Search Report from PCT/US2005/034345, filed Sep. 21, 2005.
Written Opinion from PCT/US2005/034345, filed Sep. 21, 2005.
Office Action from U.S. Appl. No. 11/543,352 dated Sep. 12, 2008.
Office Action from U.S. Appl. No. 11/543,746 dated Sep. 8, 2008.
Office Action from U.S. Appl. No. 11/543,336 dated Jun. 18, 2008.
Office Action from U.S. Appl. No. 11/543,353 dated Oct. 6, 2008.
Office Action from U.S. Appl. No. 11/543,326 dated Oct. 14, 2008.
International Search Report and Written Opinion from PCT Application PCT/US2007/013700 dated May 29, 2008.
International Search Report and Written Opinion from PCT Application PCT/US2007/019669 dated Jan. 24, 2008.
International Search Report and Written Opinion from PCT Application PCT/US2007/024222 dated Oct. 10, 2008.
International Search Report and Written Opinion from PCT Application PCT/US2007/024126 dated Sep. 26, 2008.
Cui et al., "High performance silicon nanowire field effect transistors", *NANO Letters*, 3:2 (2003) pp. 149-152.
Office Action for U.S. Appl. No. 10/588,833 dated May 27, 2010.
European Office Action from European Patent Application 07873479.5 dated Apr. 7, 2010.

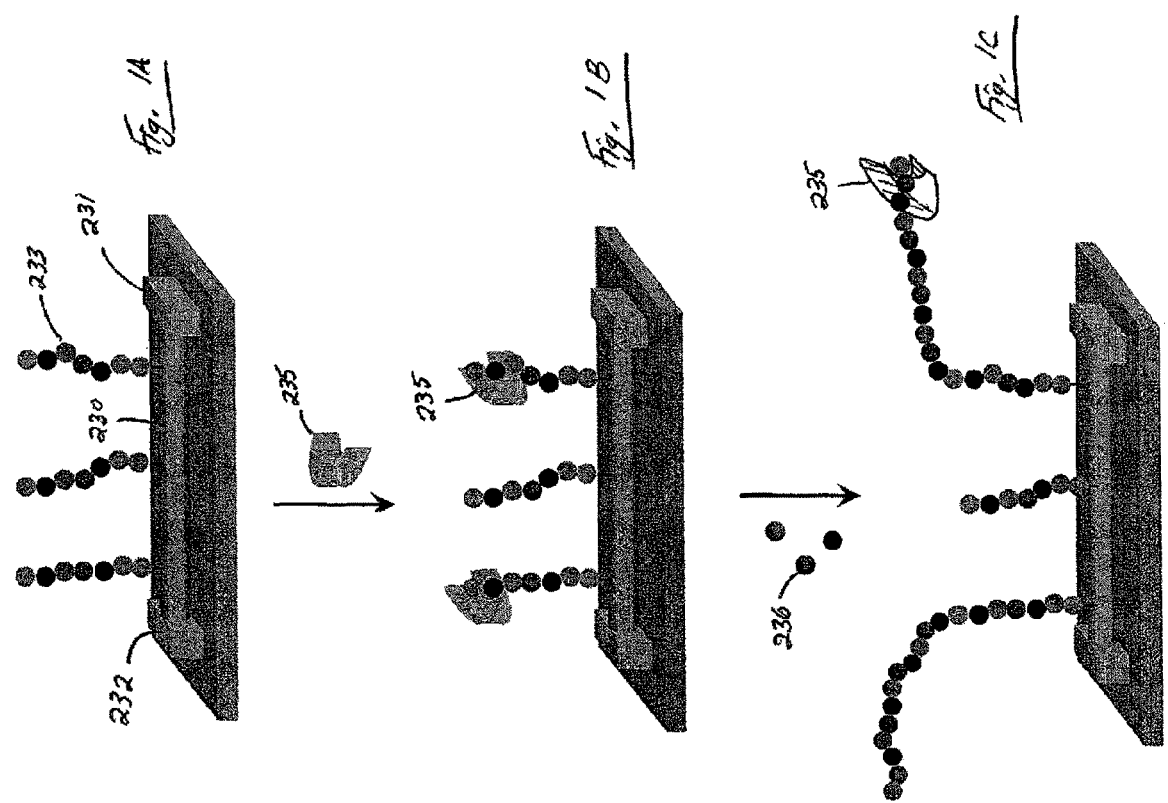

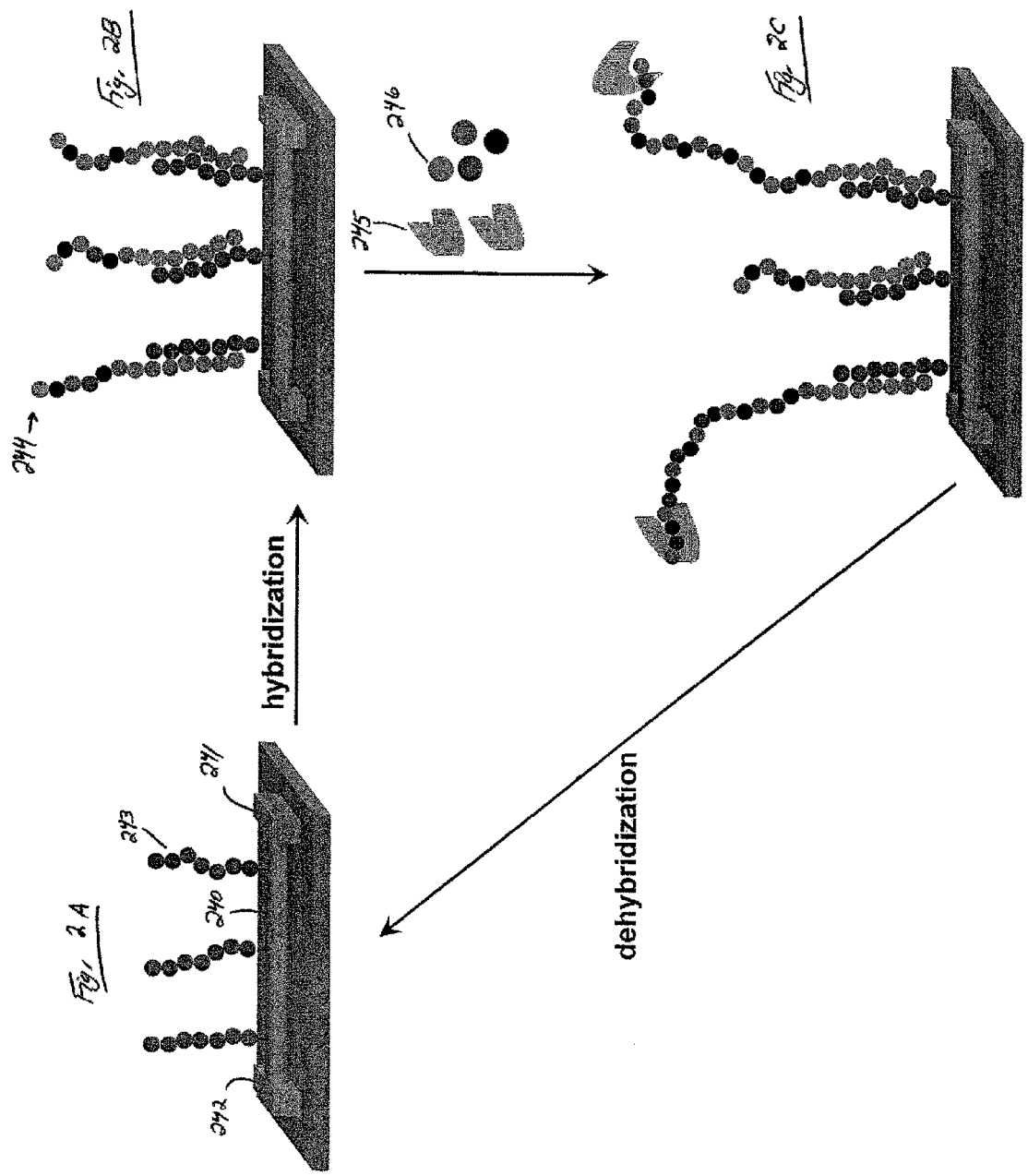

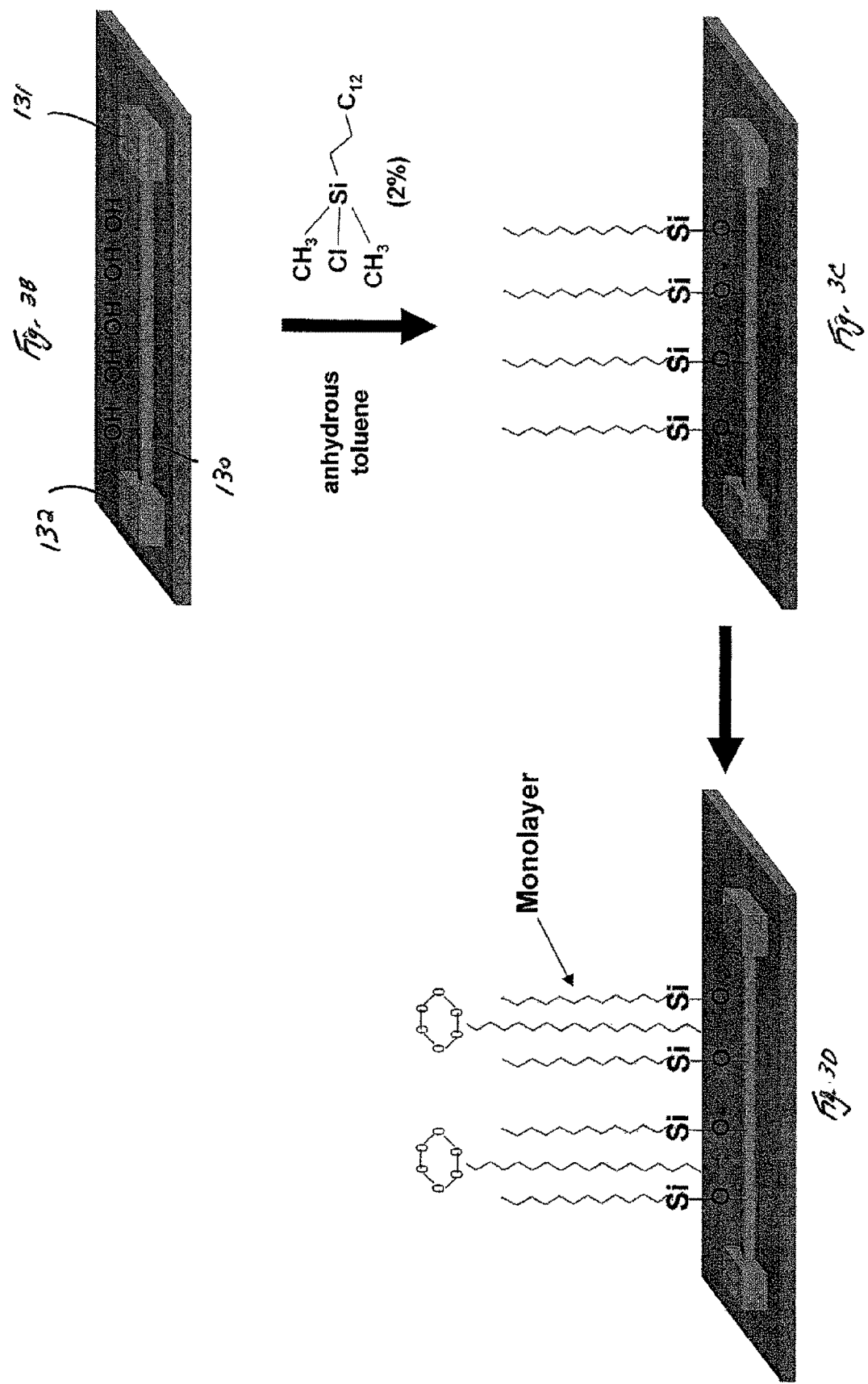

Fig. 10A    Fig. 10B
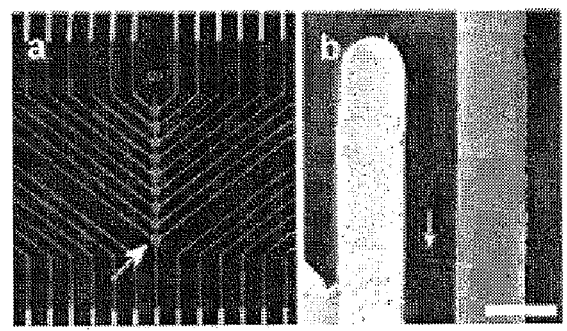
Fig. 11A
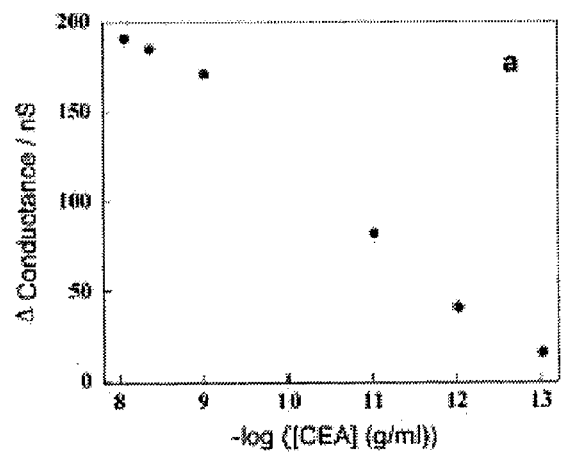
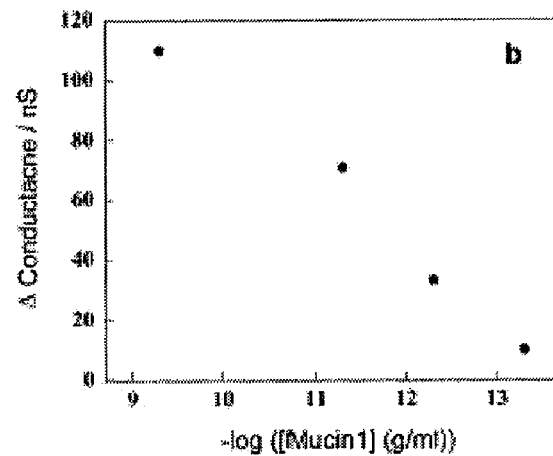
Fig. 11B

Fig. 17A
Fig. 17B
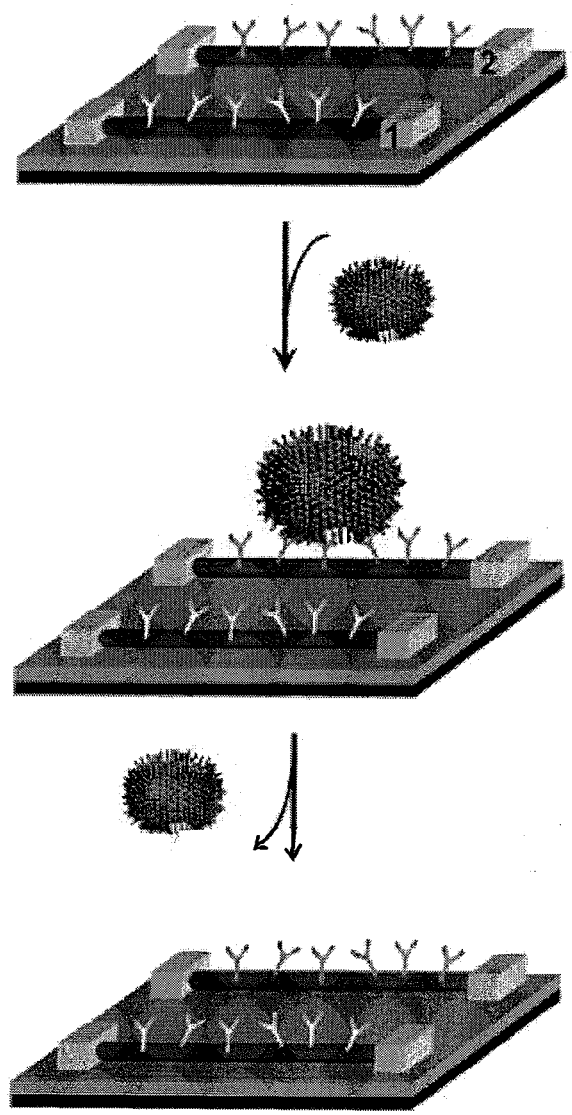
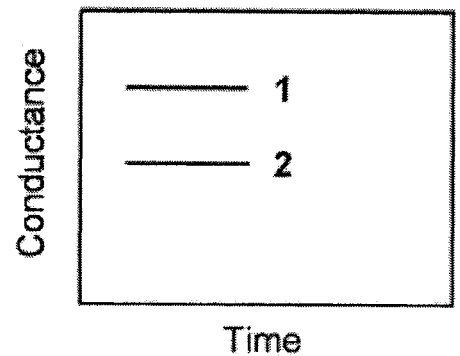
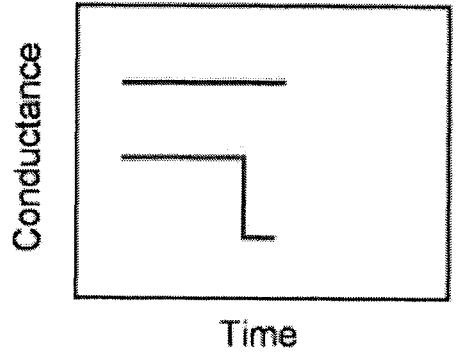
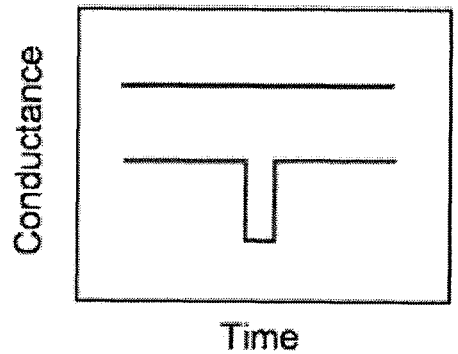

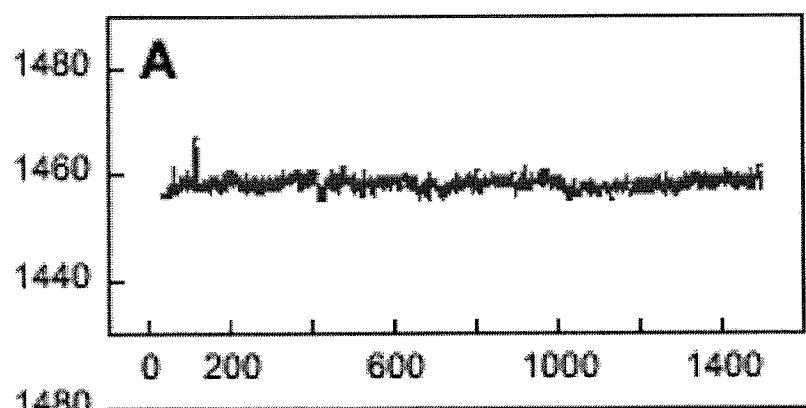
Fig. 19A
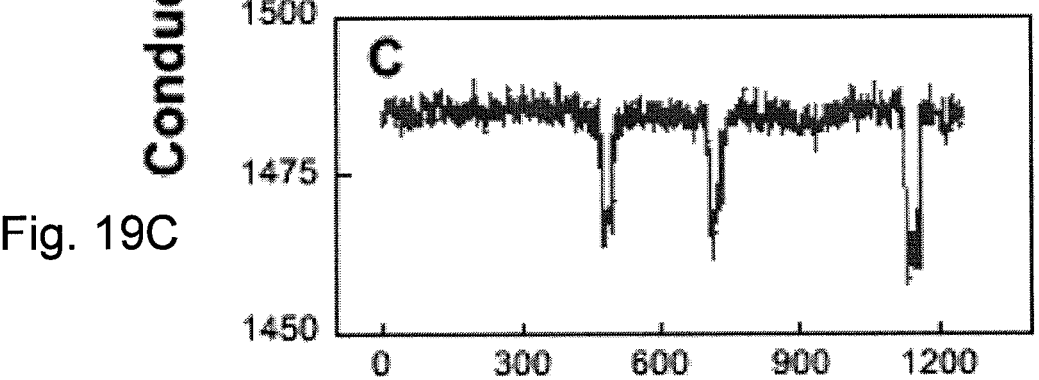
Fig. 19B
Fig. 19C
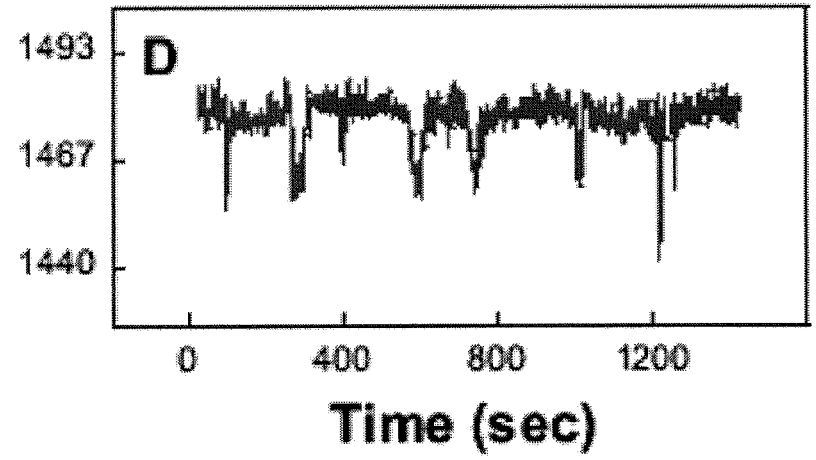
Fig. 19D

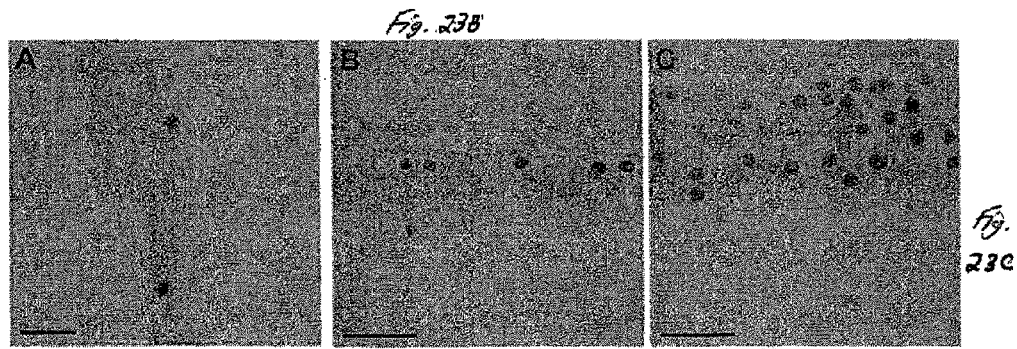
Fig. 23A  Fig. 23B  Fig. 23C
Fig. 23D
| Coverage | Particle coverage Au-NP/μm |
|---|---|
| Low | 10-13 |
| Medium | 50-100 |
| High | ≥500 |
Fig. 23E
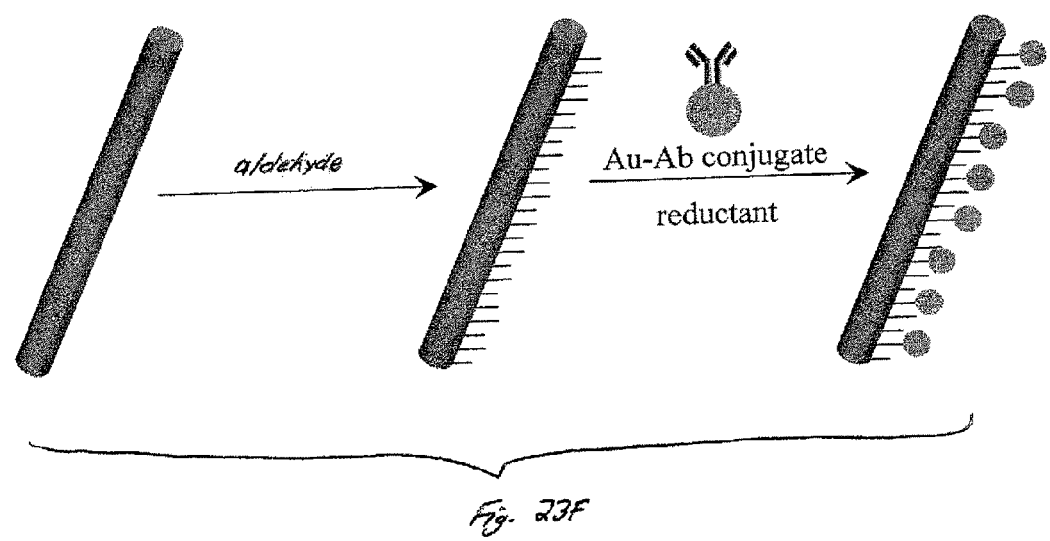
Fig. 23F

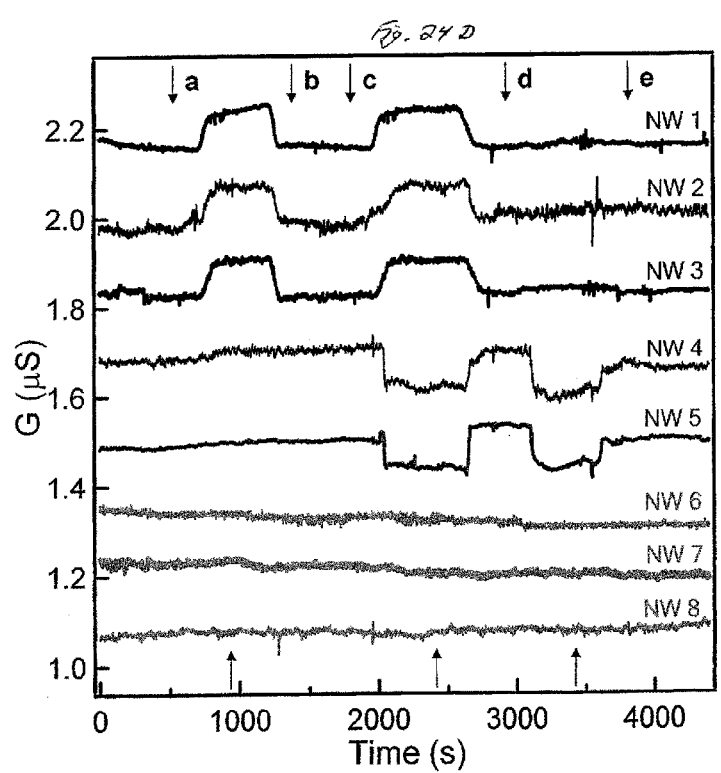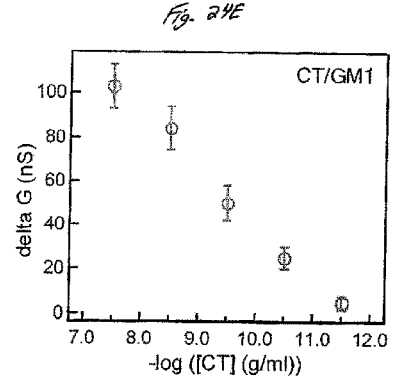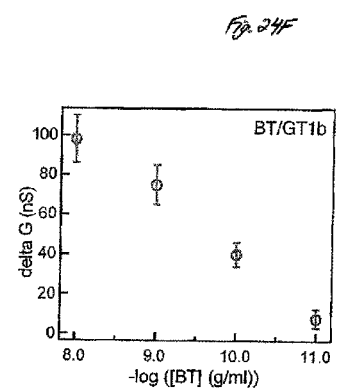

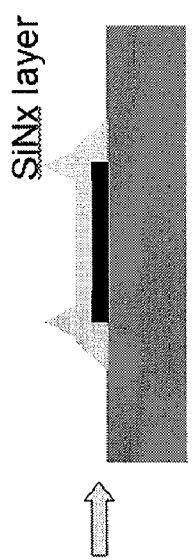
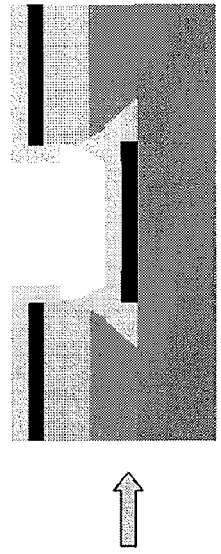
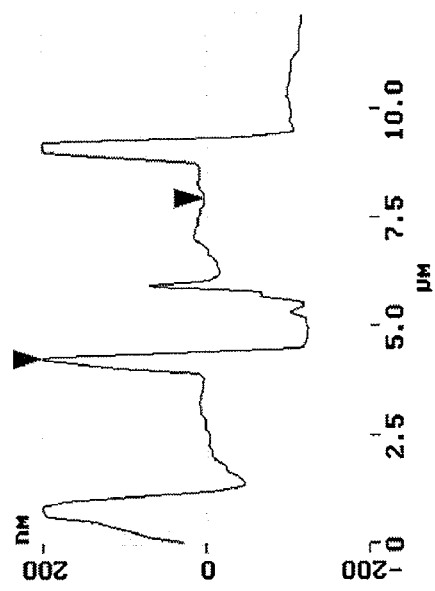
Fig. 25A
Fig. 25B
Fig. 25C
Fig. 25D
Fig. 25E Fig. 25H
| Electrode (w/o nanowires) & SiNx deposition condition | SiNx layer height | Leakage current in buffer solution |
|---|---|---|
| Ni (no passivation) | N/A | 3 nA |
| Ni + SiNx (200W, 600sec) | ~ 50 nm | 0.45~0.6 nA |
| Ni + SiNx (300W, 600sec) | ~ 70 nm | 0.2~0.3 nA |
| Ni + SiNx (400W, 600sec) | ~ 85 nm | 0.1~0.2 nA |
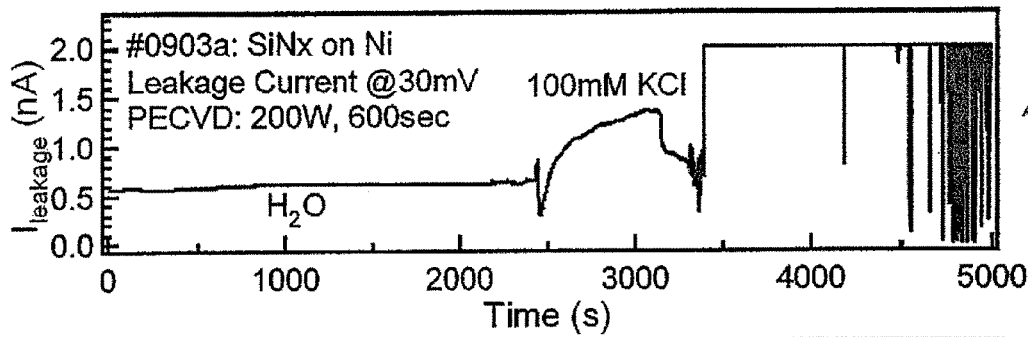
Fig. 25F
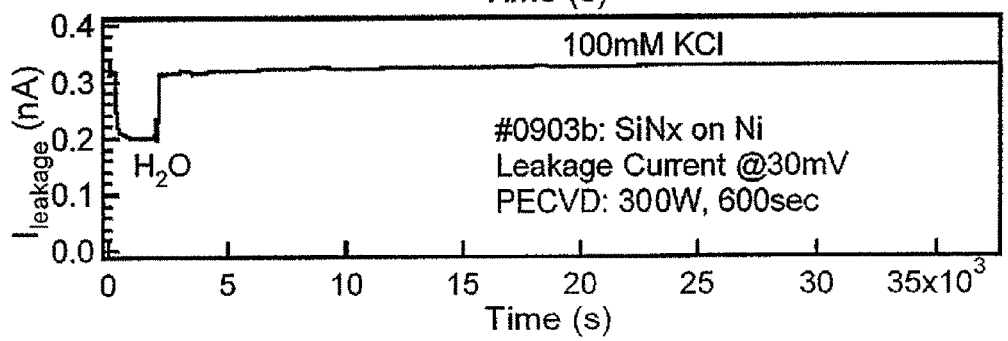
Fig. 25G Fig. 27A
Fig. 27B
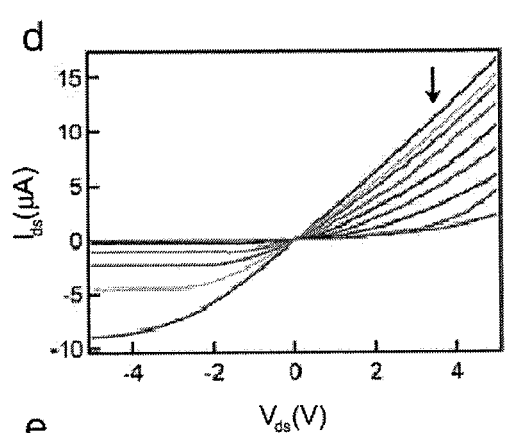
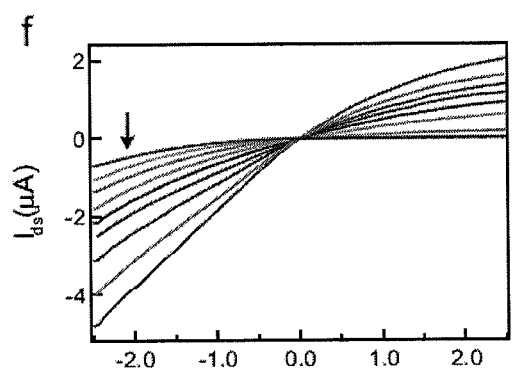
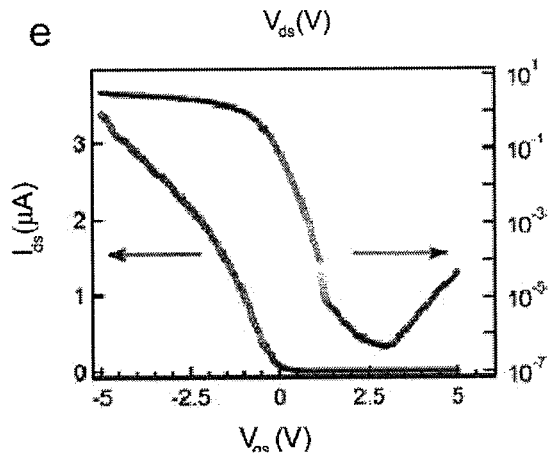
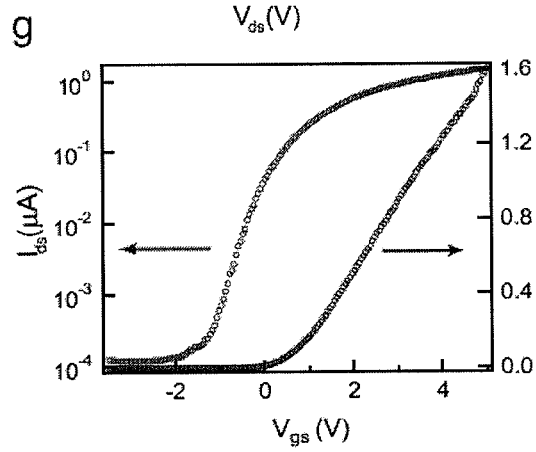
Fig. 27C
Fig. 27D

NANOSCALE SENSORS

RELATED APPLICATIONS

This application claims priority to all of the following according to the following to recitation of priority relationships. This application is a continuation of U.S. patent application Ser. No. 11/501,466, filed Aug. 8, 2006, entitled "Nanoscal Sensors", by Lieber, et al., which claims the benefit of U.S. Provisional Patent Application Ser. No. 60/707, 136, filed Aug. 9, 2005, entitled "Nanoscale Sensors," by Lieber, et al. Said application Ser. No. 11/501,466 is also a continuation-in-part of U.S. patent application Ser. No. 11/137,784, filed May 25, 2005, entitled "Nanoscale Sensors," by Lieber, et al. Each of these is incorporated herein by reference.

FEDERALLY SPONSORED RESEARCH

Research leading to various aspects of the present invention were sponsored, at least in part, by the Defense Advanced Research Projects Agency under Grant No. N66001-01-1-8903 and by the National Institutes of Health under Grant No. CA091357. The United States Government may have certain rights in the invention.

FIELD OF INVENTION

Various aspects of the present invention generally relate to nanoscale wire devices and methods for use in determining analytes suspected to be present in a sample, and systems and methods of immobilizing entities such as reaction entities relative to nanoscale wires.

BACKGROUND

Interest in nanotechnology, in particular sub-microelectronic technologies such as semiconductor quantum dots and nanowires, has been motivated by the challenges of chemistry and physics at the nanoscale, and by the prospect of utilizing these structures in electronic and related devices. Nanoscopic articles might be well-suited for transport of charge carriers and excitons (e.g. electrons, electron pairs, etc.) and thus may be useful as building blocks in nanoscale electronics applications. Nanowires are well-suited for efficient transport of charge carriers and excitons, and thus are expected to be important building blocks for nanoscale electronics and optoelectronics.

Nanoscale wires having selectively functionalized surfaces have been described in U.S. patent application Ser. No. 10/020,004, entitled "Nanosensors," filed Dec. 11, 2001, published as Publication No. 2002/0117659 on Aug. 29, 2002, and as corresponding International Patent Application Serial No. PCT/US01/48230, filed Dec. 11, 2001, published as International Patent Application Publication WO 02/48701 on Jun. 20, 2002 (each incorporated herein by reference). As described, functionalization of the nanoscale wire may permit interaction of the functionalized nanoscale wire with various entities, such as molecular entities, and the interaction induces a change in a property of the functionalized nanowire, which provides a mechanism for a nanoscale sensor device for detecting the presence or absence of an analyte suspected to be present in a sample.

SUMMARY OF THE INVENTION

Various aspects of the present invention generally relate to nanoscale wire devices and methods for use in determining analytes suspected to be present in a sample, and systems and methods of immobilizing entities such as reaction entities relative to nanoscale wires. The subject matter of the present invention involves, in some cases, interrelated products, alternative solutions to a particular problem, and/or a plurality of different uses of one or more systems and/or articles.

In one aspect, the invention is a method. In one set of embodiments, the method is a method of virus detection. The method, in one embodiment, includes an act of determining a single virus by causing the virus to bind an antibody. In some cases, the antibody is immobilized relative to a surface of a nanoscale wire via a nitrogen-containing bond.

In another set of embodiments, the method is a method of cancer diagnosis. In one embodiment, the method includes acts of exposing a sample suspected of containing a telomerase to a nucleic acid immobilized relative to a nanoscale wire, determining binding of the telomerase to the nucleic acid, and diagnosing cancer based on the binding of the telomerase to the nucleic acid.

The method, in yet another set of embodiments, is a method of determining a toxin. In one embodiment, the method includes acts of exposing a sample suspected of containing a toxin to a ganglioside immobilized relative to a nanoscale wire, and determining binding of the toxin to the ganglioside.

In still another set of embodiments, the method includes acts of adding one or more nucleotides, using a telomerase, to a nucleic acid immobilized relative to a nanoscale wire.

In one set of embodiments, the method includes acts of exposing a sample suspected of containing a nucleic acid synthesis enzyme to a nucleic acid immobilized relative to a nanoscale wire, and determining binding of the enzyme to the nucleic acid. The method, in another set of embodiments, includes an act of adding one or more nucleotides to a nucleic acid immobilized relative to a nanoscale wire. In still another set of embodiments, the method includes acts of immobilizing a first nucleic acid relative to to a nanoscale wire, and immobilizing a second nucleic acid relative to the first nucleic acid.

The method, in yet another set of embodiments, includes an act of replacing a first nucleic acid immobilized relative to a nanoscale wire with a second nucleic acid without breaking a covalent bond between the first nucleic acid and the nanoscale wire. In another set of embodiments, the method includes an act of replacing a first protein immobilized relative to a nanoscale wire with a second protein without breaking a covalent bond between the first protein and the nanoscale wire. The method includes, in still another set of embodiments, acts of providing a nucleic acid immobilized relative to a nanoscale wire, immobilizing an entity relative to the nucleic acid, determining an electrical property of the nanoscale wire, and determining a property of the nucleic acid using the electrical property.

Another set of embodiments of the invention provides a method of detecting an uncharged analyte. In one embodiment, the method includes acts of providing a liquid comprising an analyte that is uncharged, immobilizing the species relative to the nucleic acid, altering pH of the liquid such that the entity becomes charged, and determining an electrical property of the nanoscale wire to detect the analyte.

The method, according to another set of embodiments, includes an act of covalently bonding an entity to a surface of a nanoscale wire by forming an imine bond between the nanoscale wire and the entity. In still another set of embodiments, the method includes an act of covalently bonding an entity to a surface of a nanoscale wire by forming an amide bond between the nanoscale wire and the entity. In yet another set of embodiments, the method includes an act of reacting a surface of a nanoscale wire with an aldehyde to produce an aldehyde-functionalized surface. The method, in another set of embodiments, includes an act of reacting a surface of a nanoscale wire with an amine to produce an amine-functionalized surface. In yet another set of embodiments, the method includes an act of reacting a surface of a nanoscale wire with a thiol to produce a thiol-functionalized surface.

In another set of embodiments, the method includes an act of reacting a molecule comprising a halogenated silane with a nanoscale wire such that at least a portion of the silane becomes covalently bonded to the nanoscale wire.

The method, according to still another set of embodiments, includes acts of to providing a nanoscale wire having a surface, at least a portion of the surface comprising a monolayer covalently bonded thereon, and immobilizing an entity relative to the monolayer via a hydrophobic interaction between at least a portion of the entity and the monolayer. In another set of embodiments, the method includes acts of providing a nanoscale wire having a surface, at least a portion of the surface comprising one or more layers of molecules covalently immobilized relative to the nanoscale wire, and immobilizing an entity relative to the one or more layers via a hydrophobic interaction between at least a portion of the entity and the one or more layers.

In one set of embodiments, the method includes acts of providing a solution containing a concentration of an analyte of interest and a total solute concentration at least about 1000 times greater than the concentration of the analyte of interest, and determining the analyte of interest in solution using a nanoscale wire comprising an entity able to bind the analyte.

The method, in yet another set of embodiments, includes an act of annealing a nickel electrode to a nanoscale wire.

In one set of embodiments, the method includes acts of attaching, to the surface of a nanoscale wire, a layer of molecules, determining the thickness of the layer on the nanoscale wire, and thereafter, attaching an entity to at least a portion of the layer of the nanoscale wire. In another set of embodiments, the method includes acts of forming a precursor of a linker on a nanoscale wire, under conditions preselected to apply a controlled thickness of the precursor to the nanoscale wire, and covalently attaching an entity to the precursor to form an entity covalently linked via the linker to the nanoscale wire.

In another aspect, the invention is an article. The article, according to one set of embodiments, includes a nanoscale wire, a first nucleic acid immobilized relative to a nanoscale wire, and a second nucleic acid immobilized relative to the first nucleic acid.

The article includes a nanoscale wire having a surface, in one set of embodiments. In one embodiment, at least a portion of the surface is aldehyde-functionalized, amine-functionalized, and/or thiol-functionalized. In another embodiment, at least a portion of the surface comprises a monolayer covalently bonded thereon. In still another embodiment, at least a portion of the surface comprises one or more layers of molecules covalently immobilized relative to the nanoscale wire. In yet another embodiment, at least a portion of the surface comprises more than one layer covalently immobilized relative thereto. The article includes, in another set of embodiments, a ganglioside immobilized relative to a nanoscale wire.

In yet another set of embodiments, the article includes a microarray comprising a plurality of sensing regions. In some cases, at least some of the sensing regions comprise a plurality of nanoscale wires that are individually addressable. In certain instances, at least some of the nanoscale wires comprise reaction entities. In one embodiment, the microarray contains the individually addressable nanoscale wires at a density of at least about 120 nanoscale wires/$cm^2$.

The article, in still another set of embodiments, includes a first electrode, a first electrical contact in electronic communication with the first electrode, a plurality of second electrodes, each of which is in electrical communication with a second electrical contact, and a plurality of nanoscale wires, at least some of which comprise reaction entities, at least some of which are disposed between the first electrode and one of the second electrodes.

In yet another set of embodiments, the article includes a nanoscale wire having a core, and optionally a shell, and a linker covalently attaching an entity to the nanoscale wire. In some cases, the distance between the entity and the outermost border of the core is no more than about 20 nm.

Yet another aspect of the present invention provides a nanoscale electrical sensor array device. In some embodiments, the device comprises a first electrode, a first nanoscale wire in electrical communication with the first electrode and in electrical communication with a first counter electrode, a second nanoscale wire in electrical communication with the first electrode and in electrical communication with a second counter electrode, a first reaction entity immobilized relative to the first nanoscale wire such that a binding event involving the first reaction entity is detectable by the nanoscale electrical sensor array device, and a second reaction entity immobilized relative to the second nanoscale wire such that a binding event involving the second reaction entity is detectable by the nanoscale electrical sensor array device independently of detection of a binding event involving the first reaction entity.

In another set of embodiments, the nanoscale electrical sensor array device includes a first nanoscale wire, a second nanoscale wire differing in composition from to the first nanoscale wire, a first reaction entity immobilized relative to the first nanoscale wire such that a binding event involving the first reaction entity is detectable by the nanoscale electrical sensor array device, and a second reaction entity immobilized relative to the second nanoscale wire such that a binding event involving the second reaction entity is detectable by the nanoscale electrical sensor array device independently of detection of a binding event involving the first reaction entity.

Still another aspect of the invention provides a densely-packed nanoscale electrical sensor array. In certain embodiments, the array comprises a first, generally elongate electrode, a first electrical lead in electronic communication with the first electrode, and a plurality of second electrodes, each spaced essentially equidistantly from the first electrode, and each in electrical communication with one of a plurality of separate, second electrical leads. The plurality of second electrodes may be disposed in a generally linear array essentially parallel to the first electrode. The array may also comprise a plurality of nanoscale wires, at least some of which span and are in electrical communication with the first electrode and one of the second electrodes, and a plurality of reaction entities positioned proximate the nanowires. In certain cases, the first and the plurality of second electrical leads define portions of an electrical circuit having the ability to sense a binding event involving a reaction entity, where each of the plurality of second electrical leads includes a portion nearest a second electrode that is both parallel to an adjacent second electrical lead and not perpendicular to the first electrode and the generally linear array of second electrodes.

The article, in another set of embodiments, includes a nanoscale wire, a nickel electrode annealed to the nanoscale wire, and a reaction entity immobilized relative to the nanoscale wire.

In another aspect, the present invention is directed to a method of making one or more of the embodiments described herein, for example, a sensing device comprising a nanoscale wire. In yet another aspect, the present invention is directed to a method of using one or more of the embodiments described herein, for example, a sensing device comprising a nanoscale wire. In still another aspect, the present invention is directed to a method of promoting one or more of the embodiments described herein, for example, a to sensing device comprising a nanoscale wire.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 1A-1C are schematic diagrams illustrating telomerase binding, in one embodiment of the invention;

FIGS. 2A-2C are schematic diagrams illustrating the determination of an enzyme using another embodiment of the invention;

FIGS. 3A-3D illustrate certain gangliosides, as used in certain embodiments of the invention;

FIGS. 10A-10B illustrate a nanoscale wire sensor, according to another embodiment of the invention;

FIGS. 11A-11B illustrate the concentration-dependent detection of various marker proteins, in another embodiment of the invention;

FIGS. 17A-17B illustrate the detection of certain viruses, according to another embodiment of the invention;

FIGS. 19A-19D illustrate the binding of certain viruses to a nanoscale wire, in yet another embodiment of the invention.

FIGS. 23A-23F illustrate the placement of antibodies on a nanoscale wire, in another embodiment of the invention;

FIGS. 24A-24I illustrate multiplexed detection of various analytes, according to other embodiments of the invention;

FIGS. 25A-25H illustrate the passivation of a metal electrode, according to still to another embodiment of the invention;

FIGS. 27A-27D illustrate current vs. voltage characteristics for certain embodiments of the invention;

BRIEF DESCRIPTION OF THE SEQUENCES

Figure 3A:
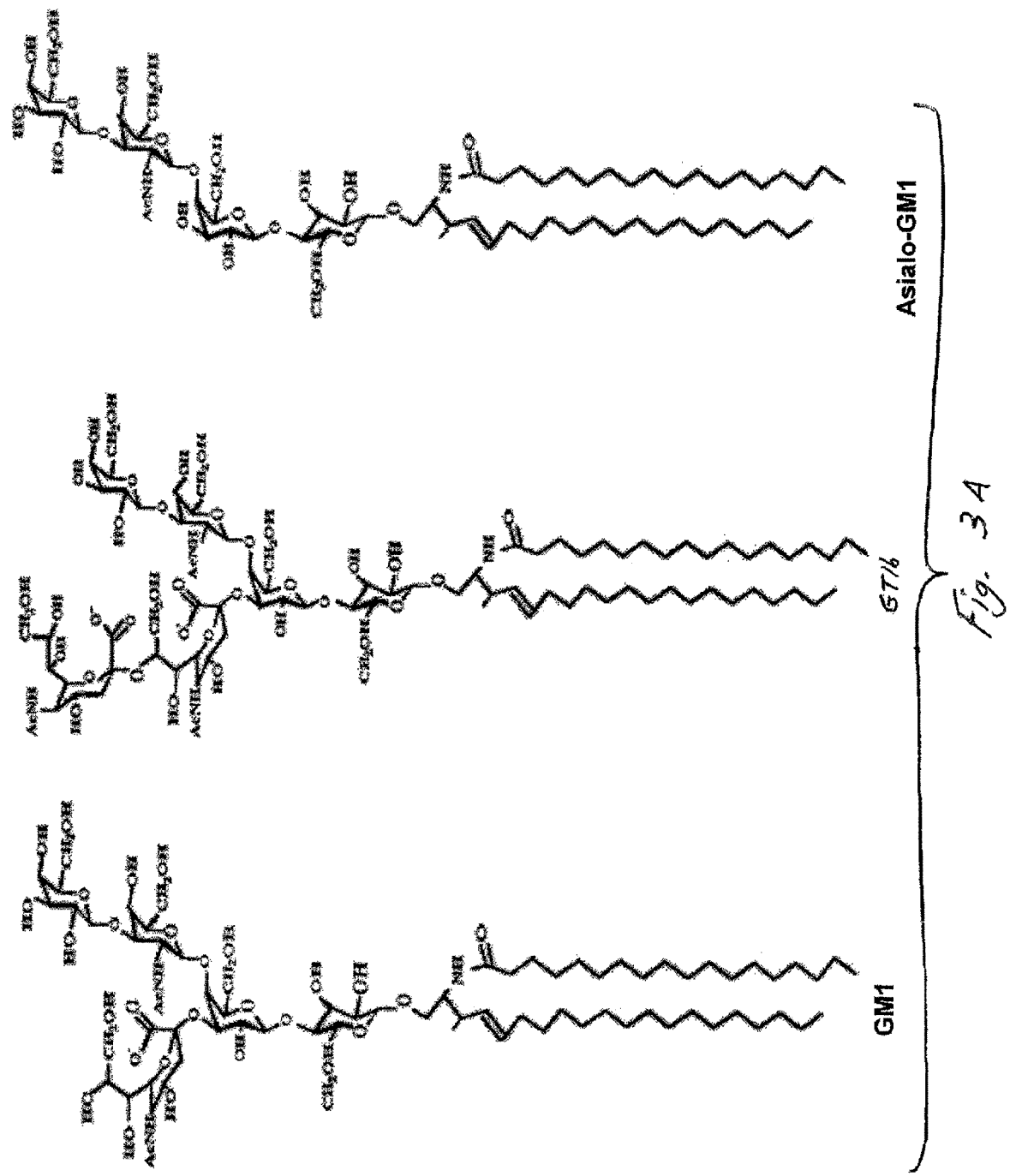

SEQ ID NO: 1 is TTAGGG, a telomeric repeat sequence;
SEQ ID NO: 2 is TTGGGG, a telomeric repeat sequence;
SEQ ID NO: 3 is TTGGGT, a telomeric repeat sequence;
SEQ ID NO: 4 is TTTTGGGG, a telomeric repeat sequence;
SEQ ID NO: 5 is TTAGGGT, a telomeric repeat sequence;
SEQ ID NO: 6 is TTAGGGC, a telomeric repeat sequence;
SEQ ID NO: 7 is TTTAGGG, a telomeric repeat sequence;
SEQ ID NO: 8 is TTTTAGGG, a telomeric repeat sequence;
SEQ ID NO: 9 is TTAGG, a telomeric repeat sequence;
SEQ ID NO: 10 is TTAGGC, a telomeric repeat sequence;
SEQ ID NO: 11 is AG, a telomeric repeat sequence;
SEQ ID NO: 12 is AGG, a telomeric repeat sequence;
SEQ ID NO: 13 is AGGG, a telomeric repeat sequence;
SEQ ID NO: 14 is AGGGG, a telomeric repeat sequence;
SEQ ID NO: 15 is AGGGGG, a telomeric repeat sequence;
SEQ ID NO: 16 is AGGGGGG, a telomeric repeat sequence;
SEQ ID NO: 17 is AGGGGGGG, a telomeric repeat sequence;
SEQ ID NO: 18 is AGGGGGGGG, a telomeric repeat sequence;
SEQ ID NO: 19 is TTACG, a telomeric repeat sequence;
SEQ ID NO: 20 is TTACGG, a telomeric repeat sequence;
SEQ ID NO: 21 is TTACGGG, a telomeric repeat sequence;

SEQ ID NO: 22 is TTACGGGG, a telomeric repeat sequence;
SEQ ID NO: 23 is TTACGGGGG, a telomeric repeat sequence;
SEQ ID NO: 24 is TTACGGGGGG, a telomeric repeat sequence;
SEQ ID NO: 25 is TTACGGGGGGG, a telomeric repeat sequence;
SEQ ID NO: 26 is TTACGGGGGGGG, a telomeric repeat sequence;
SEQ ID NO: 27 is TTACAG, a telomeric repeat sequence;
SEQ ID NO: 28 is TTACAGG, a telomeric repeat sequence;
SEQ ID NO: 29 is TTACAGGG, a telomeric repeat sequence;
SEQ ID NO: 30 is TTACAGGGG, a telomeric repeat sequence;
SEQ ID NO: 31 is TTACAGGGGG, a telomeric repeat sequence;
SEQ ID NO: 32 is TTACAGGGGGG, a telomeric repeat sequence;
SEQ ID NO: 33 is TTACAGGGGGGG, a telomeric repeat sequence;
SEQ ID NO: 34 is TTACAGGGGGGGG, a telomeric repeat sequence;
SEQ ID NO: 35 is TTACCG, a telomeric repeat sequence;
SEQ ID NO: 36 is TTACCGG, a telomeric repeat sequence;
SEQ ID NO: 37 is TTACCGGG, a telomeric repeat sequence;
SEQ ID NO: 38 is TTACCGGGG, a telomeric repeat sequence;
SEQ ID NO: 39 is TTACCGGGGG, a telomeric repeat sequence;
SEQ ID NO: 40 is TTACCGGGGGG, a telomeric repeat sequence;
SEQ ID NO: 41 is TTACCGGGGGGG, a telomeric repeat sequence;
SEQ ID NO: 42 is TTACCGGGGGGGG, a telomeric repeat sequence;
SEQ ID NO: 43 is TTACACG, a telomeric repeat sequence;
SEQ ID NO: 44 is TTACACGG, a telomeric repeat sequence;
SEQ ID NO: 45 is TTACACGGG, a telomeric repeat sequence;
SEQ ID NO: 46 is TTACACGGGG, a telomeric repeat sequence;
SEQ ID NO: 47 is TTACACGGGGG, a telomeric repeat sequence;
SEQ ID NO: 48 is TTACACGGGGGG, a telomeric repeat sequence;
SEQ ID NO: 49 is TTACACGGGGGGG, a telomeric repeat sequence;
SEQ ID NO: 50 is TTACACGGGGGGGG, a telomeric repeat sequence;
SEQ ID NO: 51 is TGTGGGTGTGGTG, a telomeric repeat sequence;
SEQ ID NO: 52 is GGGGTCTGGGTGCTG, a telomeric repeat sequence;
SEQ ID NO: 53 is GGTGTACGGATGTCTAACTTCTT, a telomeric repeat sequence;
SEQ ID NO: 54 is GGTGTACGGATGTCACGATCATT, a telomeric repeat sequence;
SEQ ID NO: 55 is GGTGTAAGGATGTCACGATCATT, a telomeric repeat sequence;
SEQ ID NO: 56 is GGTGTACGGATGCAGACTCGCTT, a telomeric repeat sequence;
SEQ ID NO: 57 is GGTGTAC, a telomeric repeat sequence;
SEQ ID NO: 58 is GGTGTACGGATTTGATTAGTTATGT, a telomeric repeat sequence;
SEQ ID NO: 59 is GGTGTACGGATTTGATTAGGTATGT, a telomeric repeat sequence; and
SEQ ID NO: 60 is $H_2N$—$(CH_2)_6$-TTTTTTAATCCGTCGAGCAGAGTT, an amino-modified oligonucleotide.

DETAILED DESCRIPTION

Various aspects of the present invention generally relate to nanoscale wire devices and methods for use in determining analytes suspected to be present in a sample, and systems and methods of immobilizing entities such as reaction entities relative to nanoscale wires. In one aspect, a nucleic acid, such as DNA, may be immobilized relative to a nanoscale wire, and in some cases, grown from the nanoscale wire. In certain embodiments, the nucleic acid may interact with entities such as other nucleic acids, proteins, etc., and in some cases, such interactions may be reversible. As an example, an enzyme such as a telomerase may be allowed to bind to DNA immobilized relative to a nanoscale wire. The telomerase may extend the length of the DNA, for instance, by reaction with free deoxynucleotide triphosphates in solution; additionally, various properties of the nucleic acid may be determined, for example, using electric field interactions between the nucleic acid and the nanoscale wire. In another aspect, the invention provides systems and methods for attaching entities such as nucleic acids, receptors such as gangliosides, or surfactants to a nanoscale wire, for example, using aldehyde-producing reactions or hydrophobic interactions. In some aspects, certain systems and methods of the present invention may be used to determine an analyte suspected to be present in a sample, for example, a toxin, a virus, or a small molecule. Systems and methods of using such nanoscale wires are disclosed in other aspects of the to invention, for example, within a microarray. Still other aspects of the invention include assays, sensors, kits, and/or other devices that include such nanoscale wires, methods of making and/or using functionalized nanoscale wires (for example, in drug screening or high-throughput screening), and the like.

One embodiment of the present invention allows for the detection and/or quantification (i.e., determination) of a telomerase enzyme, for example, in a cancer test or a drug screen. In this embodiment, a nanoscale wire can have one or more nucleic acids covalently bonded thereon (or otherwise immobilized relative to the nanoscale wire), where the nucleic acid is chosen such that the telomerase will bind to the nucleic acid. For example, the nucleic acid may be substantially complementary to the nucleic acid component of the telomerase enzyme (or a portion thereof). Binding of the telomerase to the nucleic acid may alter the conductivity of the nanoscale wire. For instance, if the telomerase is charged, the immobilization of a charged entity relative to the nanoscale wire may alter the conductivity (or other electronic property) of the nanoscale wire, which can then be detected and recorded. Thus, by determining the conductivity of the nanoscale wire, the presence and/or concentration of the telomerase within a sample can be determined.

In another embodiment of the present invention, a toxin, such as cholera toxin or botulinum toxin, may be determined, for example, in an environmental study or a food test. In this embodiment, a nanoscale wire may have one or more gangliosides immobilized relative thereto. For instance, a hydrophobic interaction between the hydrophobic portion of the ganglioside and a hydrophobic monolayer present on the surface of the nanoscale wire can be used to immobilize the ganglioside relative to the nanoscale wire. The ganglioside is chosen to specifically bind the toxin. If the toxin is charged, upon binding, the toxin may alter the conductivity (or other electronic property) of the nanoscale wire, which can then be detected and recorded. Thus, by determining the conductivity of the nanoscale wire, the presence and/or concentration of the toxin in a sample can be determined.

However, it should be noted that the present invention is not limited to the above-described embodiments. In general, various aspects of the present invention provide a sensing element comprising a nanoscale wire able to interact with one or more analytes. For example, the nanoscale wire may be used to determine an analyte as part of an assay for determining or diagnosing cancer or other medical conditions (e.g., by determining a suitable marker, for example, a hormone, an enzyme, a peptide, a virus, etc., and diagnosing the cancer or other medical condition based on the determination of the marker), for determining drugs (e.g., as part of a drug assay or a drug screen, for instance, to identify a drug able to treat a medical condition such as cancer or aging), for determining toxins or other environmental agents (e.g., by determining binding of the toxin to a receptor), or the like.

The nanoscale wire may have a reaction entity able to interact with an analyte of interest. Nanoscale sensing elements of the invention may be used, for example, to determine pH or metal ions, viruses, proteins or enzymes (e.g., a telomerase or other enzymes able to bind a nucleic acid, as further described below), nucleic acids (e.g. DNA, RNA, PNA, etc.), drugs, sugars, carbohydrates, a toxin (e.g., a harmful chemical, such as a chemical produced by a living organism that is harmful to other organisms), small molecules (e.g., having molecular weights of less than about 2000 Da, less than about 1500 Da, or less than about 1000 Da), or other analytes of interest, as further described herein. The analyte may be charged, or uncharged in some embodiments. In certain embodiments, single entities may be determined, for example, a single virus, a single protein, a single enzyme, a single nucleic acid molecule, a single drug molecule, a single carbohydrate molecule, etc. In some cases, the sensing element includes a detector constructed and arranged to determine a change in a property of the nanoscale wire, for example, a change in light emission, a change in stress or shape, or a change in an electrical property of the nanoscale wire, such as voltage, current, conductivity, resistivity, inductance, impedance, electrical change, an electromagnetic change, etc. In one set of embodiments, at least a portion of the nanoscale wire is addressable by a sample (e.g., a gas or liquid sample) containing, or at least suspected of containing, the analyte. The term "addressable," e.g., by a fluid, is defined as the ability of the fluid to be positioned relative to the nanoscale wire so that the analytes suspected of being in the fluid are able to interact with the nanoscale wire. The fluid may be proximate to or in contact with the nanoscale wire. In some embodiments, the fluid may be directed to the nanoscale wire through the use of a microfluidic channel, as further described below.

As used herein, the term "reaction entity" refers to any entity that can interact with an analyte in such a manner as to cause a detectable change in a property of a to nanoscale wire. The reaction entity may comprise a binding partner to which the analyte binds. The reaction entity, when a binding partner, can comprise a specific binding partner of the analyte. In some cases, the reaction entity can form a coating on the nanoscale wire. Non-limiting examples of reaction entities include a nucleic acid (e.g., DNA or RNA), an antibody, a sugar or a carbohydrate, a protein or an enzyme, a ganglioside or a surfactant, etc., e.g., as discussed herein.

In one set of embodiments, a reaction entity associated with the nanoscale wire is able to interact with an analyte. The reaction entity, as "associated" with or "immobilized" relative to the nanoscale wire, may be positioned in relation to the nanoscale wire (e.g., in close proximity or in contact) such that the analyte can be determined by determining a change in a characteristic or property of the nanoscale wire. Interaction of the analyte with the reaction entity may cause a detectable change or modulation in a property of the nanoscale wire, for example, through electrical coupling with the reaction entity. The term "electrically coupled" or "electrocoupling," when used with reference to a nanoscale wire and an analyte, or other moiety such as a reaction entity, refers to an association between any of the analyte, other moiety, and the nanoscale wire such that electrons can move from one to the other, or in which a change in an electrical characteristic of one can be determined by the other. This can include electron flow between these entities, or a change in a state of charge, oxidation, or the like, that can be determined by the nanoscale wire. As examples, electrical coupling or immobilization can include direct covalent linkage between the analyte or other moiety and the nanoscale wire, indirect covalent coupling (for instance, via a linker, and/or a plurality of linkers, e.g., serially), direct or indirect ionic bonding between the analyte (or other moiety) and the nanoscale wire, direct or indirect bonding of both the analyte and the nanoscale wire to a particle (i.e., the particle acts as a linker between the analyte and the nanoscale wire), direct or indirect bonding of both the analyte and the nanoscale wire to a common surface (i.e., the surface acts as a linker), or other types of bonding or interactions (e.g. hydrophobic interactions or hydrogen bonding). In some cases, no actual covalent bonding is required; for example, the analyte or other moiety may simply be contacted with the nanoscale wire surface. There also need not necessarily be any contact between the nanoscale wire and the analyte or other moiety where the nanoscale wire is sufficiently close to the analyte to permit electron tunneling between the analyte to and the nanoscale wire.

Thus, the reaction entity may be positioned relative to the nanoscale wire to cause a detectable change in the nanoscale wire. In some cases, the reaction entity may be positioned within about 100 nm of the nanoscale wire, within about 75 nm of the nanoscale wire, within about 50 nm of the nanoscale wire, within about 20 nm of the nanoscale wire, within about 15 nm of the nanoscale wire, or within about 10 nm of the nanoscale wire. The actual proximity can be determined by those of ordinary skill in the art. In some cases, the reaction entity is positioned less than about 5 nm from the nanoscale wire. In other cases, the reaction entity is positioned within about 4 nm, within about 3 nm, within about 2 nm, or within about 1 nm of the nanoscale wire.

In some embodiments, the reaction entity is fastened to or directly bonded (e.g., covalently) to the nanoscale wire, e.g., as further described herein. However, in other embodiments, the reaction entity is not directly bonded to the nanoscale wire, but is otherwise immobilized relative to the nanoscale wire, i.e., the reaction entity is indirectly immobilized relative to the nanoscale wire. For instance, the reaction entity may be attached to the nanoscale wire through a linker, i.e., a species (or plurality of species) to which the reaction entity and the nanoscale wire are each immobilized relative thereto, e.g., covalently or non-covalently bound to. As an example, a linker may be directly bonded to the nanoscale wire, and the reaction entity may be directly bonded to the linker, or the reaction entity may not be directly bonded to the linker, but immobilized relative to the linker, e.g., through the use of non-covalent bonds such as hydrogen bonding (e.g., as in complementary nucleic acid-nucleic acid interactions), hydrophobic interactions (e.g., between hydrocarbon chains), entropic interactions, or the like. The linker may or may not be directly bonded (e.g., covalently) to the nanoscale wire.

As used herein, a first portion of a nucleic acid is "complementary" to a second portion of a nucleic acid if the nucleotides of the first portion and the nucleotides of the second portion are complementary (i.e., A to T or U, C to G, etc.) and/or the portions are at least 75% complementary (i.e., at least 75% of the nucleotides of the first and second portions of the nucleic acids are complementary). In some cases, the nucleic acid portions are at least 80%, at least 85%, at least 90%, at least 95%, at least 96%, at least 97%, at least 98%, or at least 99% complementary. In some embodiments, the first and to second portions have a maximum of 0, 1, 2, 3, 4, 5, 6, 7, 8, 9, or 10 nucleotide mismatches. The complementary portions of the nucleotides may be at least 5 nucleotides long, and in some cases, at least 7 nucleotides long, at least about 10 nucleotides long, at least about 12 nucleotides long, at least about 15 nucleotides long, at least about 20 nucleotides long, at least about 25 nucleotides long, or at least about 50 nucleotides long.

As one particular, non-limiting example, an enzyme able to bind a nucleic acid can be bound to a nucleic acid covalently bound to a nanoscale wire, or the enzyme may be bound to a first nucleic acid that is not covalently bound to the nanoscale wire, but is otherwise immobilized relative to the nanoscale wire, e.g., by complementary binding to a second nucleic acid that is covalently bound to the nanoscale wire, etc. In certain embodiments, the nucleic acid covalently bound to the nanoscale wire can be relatively short and/or have a relatively specific sequence that allows only a certain kind of interaction. For instance, the nucleic acid that is covalently bound to the nanoscale wire may have less than 5, less than 10, less than 15, or less than 20 nucleotides.

As another particular, non-limiting example, a reaction entity having a hydrophobic moiety, such as a ganglioside or a surfactant, may be not directly bound to a nanoscale wire, but may be immobilized relative to the nanoscale wire via a hydrophobic interaction between the hydrophobic portion of the reaction entity and a portion of a nanoscale wire that is hydrophobic. For instance, the hydrophobic portion of the nanoscale wire may be created due to the presence of a hydrophobic layer (e.g., of hydrocarbon chains) on the surface of the nanoscale wire, e.g., as described in more detail below.

Indirectly immobilizing a reaction entity relative to a nanoscale wire is useful in certain embodiments of the invention. For example, if a reaction entity is immobilized relative to a nanoscale wire without the use of covalent bonds, the reaction entity may be replaced with a second reaction entity (which may be of the same type or different), without breaking a covalent bond between the reaction entity and the nanoscale wire. This allows, for instance, simpler chemical reactions, less energetic costs in replacing the reaction entity, or reusability of the nanoscale wire. As a non-limiting example, a reaction entity, such as a nucleic acid or a protein, immobilized relative to a nanoscale wire, e.g., through complementary nucleic acid-nucleic acid interactions, can be replaced with a second nucleic acid through the use of a melting solution that dissociates the nucleic acid-nucleic acid interactions (e.g., a urea solution, a formamide solution, etc.) and/or by heating the nucleic acids to induce dissociation. Such dissociation can be followed by, or simultaneously performed with, exposure of the nanoscale wire to the second reaction entity.

A high degree of specificity is also possible in some embodiments of the invention, for example, in embodiments where the reaction entity specifically binds to one or more particular analytes of interest, but does not bind to other molecules, e.g., molecules similar to the analytes of interest (such as other proteins or enzymes if the analyte of interest is a protein or an enzyme). For example, a reaction entity may specifically bind a first analyte, such as a toxin, a virus, or an enzyme, but is not able to specifically bind to other toxins or enzymes. The binding (or other interaction) of the reaction entity to a single molecule of the analyte of interest may be determinable in some cases, regardless of the concentrations or amounts of other molecules that are similar to the analytes of interest that are present in the sample, e.g., due to specificity between the reaction entity and the analyte of interest. Thus, in certain embodiments of the invention, an analyte of interest may be determined in a sample, such as in solution, even though the total concentration of other molecules (e.g., other solutes or solvents, molecules similar to the analyte of interest, carrier fluids, impurities, etc.) is much higher than the concentration of the analyte of interest. For example, an analyte of interest may be determined from a sample, although the total concentration of other molecules may be at least about 1000 times higher, at least about 3000 times higher, at least about $10^5$ times higher, at least about $3 \times 10^5$ times higher, at least about $10^6$ times higher, etc. than the analyte of interest.

In one set of embodiments, the reaction entity is able to bind a nucleic acid synthesis enzyme, i.e., an enzyme able to synthesize a nucleic acid such as DNA or RNA. The nucleic acid synthesis enzyme, after binding, may be allowed to synthesize (e.g., de novo) and/or extend a nucleic acid, for example, a nucleic acid immobilized relative to a nanoscale wire as part of a reaction entity. The reaction entity may be, for instance, an antibody able to specifically bind at least a portion of the nucleic acid synthesis enzyme, a nucleic acid that includes a sequence that is recognized by the enzyme (e.g., the nucleic acid may be recognized by an active site of the enzyme, the enzyme may contain a nucleic acid that is at least partially complementary to the nucleic acid of the reaction entity, or the like), etc. The nucleic acid synthesis enzyme that the reaction entity is able to bind may be, for example, a reverse transcriptase, a DNA polymerase, an RNA polymerase, or a telomerase, and the reaction entity immobilized relative to the nanoscale wire may be a nucleic acid that the nucleic acid synthesis enzyme is able to bind to. Non-limiting examples of DNA polymerases include Pol I, Pol II, Pol III, Pol alpha, Pol beta, Pol gamma, Pol delta, Pol epsilon, Pol zeta, or the like. Non-limiting examples of RNA polymerase include RNA polymerase I, RNA polymerase II, RNA polymerase III, etc.

In some cases, the reaction entity is able to bind a telomerase, i.e., the reaction entity is a telomerase-recognition entity, that is, an entity able to specifically bind a telomerase enzyme, or at least a portion thereof. A telomerase is an enzyme able to synthesize a telomeric repeat sequence. A telomere is generally a region of highly repetitive DNA located at or near the end of a DNA strand that is involved in DNA replication, and the repeated DNA is the telomeric repeat sequence. For example, in humans and in many other vertebrates, as well as certain fungi, molds, or protazoas, the telomere repeat sequence is a repeating sequence of TTAGGG (SEQ ID NO: 1), which may be, for example, between 3 and 20 kilobases in length in normal human chromosomes. Telomere sequences can vary from species to species, but are generally GC-rich. Telomeres have also been linked to aging and to cancer. Thus, according to some embodiments of the invention, determination of a telomere and/or a telomerase may be used to diagnose cancer and/or aging processes within a subject.

In one embodiment, the telomerase-recognition entity is a nucleic acid that includes a sequence that is at least partially complementary to a nucleic acid that is part of a telomerase enzyme. For example, the nucleic acid may include sequence may be at least about 80% complementary, at least about 85% complementary, at least about 90% complementary, at least about 95% complementary, or 100% complementary to the telomeric repeat sequence to be determined.

Additional examples of telomeric repeat sequences include, but are not limited to, TTGGGG (SEQ ID NO: 2), TTGGGT (SEQ ID NO: 3), TTTTGGGG (SEQ ID NO: 4) (e.g., in certain ciliated protozoa); TTAGGGT (SEQ ID NO: 5), TTAGGGC (SEQ ID to NO: 6) (e.g., in certain apicomplexan protazoa); TTTAGGG (SEQ ID NO: 7) (e.g., in certain plants); TTTTAGGG (SEQ ID NO: 8) (e.g., in green algae); TTAGG (SEQ ID NO: 9) (e.g., in certain insects); TTAGGC (SEQ ID NO: 10) (e.g., in certain roundworms); AG (SEQ ID NO: 11), AGG (SEQ ID NO: 12), AGGG (SEQ ID NO: 13), AGGGG (SEQ ID NO: 14), AGGGGG (SEQ ID NO: 15), AGGGGGG (SEQ ID NO: 16), AGGGGGGG (SEQ ID NO: 17), AGGGGGGGG (SEQ ID NO: 18) (e.g., in certain slime molds); TTACG (SEQ ID NO: 19); TTACGG (SEQ ID NO: 20); TTACGGG (SEQ ID NO: 21); TTACGGGG (SEQ ID NO: 22); TTACGGGGG (SEQ ID NO: 23); TTACGGGGGG (SEQ ID NO: 24); TTACGGGGGGG (SEQ ID NO: 25); TTACGGGGGGGG (SEQ ID NO: 26); TTACAG (SEQ ID NO: 27); TTACAGG (SEQ ID NO: 28); TTACAGGG (SEQ ID NO: 29); TTACAGGGG (SEQ ID NO: 30); TTACAGGGGG (SEQ ID NO: 31); TTACAGGGGGG (SEQ ID NO: 32); TTACAGGGGGGG (SEQ ID NO: 33); TTACAGGGGGGGG (SEQ ID NO: 34); TTACCG (SEQ ID NO: 35); TTACCGG (SEQ ID NO: 36); TTACCGGG (SEQ ID NO: 37); TTACCGGGG (SEQ ID NO: 38); TTACCGGGGG (SEQ ID NO: 39); TTACCGGGGGG (SEQ ID NO: 40); TTACCGGGGGGG (SEQ ID NO: 41); TTACCGGGGGGGG (SEQ ID NO: 42); TTACACG (SEQ ID NO: 43); TTACACGG (SEQ ID NO: 44); TTACACGGG (SEQ ID NO: 45); TTACACGGGG (SEQ ID NO: 46); TTACACGGGGG (SEQ ID NO: 47); TTACACGGGGGG (SEQ ID NO: 48); TTACACGGGGGGG (SEQ ID NO: 49); TTACACGGGGGGGG (SEQ ID NO: 50) (e.g., in certain yeasts); or TGTGGGTGTGGTG (SEQ ID NO: 51), GGGGTCTGGGTGCTG (SEQ ID NO: 52), GGTGTACGGATGTCTAACTTCTT (SEQ ID NO: 53), GGTGTACGGATGTCACGATCATT (SEQ ID NO: 54), GGTGTAAGGATGTCACGATCATT (SEQ ID NO: 55), GGTGTACGGATGCAGACTCGCTT (SEQ ID NO: 56), GGTGTAC (SEQ ID NO: 57), GGTGTACGGATTTGATTAGTTATGT (SEQ ID NO: 58), or GGTGTACGGATTTGATTAGGTATGT (SEQ ID NO: 59) (e.g., in certain yeasts). Those of ordinary skill in the art will know of other telomeric repeat sequences, depending on the specific organism being studied.

In some embodiments, binding of a nucleic acid synthesis enzyme alters a property of the nanoscale wire, for example, the conductivity of the nanoscale wire, e.g., if the enzyme is charged. A determination of the conductivity or other property of the nanoscale wire and/or a change in such conductivity or other property may thus allow determination of the immobilization of the enzyme relative to the nanoscale wire. If the enzyme binds a nucleic acid immobilized relative to the nanoscale wire, in certain cases, additional properties of the enzyme and/or the nucleic acid may be determined. For example, the enzyme may be immobilized at a certain distance away from the nanoscale wire, which is at least partially dependent on the length of the nucleic acid. Thus, determination of the conductivity or other property of the nanoscale wire may allow a determination of the length of the nucleic acid and/or the number of nucleotides within the nucleic acid. In some embodiments, the enzyme is allowed to synthesize (e.g., de novo) and/or extend the nucleic acid, and such nucleic acid synthesis may be monitored by determining the conductivity or other property of the nanoscale wire.

As an example, as is shown in FIG. 1A, a nanoscale wire 230, disposed between electrodes 231, 232, has several nucleic acids 233 directly bonded thereto. In FIG. 1B, the nanoscale wire is exposed to a sample containing a nucleic acid synthesis enzyme 235 (e.g., a telomerase), and at least some of the nucleic acids are complementary to nucleic acids found within enzyme 235, allowing binding of the enzyme to those nucleic acids. The conductivity or other properties of the nanoscale wire in FIG. 1B may be altered by immobilization of the enzyme relative to the nanoscale wire, and such alterations may be determined, e.g., by electrical measurements between electrodes 231 and 232. In FIG. 1C, the enzymes are induced to perform nucleic acid synthesis on the nucleic acid covalently bound to the nanoscale wire, and deoxynucleotide triphosphates ("dNTPs") 236 are provided and are incorporated into the growing nucleic acid strand. Such nucleic acid synthesis may be monitored, for example, by determining changes in conductivity or other properties of the nanoscale wires. The enzymes may also be removed from the nanoscale wire.

It should be noted that direct covalent bonding of the nucleic acid reaction entity to the nanoscale wire is not necessarily a requirement. An example of indirect immobilization of the nucleic acid reaction entity is shown in FIG. 2. In FIG. 2A, a nanoscale wire 240, disposed between electrodes 241, 242, has several first nucleic acid 243 directly bonded thereto (which may all be identical, or some may be different). These nucleic acids are hybridized in FIG. 2B to a second nucleic acid 244. The second nucleic acid contains a first portion having a sequence substantially complementary to a to first nucleic acid, and a second portion having a sequence substantially complementary to a portion of an enzyme of interest (e.g., a telomerase). In FIG. 2C, the nanoscale wire is exposed to a sample comprising an enzyme 245 (e.g., a telomerase), and at least some of the nucleic acids are complementary to nucleic acids found within enzyme 235, allowing binding of the enzyme to those nucleic acids. Optionally, the nanoscale wire may also be exposed to deoxynucleotide triphosphates ("dNTPs") 246, and enzyme 235 may be induced to perform nucleic acid synthesis. By dehybridizing the second nucleic acid from the first nucleic acid (e.g., using a "melting solution" such as a urea solution), the second nucleic acids (and any enzymes that may be bound thereto) may be removed (e.g., to be discarded, or for further analyses), and the nanoscale wire with the first nucleic acid may also be reused in some cases.

Such reactions may also be modified or altered using techniques known to those of ordinary skill in the art. For example, additional species may be introduced, which can compete with binding of the enzyme to the nucleic acids, e.g., competitively, uncompetitively, or noncompetitively. As an example, an inhibitor of nucleic acid synthesis, e.g., a nucleotide analog such as azido deoxythymidine triphosphate may be used to partially or totally inhibit nucleic acid synthesis. Such techniques may be used, for example, to identify or screen for agents able to treat cancer or aging (e.g., agents able to inhibit telomerase activity within cells), to study nucleic acid synthesis (e.g., by promoting or inhibiting various chemical reactions within the nucleic acid synthesis pathway), etc.

In another set of embodiments, the reaction entity is able to bind a toxin or a small molecule (e.g., a molecule having molecular weights of less than about 2000 Da, less than about 1500 Da, or less than about 1000 Da). Binding of the toxin or small molecule may alter a property of the nanoscale wire, for example, the conductivity of the nanoscale wire, e.g., if the toxin or other small molecule is charged. A determination of the conductivity or other property of the nanoscale wire and/or a change in such conductivity or other property may allow determination of the toxin or other small molecule, e.g., detection and/or quantification.

The reaction entity may be, for example, an antibody, an aptamer, or a receptor for the toxin or other small molecule, e.g., a ganglioside. The reaction entity may be directly covalently bound to the nanoscale wire, or the reaction entity may be indirectly immobilized relative to the nanoscale wire, e.g., through the use of non-covalent bonds such as hydrogen bonding, hydrophobic interactions, etc. For example, if the reaction entity includes a hydrophobic region, and at least a portion of the surface of a nanoscale wire includes one or more layers of molecules covalently bonded thereto, at least some of which are hydrophobic, the hydrophobic interactions between the hydrophobic portion of the entity and the one or more layers may cause the entity to be immobilized relative to the nanoscale wire, as discussed in more detail herein.

In some embodiments, the reaction entity is a ganglioside, a glycosphingolipid, a phospholipid, a surfactant, etc., i.e., a molecule having both a lipid region and a charged region, for example, a carbohydrate or a sugar region. Such molecules can be found in the plasma (outer) membrane of a cell. Non-limiting examples of gangliosides include GM1, GD1b, and asialo-GM1 (FIG. 3A). Other examples include GM1a, GM1b, GM2, GM3, GD1a, GD1b, GD2, GD3, GT1a, GT1b, GT2, GT3, GT4, GA1, GA2, GA3, GA4, GQ1a, GQ1b, GQ1c, GQ3, GP1b, GP1c, GP2, GP3, GP4, GP5, GP6, sulfatide, SPG, SGPG, etc.

The lipid region of such reaction entities may include one or more relatively long hydrocarbon chains (e.g., containing carbon and hydrogen atoms), which may confer hydrophobic properties to the reaction entities. In some cases, the hydrocarbon chains are straight-chain saturated alkyls, e.g., as is shown in FIG. 3A. However, in other cases, one or more hydrocarbon chains may be unsaturated (e.g., containing one or more double and/or triple carbon-carbon bonds), and/or include one or more heteroatoms (e.g., oxygen or nitrogen atoms). In some embodiments, one or more hydrocarbon chains may be branched.

In some cases, the reaction entity is able to interact with a toxin or a small molecule, and in some instances, the interaction is a specific interaction. Thus, for example, the toxin may be a toxin that has a specific interaction with a ganglioside or glycosphingolipid, i.e., the toxin has a higher affinity to the particular ganglioside or glycosphingolipid than to any other ganglioside or glycosphingolipid. For example, cholera toxin (CT) may specifically interact with GM1, botulinum toxin (BT) may specifically interact with GT1b, etc. Those of ordinary skill in the art will know of other toxins that interact with various gangliosides or glycosphingolipids.

Thus, another set of embodiments of the present invention generally relates to to nanoscale wires having one or more layers of molecules immobilized relative to the nanoscale wire, for example, covalently. For instance, all, or a portion, of the surface of the nanoscale wire may comprise a monolayer of molecules covalently bonded thereon (for example, a portion of the nanoscale wire may be blocked or shielded, prior to attachment of the monolayer of the surface). Such a monolayer may be formed, for instance, of molecules each having a functional group that selectively attaches to the surface, and in some cases, the remainder of each molecule can interact with neighboring molecules in the monolayer (e.g., through hydrophobic interactions, charged interactions, or the like). In some cases, the monolayer is a self-assembled monolayer.

In other embodiments, however, more than one layer of molecules may be covalently immobilized relative to the nanoscale wire. For instance, all, or a portion of, a nanoscale wire may comprise a first layer of molecules covalently bonded to the nanoscale wire, a second layer of molecules covalently bonded to at least a portion of the first layer of molecules. Optionally, additional layers may be present, for example, a third layer of molecules covalently bonded to at least a portion of the second layer of molecules, a fourth layer of molecules covalently bonded to at least a portion of the third layer of molecules, etc. The compositions of each layer of molecules may be the same or different (for example, having different molecule(s) and/or different ratios of molecules, etc.), and each layer may have properties that are the same or different. For instance, one layer may be relatively hydrophilic while another layer may be relatively hydrophobic, etc. In some cases, one or more of the layers may be cross-linked In certain embodiments, the thickness and/or number of layers on the surface of the nanoscale wire may be controlled, for example, by controlling the reaction time between the molecules forming the layer(s) and the surface of the nanoscale wire. Thus, as a specific non-limiting example, a thicker monolayer of an aldehyde silane (e.g., aldehyde propyltrimethoxysilane) may be formed on the surface of a nanoscale wire by exposing the nanoscale wire to a solution comprising an aldehyde, for example, aldehyde propyltrimethoxysilane, for a longer period of time, e.g., as further discussed below. For example, the reaction may be controlled such that the thickness is only a few atomic layers thick, and/or a few molecules or layers thick, or the thickness of the layer may be controlled such that the thickness of the layer is less than about 20 nm, less than about 15 nm, less than about 10 nm, less than about 9 nm, less than about 8 nm, less than about 7 nm, less than about 6 nm, less than about 5 nm, less than about 4 nm, less than about 3 nm, less than about 2 nm, or less than about 1 nm In some cases, the reaction and/or the thickness of the layer may be monitored. The thicknesses may be controlled in some embodiments by controlling parameters such as the exposure time of the precursor to the nanoscale wire, the reaction rate, the concentration of precursor in solution, etc. In some cases, nanoscale wires subjected to such control may be removed and examined (during and/or after an experiment), using techniques such as atomic force microscopy or the like, to determine the thickness of the layer formed on the nanoscale wire. By using such monitoring, preselected reaction conditions may be determined wherein a nanoscale wire, exposed to a precursor under such conditions, will form a layer of the precursor on the surface of the nanoscale wire of a certain known thickness. Thus, the preselected conditions are one or a set of conditions specifically developed in conjunction with a measurement of the thickness of a layer of precursor on the nanoscale wire.

In another aspect, the present invention generally relates to the attachment of reaction entities, such as biological entities, to the surfaces of nanoscale wires, in some cases by using covalent bonding. The entity is thus immobilized with respect to the surface of the nanoscale wire. In some embodiments, a linker is used to covalently immobilize the entity with respect to the nanoscale wire. For example, a nanoscale wire may have a core, and optionally a shell, and a linker may covalently immobilize the entity with respect to the nanoscale wire. In some cases, the entity may be covalently immobilized with respect to the surface of the nanoscale wire at relatively short distances, depending on the size of the linker and/or the precursors thereof. For instance, the entity may be immobilized at a distance of less than about 20 nm, less than about 15 nm, less than about 10 nm, less than about 9 nm, less than about 8 nm, less than about 7 nm, less than about 6 nm, less than about 5 nm, less than about 4 nm, less than about 3 nm, less than about 2 nm, or less than about 1 nm from the surface of the nanoscale wire and/or a border of the nanoscale wire, for example, a border of the core of a nanoscale wire. In certain instances, the border is an outermost border of the core of the nanoscale wire. In some cases, the proximity of the entity may control or otherwise affect electronic and/or other properties of the nanoscale wire, for example, the conductivity of the nanoscale wire.

In some cases, the linker and/or precursor thereof may form a layer, such as a monolayer or other layer of a controlled thickness, that is attached to the surface of the nanoscale wire and/or immobilized relative to the nanoscale wire, for example, covalently. For example, precursor linker molecules may be attached to the surface of the nanoscale, e.g., as described herein, and an entity then attached to the precursor molecules, thereby forming an entity covalently attached to the surface of the nanoscale wire via a linker. In one embodiment, the precursor itself is called a linker once the entity is attached covalently to it. In another embodiment, the precursor of a linker may undergo chemical modification or reaction, prior to attachment of the entity. In some cases, the linker includes at least a first region that is bound to the surface of the nanoscale wire and/or another molecule that is immobilized relative to the surface of the nanoscale wire, and a second region that is bound to an entity such as a biological entity.

Non-limiting examples of techniques for preparing a layer of linkers and/or precursors thereof include those described herein. For example, the thicknesses may be controlled in some embodiments by controlling parameters such as the exposure time of the precursor to the nanoscale wire, and the thickness may be monitored using techniques such as atomic force microscopy or the like, prior to or after attachment of the entity to the precursor on the nanoscale wire. Thus, one embodiment provides for the attaching, to the surface of a nanoscale wire, of a precursor of a molecule such as a linker in a layer, and the determination of the thickness of the precursor on the nanoscale wire. Optionally, an entity may be attached to at least a portion of the layer of the nanoscale wire. By using such techniques, the distance between the entity and the nanoscale wire may be controlled. For example, the layer may be controlled to have a thickness of less than about 20 nm, less than about 15 nm, less than about 10 nm, less than about 5 nm, etc., as previously described, such that attachment of the entity to the layer results in the distance between the entity and the outermost border of the core of the nanoscale wire is less than about 20 nm, less than about 15 nm, less than about 10 nm, less than about 5 nm, etc.

In some cases, the remaining precursor molecules on the surface of the nanoscale wire, which are not covalently bound to an entity, may be passivated, for example, using techniques such as those described herein. For instance, the remaining precursor molecules may be passivated by exposure of the nanoscale wire to a passivating agent to such as ethanolamine.

Non-limiting examples of chemistries suitable for attaching entities to surfaces of nanoscale wires, optionally via one or more linkers, include the following. In one set of embodiments of the present invention, the surface of the nanoscale wire may be functionalized, for example, the surface may be functionalized with aldehydes, amines, thiols, or the like, which may form nitrogen-containing or sulfur-containing covalent bonds. For instance, in some embodiments, the reaction entity may be covalently bound to the nanoscale wire through the use of a moiety such as an aldehyde moiety, an amine moiety, and/or a thiol moiety.

In certain embodiments, a nanoscale wire may be reacted with an aldehyde, amine, or a thiol in solution to functionalize the nanoscale wire with the appropriate moiety, e.g., such that the surface of the nanoscale wire includes terminal aldehyde, amine, and/or thiol groups. For example, the solution may contain an aldehyde such as aldehyde propyltrimethoxysilane $((CH_3O)_3SiCH_2CH_2CHO)$, or other aldehydes, for example, having a formula $(OCHR^1)(R^2O)(R^3O)(R^4O)Si$, where each R is independently an alkyl or other carbon-containing moiety. All, or only a portion of, the surface of the nanoscale wire may be functionalized with aldehyde moieties (for example, a portion of the nanoscale wire may be blocked or shielded, prior to aldehydization of the surface). While others have investigated the functionalization of surfaces, aldehyde-functionalized nanoscale wires and similar functionalized nanoscale wires of a controlled thickness have not been previously reported, due to problems in controlling the coupling chemistry at nanometer length scales, for instance, between the nanoscale wire and the aldehyde.

Examples of suitable amines or thiols include amino- and thiol-functionalized silane derivatives, for instance, trimethoxy propylamine silane $((CH_3O)_3SiCH_2CH_2CH_2NH_2)$ or propylthiol trimethoxy silane $((CH_3O)_3SiCH_2CH_2CH_2SH)$, which may react with all, or only a portion of, the surface of the nanoscale wire to form, surfaces functionalized with, respectively, amines or thiols. Other potentially suitable amines may have a formula $(Z^1Z^2NR^1)(R^2O)(R^3O)(R^4O)Si$, where each R is independently an alkyl or other carbon-containing moiety and each Z independently is —H or an alkyl or other carbon-containing moiety; other potentially suitable thiols may have a formula $(HSR^1)(R^2O)(R^3O)(R^4O)Si$. In some cases, the derivative may have more than one functional group, for example, the derivative may have an amine and a thiol group, an amine and an aldehyde group, a thiol and an aldehyde group, etc.

One or more entities, e.g., reaction entities such as proteins, enzymes, nucleic acids, antibodies, receptors, ligands, etc., may then be reacted with the aldehyde, amine, and/or thiol moieties to covalently bind the entity to the nanoscale wire. In some cases, after the entity has been fastened to the nanoscale wire, the surface of the nanoscale wire, including any unreacted moieties, is then passivated, e.g., blocked with one or more compounds that causes the moieties to become unreactive. Non-limiting examples of such passivating agents include ethanolamine. For example, a solution may be added to the nanowires that includes one or more passivating agents.

In some cases, the entity covalently binds to an aldehyde group via a reaction between a functional group of the entity and the aldehyde. For instance, if the entity contains a primary amine ($RNH_2$), the primary amine can react with the aldehyde to produce an imine bond ($R^1CH{=}NR^2$), e.g. as in a reaction:

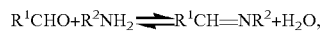

where $R^1$ represents the surface of the nanoscale wire and/or a species immobilized relative to the surface of the nanoscale wire, and $R^2$ is an alkyl or other carbon-containing moiety. Thus, as a particular, non-limiting example, a entity containing an amine, such as a protein, an antibody, or an enzyme, may be reacted with an aldehyde on the surface of the nanoscale wire, thereby covalently binding the entity to the surface of the nanoscale wire. As another non-limiting example, an entity that does not contain a primary amine, such as a nucleic acid molecule, may be modified to include a primary amine, and then the primary amine reacted with an aldehyde on the surface of the nanoscale wire, thereby binding the entity to the surface of the nanoscale wire. Similarly, the entity may covalently bind to an amine or a thiol group via reaction between a functional group of the entity and an amine or thiol.

In one set of embodiments, a nitrogen-containing covalent bond may be formed between an entity and a functional group present on the surface of a nanoscale wire, thereby immobilizing the entity with respect to the surface of the nanoscale wire. In one embodiment, the covalent bond is a nitrogen-containing covalent bond, such as an imine bond, an amide bond, a carbamate bond, etc. As an example, an entity containing an amine may react with an aldehyde present on the surface of a nanoscale wire to form an imine bond, e.g., as previously described. As another example, an entity containing an aldehyde may react with an amine via the following reaction:

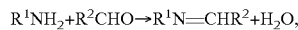
$R^1NH_2 + R^2CHO \rightarrow R^1N=CHR^2 + H_2O$, where $R^1$ represents the surface of the nanoscale wire and/or a species immobilized relative to the surface of the nanoscale wire, and $R^2$ is an alkyl or other carbon-containing moiety. In this reaction, an imine bond is produced, immobilizing $R^2$ with respect to $R^1$. As yet another example, an amine may react with a carboxylic acid, producing an amide bond immobilizing an entity with respect to a surface, e.g., as follows:

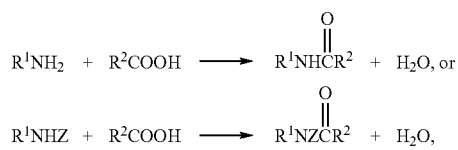

where $R^1$ represents the surface of the nanoscale wire and/or a species immobilized relative to the surface of the nanoscale wire, $R^2$ is an alkyl or other carbon-containing moiety, and Z is —H or an alkyl or other carbon-containing moiety. Other examples of reactions include reactions forming carbamate $(R^1R^2N—C(=O)—O—R^3)$ bonds. For instance, an entity comprising an N-hydroxysuccinimide group or other similar leaving group may react with an amine to form a carbamate bond, e.g., as in a reaction:

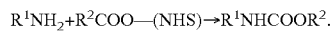
$R^1NH_2 + R^2COO—(NHS) \rightarrow R^1NHCOOR^2$.

where $R^1$ represents the surface of the nanoscale wire and/or a species immobilized relative to the surface of the nanoscale wire, $R^2$ is an alkyl or other carbon-containing moiety, and (NHS) is an N-hydroxysuccinimide group.

In another example, a sulfur-containing covalent bond may be formed between an entity and a functional group present on the surface of a nanoscale wire, thereby immobilizing the entity with respect to the surface of the nanoscale wire. An example is a reaction involving a thiol. For instance, in one embodiment, an entity may be covalently immobilized to a thiol group via the following reaction:

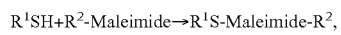
$R^1SH + R^2\text{-Maleimide} \rightarrow R^1S\text{-Maleimide-}R^2$, where $R^1$ represents the surface of the nanoscale wire and/or a species immobilized relative to the surface of the nanoscale wire, and $R^2$ is an alkyl or other carbon-containing moiety. Thus, $R^2$ is immobilized with respect to $R^1$ via a sulfur-containing covalent bond.

In some embodiments, the molecules covalently bound to the surface of the nanoscale wire may comprise a lipid region, e.g., including one or more hydrocarbon chains (e.g., containing carbon and hydrogen atoms). In some cases, the hydrocarbon chains are straight-chain saturated alkyls, e.g., as is shown in FIG. 3A. However, in other cases, one or more hydrocarbon chains may be unsaturated, and/or include one or more heteroatoms. In some embodiments, one or more hydrocarbon chains may be branched.

In one embodiment, a series of molecules is covalently bonded to an aldehyde-functionalized surface of a nanoscale wire to form a layer on the surface of the nanoscale wire, e.g., as previously described. However, in another embodiment, a layer may be formed on the surface of a nanoscale wire through the reaction of a halogenated silane (or other silane with a suitable leaving group) with a hydroxide moiety on the nanoscale wire, e.g. as in the reaction:

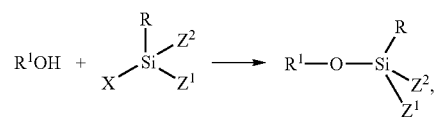

with a hydrohalic acid (HX) as a by-product. In the above structures, $R^1$ represents the surface of the nanoscale wire and/or a species immobilized relative to the surface of the nanoscale wire, X is a halogen or other leaving group, R is an alkyl (for example, an unsubstituted straight-chain saturated alkyl, such as —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H_{35}$, —$C_{18}H_{37}$, etc.), and each of $Z^1$ and $Z^2$ is independently —H, a halogen, or an alkyl or other carbon-containing moiety. The halogenated silane may be reacted, in some cases, with the nanoscale wire in a non-aqueous environment, e.g., using an organic solvent such as anhydrous toluene. Non-limiting examples of halogenated silanes include:

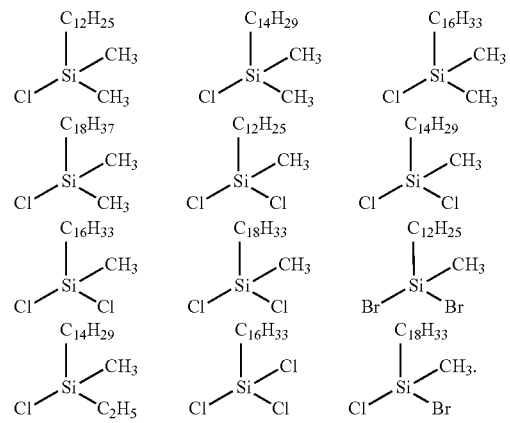

In some cases, e.g., as illustrated above, more than one halogen may be present in the halogenated silane, and some or all of the halogens may participate in reactions between the halogenated silane and one or more hydroxide groups on the nanoscale wire. Thus, as an example, one or more halogens in the above structure may react such that the silane becomes covalently bound to the surface of the nanoscale wire via —O—Si—bonds, e.g., as in the following structures:

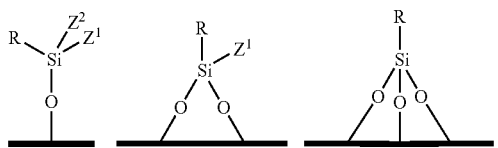

where ━━━ represents the surface of the nanoscale wire, R is an alkyl (for example, an unsubstituted straight-chain saturated alkyl), and each of $Z^1$ and $Z^2$ is independently —H, a halogen, or an alkyl or other carbon-containing moiety.

As used herein, the term "halogen," or equivalently, "halogen atom," is given its ordinary meaning as used in the field of chemistry. The halogens include fluorine, chlorine, bromine, iodine, and astatine, and may have any charge state and/or electronic configuration. In some cases, the halogen atoms include one or more of fluorine, chlorine, bromine, or iodine. In certain embodiments, the halogen atoms found within the halogenated silane are fluorine, chlorine, and bromine; fluorine and chlorine; chlorine and bromine, or a single type of halogen atom.

Also, as used herein, the term "alkyl" is given its ordinary meaning as used in the field of organic chemistry. Alkyl (i.e., aliphatic) moieties useful for practicing the invention can contain any of a wide number of carbon atoms, for example, 4, 5, 6, 7, 8, 9, 10, 11, 12, 13, 14, 15, 16, 17, 18, 19, or 20 or more carbon atoms. In some embodiments, the alkyl moiety will contain at least 8 carbon atoms, at least 10 carbon atoms, at least 12 carbon atoms, at least 14 carbon atoms, at least 16 carbon atoms, or at least 18 carbon atoms; in some embodiments, the alkyl moiety will have at most 25 carbon atoms, or at most 20 carbon atoms. Alkyls of the present invention may be lower alkyls or higher alkyls in some cases. As used herein, a "lower alkyl" is an alkyl that has less than 5 carbon atoms, while a "higher alkyl" is an alkyl that contains at least 5 carbon atoms.

The carbon atoms within the alkyl moiety may be arranged in any configuration within the alkyl moiety, for example, as a straight chain (i.e., a n-alkyl such as methyl, ethyl, propyl, butyl, pentyl, hexyl, heptyl, octyl, nonyl, decyl, etc.) or a branched chain, i.e., a chain where there is at least one carbon atom that is covalently bonded to at least three carbon atoms (e.g., a t-butyl moiety or a sec-butyl moiety, an isoalkyl moiety such as isopropyl, isobutyl, isopentyl, isohexyl, isoheptyl, isooctyl, isononyl, etc.). In some cases, the alkyl may contain one or more rings (e.g., cycloalkyls). The alkyl moiety may contain only single bonds (i.e., the alkyl is a "saturated alkyl," or the alkyl may contain one or more double and/or triple bonds within its structure (i.e., the alkyl is an "unsaturated alkyl"), for example, as in an alkenyl, an alkynyl, an alkenynyl, etc. As known to those of ordinary skill in the art, an alkenyl comprises at least one double bond, an alkynyl comprises at least one triple bond, and an alkenynyl comprises at least one double bond and at least one triple bond (i.e., the alkenynyl is both an alkenyl and an alkynyl). Terms such as "lower alkenyl," "higher alkenyl," "lower alkynyl," "higher alkynyl," etc., are defined analogously to the terms "lower alkyl" and "higher alkyl," discussed above.

In some embodiments, the alkyl moiety contains only carbon and hydrogen atoms; however, in other embodiments, the alkyl moiety may also contain one or more heteroatoms, i.e., non-carbon and/or non-hydrogen moieties may be present within an alkyl moiety, for example, halogen atoms, oxygen atoms, nitrogen atoms, etc.

In some cases, a layer of molecules present on the surface of a nanoscale wire may be used to immobilize other entities relative to the nanoscale wire, for example, entities having a hydrophobic moiety, e.g., a ganglioside, a glycosphingolipid, etc., as described herein. For instance, if the layer of molecules is hydrophobic (e.g., contains hydrocarbon chains, for example, higher alkyls, or unsubstituted straight-chain alkyls, which may be saturated or unsaturated), hydrophobic interactions between the hydrophobic layer and the hydrophobic moiety of the entity may be used to immobilize the entity relative to the nanoscale wire. As a non-limiting example, in FIG. 3B, a nanoscale wire 130, disposed between electrodes 131, 132, has several hydroxide moieties (—OH) on its surface. The nanowire is then exposed to anhydrous toluene and (chloro)(dimethyl)(tetradecyl)silane, which react to produce HCl and the attachment of a hydrocarbon monolayer on the surface of the nanoscale wire (FIG. 3C). Optionally, the hydrophobic moieties of other entities, such as gangliosides or surfactants, may interact with the monolayer, resulting in the immobilization of those entities relative to the nanoscale wire (FIG. 3D). In this figure, the hydrophobic portion of the moiety is represented by a straight-chain saturated alkyl and the hydrophilic portion of the moiety is represented by the symbol

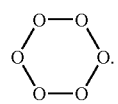

Also provided, according to another set of embodiments of the present invention, is a sensing element comprising a nanoscale wire and a detector constructed and to arranged to determine a property and/or a change in a property of the nanoscale wire. In some cases, alteration of a property of the nanoscale wire may be indicative of an interaction between a reaction entity and an analyte (e.g., association or dissociation of the reaction entity and the analyte). Where a detector is present, any detector capable of determining a property associated with the nanoscale wire can be used. The property can be electronic, electromagnetic, optical, mechanical, or the like. Examples of electrical or magnetic properties that can be determined include, but are not limited to, voltage, current, conductivity, resistance, impedance, inductance, charge, etc. Examples of optical properties associated with the nanoscale wire include its emission intensity and/or emission wavelength, e.g. where the nanoscale wire is emissive. In some cases, the detector will include a power source and a metering device, for example a voltmeter or an ammeter.

In one embodiment, a conductance (or a change in conductance) less than about 1 nS in a nanoscale wire sensor of the invention can be detected. In another embodiment, a conductance in the range of thousandths of a nS can be detected. In other embodiments, conductances of less than about 10 microsiemens, less than about 1 microsiemen, less than about 100 nS, or less than about 10 nS can be detected. The concentration of a species, or analyte, may be detected from femtomolar concentrations, to nanomolar, micromolar, millimolar, and to molar concentrations and above. By using nanoscale wires with known detectors, sensitivity can be extended to a single molecules in some cases.

As a non-limiting example, a charged analyte may be determined by determining a change in an electrical property of the nanoscale wire, for example, conductivity. Immobilizing a charged analyte relative to the nanoscale wire may cause a change in the conductivity of the nanoscale wire, and in some cases, the distance between the charged analyte and the nanoscale wire may determine the magnitude of the change in conductivity of the nanoscale wire. Uncharged analytes can be similarly determined, for instance, by causing the analyte to become charged, e.g., by altering environmental conditions such as pH (by raising or lowering pH), temperature, reactants, or the like, by reacting the analyte with a charged moiety, or the like.

The analyte to be determined by the nanoscale sensor may be present within a sample. The term "sample" refers to any cell, lysate, tissue, or fluid from a biological source (a "biological sample"), or any other medium, biological or non-biological, that can be evaluated in accordance with the invention. The sample may be, for instance, a liquid (e.g., a solution or a suspension) or a gas. A sample includes, but is not limited to, a biological sample drawn from an organism (e.g. a human, a non-human mammal, an invertebrate, a plant, a fungus, an algae, a bacteria, a virus, etc.), a sample drawn from food designed for human consumption, a sample including food designed for animal consumption such as livestock feed, milk, an organ donation sample, a sample of blood destined for a blood supply, a sample from a water supply, a soil sample, or the like.

In some cases, the sample may be a sample suspected of containing an analyte. A "sample suspected of containing" a particular component means a sample with respect to which the content of the component is unknown. For example, a fluid sample from a human suspected of having a disease, but not known to have the disease, defines a sample suspected of containing the disease. "Sample" in this context includes naturally-occurring samples, such as physiological samples from humans or other animals, samples from food, livestock feed, water, soil, etc. Typical samples include tissue biopsies, cells, cell lysates, whole blood, serum or other blood fractions, urine, ocular fluid, saliva, fluid or other samples from tonsils, lymph nodes, needle biopsies, etc.

A variety of sample sizes, for exposure of a sample to a nanoscale sensor of the invention, can be used in various embodiments. As examples, the sample size used in nanoscale sensors may be less than or equal to about 10 microliters, less than or equal to about 1 microliter, or less than or equal to about 0.1 microliter. The sample size may be as small as about 10 nanoliters, 1 nanoliter, or less, in certain instances. The nanoscale sensor also allows for unique accessibility to biological species and may be used for in vivo and/or in vitro applications. When used in vivo, in some case, the nanoscale sensor and corresponding method result in a minimally invasive procedure.

The invention, in some embodiments, involves a sensing element comprising a sample exposure region and a nanoscale wire able to detect the presence or absence of an analyte, and/or the concentration of the analyte. The "sample exposure region" may be any region in close proximity to the nanoscale wire where a sample in the sample exposure region addresses at least a portion of the nanoscale wire. Examples of sample exposure regions include, but are not limited to, a well, a channel, a microfluidic channel, or a gel. In certain embodiments, the sample exposure region is able to hold a sample proximate the nanoscale wire, and/or may direct a sample toward the nanoscale wire for determination of an analyte in the sample. The nanoscale wire may be positioned adjacent or within the sample exposure region. Alternatively, the nanoscale wire may be a probe that is inserted into a fluid or fluid flow path. The nanoscale wire probe may also comprise, in some instances, a microneedle that supports and/or is integral with the nanoscale wire, and the sample exposure region may be addressable by the microneedle. In this arrangement, a device that is constructed and arranged for insertion of a microneedle probe into a sample can include a region surrounding or otherwise in contact with the microneedle that defines the sample exposure region, and a sample in the sample exposure region is addressable by the nanoscale wire, and vice versa. Fluid flow channels can be created at a size and scale advantageous for use in the invention (microchannels) using a variety of techniques such as those described in International Patent Application Serial No. PCT/US97/04005, entitled "Method of Forming Articles and Patterning Surfaces via Capillary Micromolding," filed Mar. 14, 1997, published as Publication No. WO 97/33737 on Sep. 18, 1997, and incorporated herein by reference.

As an example, a sample, such as a fluid suspected of containing an analyte that is to be determined, may be presented to a sample exposure region of a sensing element comprising a nanoscale wire. An analyte present in the fluid that is able to bind to the nanoscale wire and/or a reaction entity immobilized relative to the nanoscale wire may cause a change in a property of the nanoscale wire that is determinable upon binding, e.g. using conventional electronics. If the analyte is not present in the fluid, the relevant property of the nanoscale wire will remain unchanged, and the detector will measure no significant change. Thus, according to this particular example, the presence or absence of an analyte can be determined by monitoring changes, or lack thereof, in the property of the nanoscale wire. In some cases, if the detector measures a change, the magnitude of the change may be a function of the concentration of the analyte, and/or a function of some other relevant property of the analyte (e.g., charge or size, etc.). Thus, by determining the change in the property of the nanoscale wire, the concentration or other property of the analyte in the sample may be determined.

In some embodiments, one or more nanoscale wires may be positioned in a channel or in a microfluidic channel, which may define the sample exposure region in some cases. As used herein, a "channel" is a conduit that is able to transport one or more fluids specifically from one location to another. Materials may flow through the channels, continuously, randomly, intermittently, etc. The channel may be a closed channel, or a channel that is open, for example, open to the external environment. The channel can include characteristics that facilitate control over fluid transport, e.g., structural characteristics, physical/chemical characteristics (e.g., hydrophobicity vs. hydrophilicity) and/or other characteristics that can exert a force (e.g., a containing force) on a fluid when within the channel. The fluid within the channel may partially or completely fill the channel. In some cases the fluid may be held or confined within the channel or a portion of the channel in some fashion, for example, using surface tension (i.e., such that the fluid is held within the channel within a meniscus, such as a concave or convex meniscus). The channel may have any suitable cross-sectional shape that allows for fluid transport, for example, a square channel, a circular channel, a rounded channel, a rectangular channel (e.g., having any aspect ratio), a triangular channel, an irregular channel, etc. The channel may be of any size. For example, the channel may have a largest dimension perpendicular to a direction of fluid flow within the channel of less than about 1000 micrometers in some cases (i.e., a microfluidic channel), less than about 500 micrometers in other cases, less than about 400 micrometers in other cases, less than about 300 micrometers in other cases, less than about 200 micrometers in still other cases, less than about 100 micrometers in still other cases, or less than about 50 or 25 micrometers in still other cases. In some embodiments, the dimensions of the channel may be chosen such that fluid is able to freely flow through the channel. The dimensions of the channel may also be chosen in certain cases, for example, to allow a certain volumetric or linear flowrate of fluid within the channel. Of course, the number of channels, the shape or geometry of the channels, and the placement of channels can be determined by those of ordinary skill in the art.

One or more different nanoscale wires may cross the same microfluidic channel (e.g., at different positions) to detect the same or different analytes, to measure a flowrate of an analyte(s), etc. In another embodiment, one or more nanoscale wires may be positioned in a microfluidic channel to form one of a plurality of analytic elements, for to instance, in a microneedle probe, a dip and read probe, etc. The analytic elements probe may be implantable and capable of detecting several analytes simultaneously in real time, according to certain embodiments. In another embodiment, one or more nanoscale wires may be positioned in a microfluidic channel to form an analytic element in a microarray for a cassette or a lab-on-a-chip device. Those of ordinary skill in the art would know of examples of cassette or lab-on-a-chip devices that are suitable for high-throughout chemical analysis and screening, combinational drug discovery, etc. The ability to include multiple nanoscale wires in one nanoscale sensor also allows, in some cases, for the simultaneous detection of different analytes suspected of being present in a single sample, i.e., the nanoscale sensor allows "multiplexed" detection of different analytes. For example, a nanoscale sensor may include a plurality of nanoscale wires that each detect different pH levels, proteins, enzymes, toxins, small molecules, and/or nucleic acids, etc.

In one set of embodiments, the use of multiple nanoscale wires may prevent or at least decrease the frequency of "false positive" events, i.e., where it appears that a binding event or other interaction between a reaction entity and an analyte has occurred, based on a determination of a property of the nanoscale wire (e.g., a change in conductance) when, in fact, no such event or interaction has occurred. By comparing the properties of different nanoscale wires (e.g., having the same or different compositions, and/or the same or different reaction entities), false positive events can be identified. As a non-limiting example, two nanoscale wires, each having the same reaction entity, or different reaction entities able to bind the same analyte, can be compared to determine whether an analyte is actually present in a sample that both nanoscale wires are exposed to, e.g., by determining if both nanoscale wires are able to bind or otherwise interact with the reaction entity, e.g., simultaneously. As another non-limiting example, the first nanoscale wire may be p-doped, and the second nanoscale wire may be n-doped, such that binding of analytes to each of the reaction entities may cause different changes in the properties of the nanoscale wires (e.g., the conductivity of one wire may increase, while the conductivity of the other wire decreases). Thus, in one set of embodiments, two or more nanoscale wires, each having a reaction entity able to bind an analyte, are compared such that two or more binding events with respect to two or more of the nanoscale wires are required for the binding event to be considered genuine, whereas a to binding event involving only one nanoscale wire (or less than a predetermined number of nanoscale wires) is treated as a "false positive." Other nanoscale wires of different composition, analogous to the n-doped and p-doped nanowires described above, can be used, and the different nanoscale wires may cause different changes to occur based upon binding of an identical analyte to each nanoscale wire. Different analytes can be detected by these different nanoscale wires as well.

Of course, in a in a situation where binding occurs at one possible site but not at another possible site, additional experiments may be required in some cases to determine whether a binding event occurred or whether a "false positive" signal was detected. In some cases (e.g., a very dilute sample or other situation involving very little analyte present), two nanoscale wires may be present, each having a reaction entity immobilized thereon (or other entity with which the analyte is able to interact with), and an analyte that binds to one nanoscale wire only is a positive binding event rather than a false positive. Those of ordinary skill in the art will be able to establish experimental protocols to determine, positively, whether a binding event has occurred in these and similar situations.

In some cases, the sensing element may comprise a plurality of nanoscale wires able to determine (i.e., detect the presence, absence, and/or amount or concentration) one or more analytes within a sample, for example, from a liquid or solution, blood serum, etc., as previously described. Various nanoscale wires within the sensing element may be differentially doped as described herein, and/or contain different reaction entities, and/or the same reaction entities at different concentrations, thereby varying the sensitivity of the nanoscale wires to the analytes, as needed. For example, different reaction entities may be "printed" on the nanoscale wires, e.g., using microarray printing techniques or the like, thereby producing an array of nanoscale wires comprising different reaction entities. In some cases, individual nanoscale wires may be selected based on their ability to interact with specific analytes, thereby allowing the detection of a variety of analytes. The plurality of nanoscale wires may be randomly oriented or parallel to one another, according to another set of embodiments. The plurality of nanoscale wires may also be oriented in an array on a substrate, in specific instances.

A sensing element of the present invention can collect real time data and/or near-real time data, in some embodiments. The data may be used, for example, to monitor the to reaction rate of a specific chemical or biological reaction. Physiological conditions or drug concentrations present in vivo may also produce a real time (or near-real time) signal that may be used to control a drug delivery system, in another embodiment of the invention. An example of near-real time data is a system in which multiple nanoscale wires are individually addressed, e.g., using a switching matrix. The switching matrix can address each wire on any suitable basis, for example, once per second, once every 100 milliseconds, once every 10 milliseconds, once every millisecond, once every 100 microseconds, once every 10 microseconds, once every microsecond, etc.

In addition, electrical determination of one or more properties of the nanoscale wire may allow for the determination of one or more analytes as a function of time. For example, the conductance of a nanoscale wire may be determined as a function of time, which may give additional information regarding the analyte. In some cases, a microarray of the invention may be exposed to a series of samples, and the properties of the nanoscale wire, as determined as a function of time, may be related to the concentration of analyte within each of the samples. This feature may also, in some cases, be combined with the use of multiple nanoscale wires to detect different analytes. Thus, in some embodiments, a sensing element of the invention may be used to detect multiple analytes in one or more samples.

In some cases, the nanoscale wires, or at least a portion of the nanoscale wires, may be individually addressable, i.e., the status of the nanoscale wire may be determined without determining the status of nearby nanoscale wires. Thus, for example, a nanoscale wire within a sensing element, or a number of nanoscale wires within the sensing element, may be in electrical communication with an electrode that is able to address the nanoscale wire(s), and such a wire may be addressed using the electrode without addressing other nanoscale wires not in electrical communication with the electrode. For example, a first reaction entity immobilized relative to a first nanoscale wire may bind an analyte, and such a binding event may be detectable independently of the detection of a binding event involving a second reaction entity immobilized relative to a second nanoscale wire. The electrodes may be in electronic communication with one or more electrical contacts.

In some embodiments, the invention includes a microarray including a plurality of sensing regions, at least some of which comprise one or more nanoscale wires. The microarray, including some or all of the sensing regions, may define a sensing element in a sensor device. At least some of the nanoscale wires are able to determine an analyte suspected to be present in a sample that the sensing region of the microarray is exposed to, for example, the nanoscale wire may comprise a reaction entity able to interact with an analyte. If more than one nanoscale wire is present within the sensing region, the nanoscale wires may be able to detect the same analyte and/or different analytes, depending on the application. For example, the nanoscale wires within the sensing region of the microarray may be able to determine 1, 2, 3, 4, 5, 6, 8, 10, 12, 14, 16, 18, 20, 22, 24, 26, 28, 30, 40, 50, or more analytes or types of analytes. As an example, a microarray may have one or more sensing regions, at least some of which comprise nanoscale wires having nucleic acids immobilized with respect to the nanoscale wires, e.g., as described herein. The microarray may be used to determine analytes in one, or a number of samples. For example, the microarray may include at least 2, at least 3, at least 5, at least 10, at least 15, at least 20, at least 25, at least 30, at least 50, at least 70, at least 100, at least 200, at least 300, at least 500, at least 1,000, at least 3,000, at least 5,000, or at least 10,000 or more sensing regions, at least some of which may be used to determine the analyte of a sample placed on the sensing region. In certain cases, the microarray may have a high density of nanoscale wires, at least some of which may be individually addressable, and at least some of which can be used to determine an analyte suspected to be present in a sample. For instance, the density of nanoscale wires may be at least about 100 nanoscale wires/cm$^2$, and in some cases, at least about 110 nanoscale wires/cm$^2$, at least about 120 nanoscale wires/cm$^2$, at least about 130 nanoscale wires/cm$^2$, at least about 150 nanoscale wires/cm$^2$, at least about 200 nanoscale wires/cm$^2$, at least about 250 nanoscale wires/cm$^2$, or at least about 500 nanoscale wires/cm$^2$.

Figure 4A:
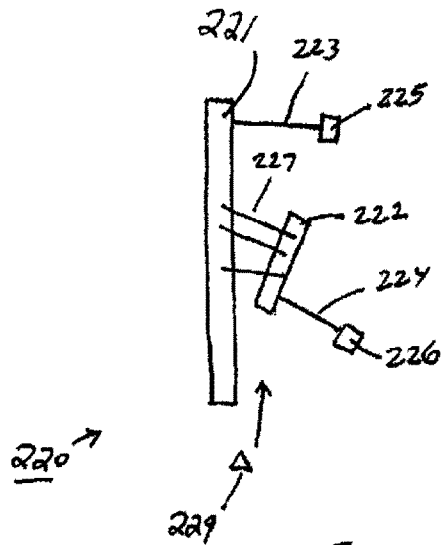
FIGS. 4A-4E illustrate sensors according to various embodiments of the invention.

An example of a sensing region is shown in FIG. 4A. In this figure, the sensing region 220 includes a first electrode 221 and a second or counter electrode 222. The first electrode is generally elongated (i.e., one dimension of the electrode is significantly longer in one dimension than another). One or more nanoscale wires 227 are in electrical communication with first electrode 221 and second electrode 222, and at least some of the nanoscale wires may comprise a reaction entity able to interact with an analyte. First electrode 221 is in electronic communication with an electrical contact or lead 225 through electronic connection 223 (e.g., a wire or an etched electronic pathway), while second electrode 222 is in electronic communication with an electrical contact 225 through electronic connection 224. Analyte 229 is present in a sample that is placed within sensing region 220, and is able to interact with a reaction entity present on a nanoscale wire 227 (e.g., by binding, for example, covalently). Upon such an interaction, an electrical property of the nanoscale wire, e.g., conductivity, is altered (e.g., through a charge interaction between the analyte and the nanoscale wire), which can be determined by determining a change in conductivity of the nanoscale wire, for instance, by measuring a change in conductivity between electrical contact 225 and electrical contact 226.

Figure 4B:
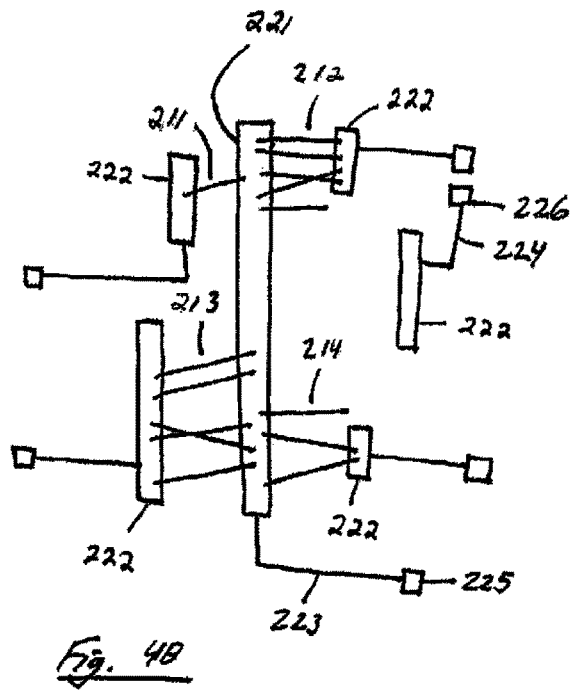

Additional nanoscale wires may be added to the sensing region. For example, in FIG. 4B, sensing region 220 has five second or counter electrodes 222. At least some of nanoscale wires 211, 212, 213, 214 connect at least some of the second electrodes 222 with first electrode 221, and at least some of the nanoscale wires may comprise a reaction entity able to interact with an analyte. For instance, nanoscale wires 211 may interact with a first analyte, but not with a second analyte or a third analyte, while nanoscale wires 212 may interact with only the second analyte and nanoscale wires 213 may interact with only the third analyte. Upon a binding event of an analyte with a corresponding reaction entity, a property of the nanoscale wire, such as conductance, may change, and may be determined, as previously described.

Figure 4C:
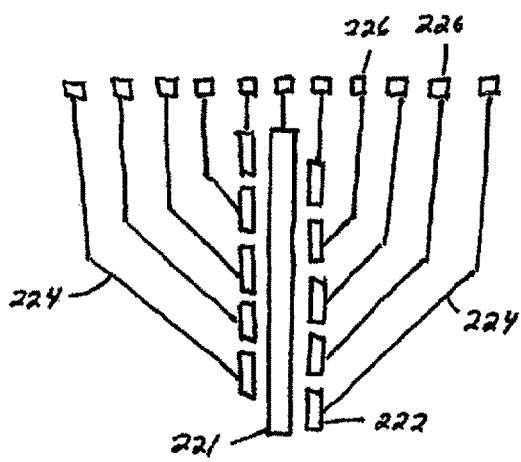
Figure 4E:
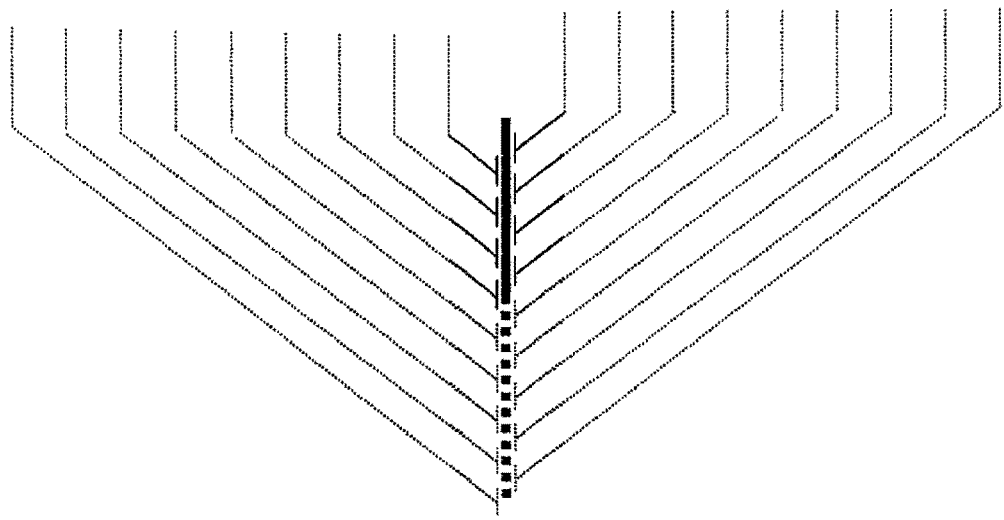
Figure 4D:
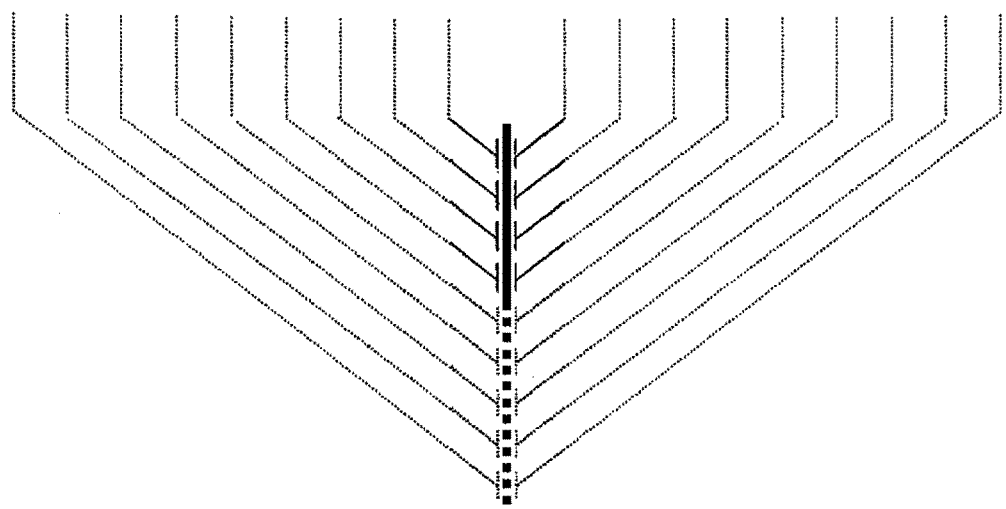

In FIG. 4C, a relatively large number of second or counter electrodes are positioned in parallel about the first electrode (i.e., the second electrodes are disposed in a generally linear array that is essentially parallel to the first electrode), and the electrical pathways or leads between the second electrodes and the electrical contacts are positioned such that at least some of the pathways are angled, i.e., non-perpendicular. (The nanoscale wires are not illustrated in FIG. 4C for clarity, but may span between the first and second electrodes.) In this figure, the second electrodes are spaced essentially equidistantly from the first electrode. The pathways or leads may be positioned to be in parallel to each other, and in some cases, the leads may be positioned at an angle with respect to the first and/or second electrodes, i.e., the leads are not perpendicular to the first and/or second electrodes. Such pathways or leads may allow closer or more dense packing of the pathways and/or electrical contacts 226, for example, to allow interfacing to of the electrical contacts with detectors able to determine changes in properties of the nanoscale wires. Additional examples of such a system are shown in FIGS. 4D-4E, where the dotted lines indicate optional features. Such as system may include certain ornamental features, as shown in these figures. In some cases, if the second electrodes are positioned on either side of the first electrode, the second electrodes may be aligned with each other, e.g., as is shown in FIG. 5B, or not aligned (e.g., "staggered"), e.g., as is shown in FIG. 4C In another set of embodiments, an article of the invention may comprise a cassette comprising a sensing element having a sample exposure region and a nanoscale wire. The detection of an analyte in a sample within the sample exposure region may occur, in some cases, while the cassette is disconnected to a detector apparatus, allowing samples to be gathered at one site, and determined at another. The cassette may then be operatively connectable to a detector apparatus able to determine a property associated with the nanoscale wire. As used herein, a device is "operatively connectable" when it has the ability to attach and interact with another apparatus. In other cases, the cassette may be constructed and arranged such that samples may be gathered and determination at one site.

As an example, the present invention includes, in some embodiments, an integrated system comprising a nanoscale wire detector, a reader, and a computer controlled response system. In this example, the nanoscale wire detects a change in the equilibrium or concentration of an analyte in the sample, feeding a signal to the computer controlled response system, causing it to withhold or release a chemical or drug. This is useful as an implantable drug or chemical delivery system because of its small size and low energy requirements. Those of ordinary skill in the art are well aware of the parameters and requirements for constructing implantable devices, readers, and computer-controlled response systems suitable for use in connection with the present invention. That is, the knowledge of those of ordinary skill in the art, coupled with the disclosure herein of nanoscale wires as sensors, enables implantable devices, real-time measurement devices, integrated systems, and the like. Such systems can be made capable of monitoring one, or a plurality of, physiological characteristics individually or simultaneously. Such physiological characteristics can include, for example, oxygen concentration, carbon dioxide concentration, glucose level, concentration of a particular to drug or molecule, concentration of a particular drug by-product, concentration of an enzyme or protein, concentration of a toxin, or the like. Integrated physiological devices can be constructed to carry out a function depending upon a condition sensed by a sensor of the invention.

The present invention finds use in a wide range of applications. For instance, in one set of embodiments, any of the techniques described herein may be used in the determination of proteins, enzymes, toxins, viruses, small molecules, or the like, e.g., as in an assay, for example, to detect or diagnose cancer or other medical conditions, toxins or other environmental agents, viruses, or the like. A property of an analyte may be determined by allowing the analyte to interact with a nanoscale wire and/or a reaction entity, and the interaction may be analyzed or determined in some fashion, e.g., quantified. In some cases, the degree or amount of interaction (e.g., a binding constant) may be determined, for example, by measuring a property of the nanoscale wire (e.g., an electronic property, such as the conductance) after exposing the nanoscale wire and/or the reaction entity to the analyte.

In certain instances, such assays are useful in drug screening techniques. In one example, a protein, enzyme, or other target molecule may be immobilized relative to a nanoscale wire as a reaction entity, and exposed to one or more drug candidates, for example, serially or simultaneously. Interaction of the drug candidate(s) with the reaction entity may be determined by determining a property of the nanoscale wire, e.g., as previously described. As a non-limiting example, a nanoscale wire, having an associated reaction entity, may be exposed to one or more species able to interact with the reaction entity, for instance, the nanoscale wire may be exposed to a sample containing a first species able to interact with the reaction entity, where the sample contains or is suspected of containing a second species able to interact with the reaction entity, and optionally other, different species, where one of the species is a drug candidate. As one example, if the reaction entity is an enzyme, the sample may contain a substrate and a drug candidate suspected of interacting with the enzyme in a way that inhibits enzyme/substrate interaction; if the reaction entity is a substrate, the sample may contain an enzyme and a drug candidate suspected of interacting with the substrate in an inhibitory manner; if the reaction entity is a nucleic acid, the sample may contain an enzyme able to bind the nucleic acid (e.g., a nucleic acid synthesis enzyme), or a to complementary nucleic acid, and a drug candidate suspected of interacting with the nucleic acid reaction entity in an inhibitory manner; if the reaction entity is a receptor, the sample may contain a ligand for the receptor and a drug candidate suspected of interacting with the receptor in an inhibitory manner; etc. In each of these cases, the drug candidate may also act in a way that enhances, rather than inhibits, interaction.

In some cases, assays of the invention may be used in high-throughput screening applications, e.g., where at least 100, at least 1,000, at least 10,000, or at least 100,000 or more analytes may be rapidly screened, for example, by exposing one or more analytes to a nanoscale wire (e.g., in solution), and/or exposing a plurality of analytes to a plurality of nanoscale wires and/or reaction entities.

Figure 6A:
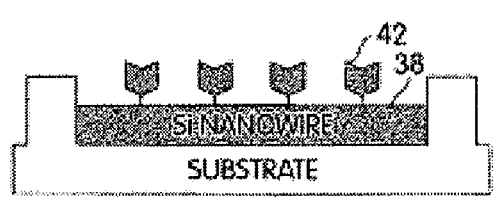
FIGS. 6A-6B schematically illustrate a nanoscale detector device having a reaction entity, according to one embodiment of the invention.
Figure 6B:
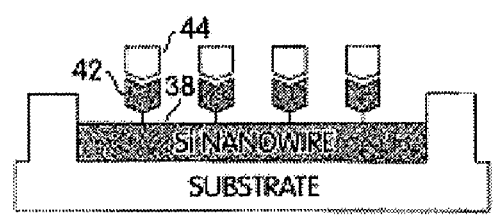

As non-limiting examples, referring now to the figures, FIG. 6A schematically shows a portion of a nanoscale detector device in which nanoscale wire 38 has been modified with a reaction entity that is a binding partner 42 for detecting analyte 44. FIG. 6B schematically shows a portion of the nanoscale detector device of FIG. 6A, in which the analyte 44 is attached to the specific binding partner 42. Selectively functionalizing the surface of nanoscale wires can be done, for example, by functionalizing the nanoscale wire with a siloxane derivative. For example, a nanoscale wire may be modified after construction of the nanoscale detector device by immersing the device in a solution containing the modifying chemicals to be coated. Alternatively, a microfluidic channel may be used to deliver the chemicals to the nanoscale wires. For example, amine groups may be attached by first making the nanoscale detector device hydrophilic by oxygen plasma, or an acid and/or oxidizing agent, and then immersing the nanoscale detector device in a solution containing an amino silane. By way of example, a nucleic acid may be attached by first attaching amine groups as described above, and immersing the modified nanoscale detector device in a solution containing bifunctional crosslinkers, if necessary, and immersing the modified nanoscale detector device in a solution containing the nucleic acid. The process may be accelerated and promoted in some cases by applying a bias voltage to the nanoscale wire. The bias voltage can be either positive or negative depending on the nature of the reaction entity. For example, a positive bias voltage will promote bringing a negatively charged nucleic acid close to the nanoscale wire surface and increasing its reaction rate with surface amino groups.

Figure 7A:
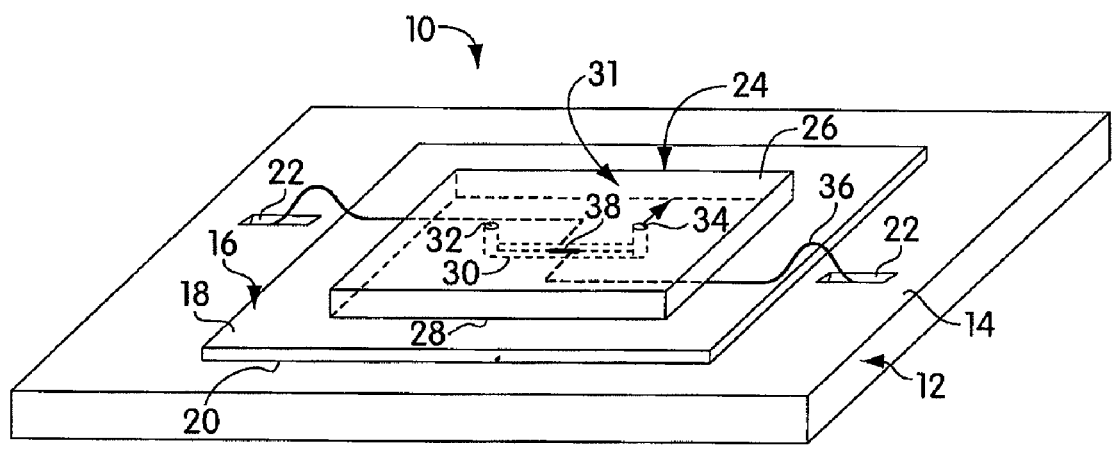
FIGS. 7A-7B schematically illustrate certain nanoscale detector devices that can be used in connection with the invention.

FIG. 7A shows one example of an article of the present invention where one or more nanoscale wires are positioned within a microfluidic channel. In FIG. 7A, nanoscale detector device 10 comprises a nanoscale wire 38 positioned above upper surface 18 of substrate 16. Chip carrier 12 has an upper surface 14 for supporting substrate 16 and electrical connections 22. Chip carrier 12 may be made of any insulating material that allows connection of electrical connections 22 to electrodes 36. In one embodiment, the chip carrier is an epoxy. Upper surface 14 of the chip carrier may be of any shape including, for example, planar, convex, and concave. In one embodiment, upper surface 14 of the chip carrier is planar.

As shown in FIG. 7A, lower surface 20 of substrate 16 is positioned adjacent to upper surface 14 of the chip carrier and supports electrical connection 22. Substrate 16 may be made of a polymer, silicon, quartz, or glass, for example. In one embodiment, the substrate 16 is made of silicon coated with 600 nm of silicon oxide. Upper surface 18 and lower surface 20 of substrate 16 may be of any shape, such as planar, convex, and concave. In some cases, lower surface 20 of substrate 16 contours to upper surface 14 of chip carrier 12. Similarly, mold 24 has an upper surface 26 and a lower surface 28, either of which may be of any shape. In certain embodiments, lower surface 26 of mold 24 contours to upper surface 18 of substrate 16.

Mold 24 has a sample exposure region 30, shown here as a microchannel, having a fluid inlet 32 and fluid outlet 34, shown in FIG. 7A on the upper surface 26 of mold 24. Nanoscale wire 38 is positioned such that at least a portion of the nanoscale wire is positioned within sample exposure region 30. Electrodes 36 connect nanoscale wire 38 to electrical connection 22. Electrical connections 22 are, optionally, connected to a detector (not shown) that measures a change in an electrical or other property of the nanoscale wire. The distance between electrodes 36 may range from 50 nm to about 20 microns, in some cases from about 100 nm to about 10 microns, or from about 500 nm to about 5 microns.

Figure 7B:
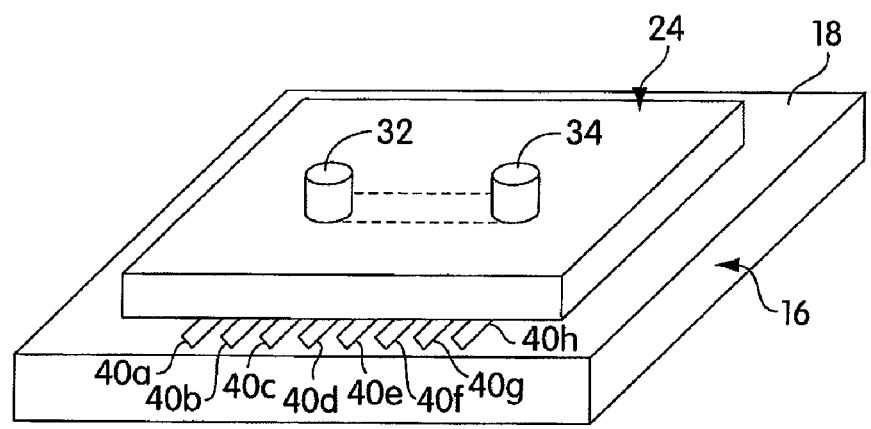

FIG. 7B shows another embodiment of the present invention wherein the nanoscale detector device 10 of FIG. 7A further includes multiple nanoscale wires (not shown). In FIG. 7B, wire interconnects 40*a-h* connect to corresponding nanoscale wires to electrical connections, respectively (not shown). In some cases, each nanoscale wire has a unique reaction entity selected to detect a different analytes in the fluid. In this way, the determination (presence, absence, and/or amount) of several analytes may be to determined using one sample while performing one test.

Figure 8A:
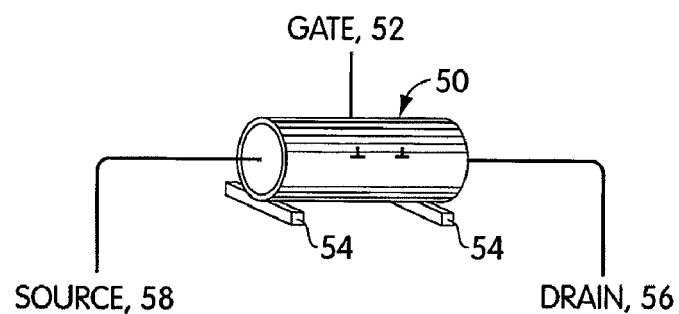
FIGS. 8A-8D illustrate various field effect transistors including nanoscale detectors that can be used in connection with certain embodiments of the invention.

FIG. 8A depicts one example of an embodiment of a nanoscale wire sensor of the invention. In the embodiment shown in FIG. 8A, the nanoscale wire sensor invention comprises a nanoscale wire 50. The nanoscale wire may have one or more reaction entities immobilized relative to the surface. The surface of the nanoscale wire can act as the gate 52 of an FET device and the electrical contacts at either end of the nanoscale wire may allow the ends to act as the drain 56 and the source 58. In the depicted embodiment, the device is symmetric and either end of the nanoscale wire may be considered the drain or the source. For purpose of illustration, the nanoscale wire of FIG. 8A defines the left-hand side as the source and the right hand side as the drain. FIG. 8A also shows that the nanoscale wire device of this embodiment is disposed upon and electrically connected to two conductor elements 54.

Figure 8B:
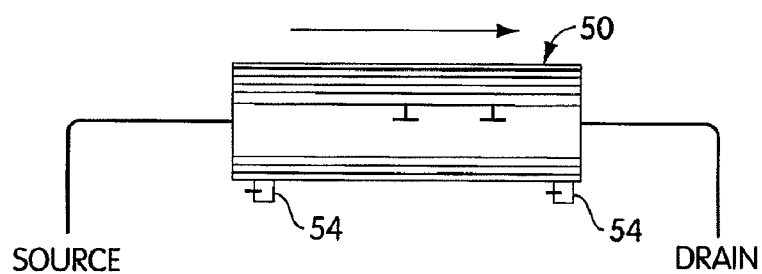
Figure 8C:
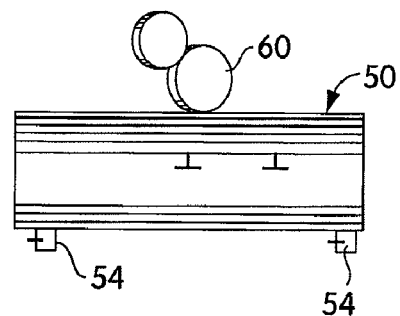
Figure 8D:
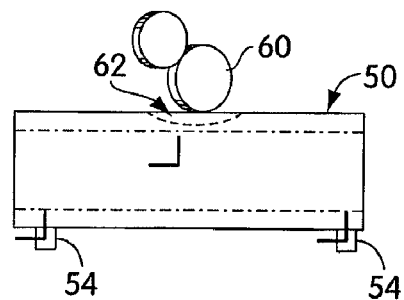

FIGS. 8A and 8B illustrate an example of a chemical and/or ligand-gated field effect transistor ("FET") that can define a sensor of the invention. FETs are well know in the art of electronics, and are described in more detail in, e.g., *The Art of Electronics, Second Edition* by Paul Horowitz and Winfield Hill, Cambridge University Press, 1989, pp. 113-174. In the FET, the availability of charge carriers is controlled by a voltage applied to a third "control electrode," also known as the gate electrode. The conduction in the channel is controlled by a voltage applied to the gate electrode which produces an electric field across the channel. The device of FIGS. 8A and 8B may be considered a chemical or ligand-FET because the chemical or ligand provides the voltage at the gate which produced the electric field which changes the conductivity of the channel. This change in conductivity in the channel effects the flow of current through the channel. For this reason, a FET is often referred to as a transconductant device in which a voltage on the gate controls the current through the channel through the source and the drain. The gate of a FET is insulated from the conduction channel, for example, using a semiconductor junction such in a junction FET (JFET) or using an oxide insulator such as in a metal oxide semiconductor FET (MOSFET). Thus, as an example, in FIGS. 8A and 8B, an $SiO_2$ exterior surface of the nanoscale wire sensor may serve as the gate insulation for the gate.

In application, the nanoscale wire device illustrated in the example of FIG. 8 provides an FET device that may be contacted with a sample or disposed within the path of a sample flow. Analytes of interest within the sample can contact the surface of the nanoscale wire device and, under certain conditions, bind or otherwise become immobilized relative to the surface and/or affect the binding and/or adherence of other species. The exterior surface of the device may, in some cases, have reaction entities, e.g., as described above. The reaction entities may attract the analyte and/or bind the analyte. A non-limiting example is shown in FIG. 8C, where there is depicted an analyte 60 (not drawn to scale) bound to the surface of the nanoscale wire. Also shown, with reference to FIG. 8D, an analyte bound to the nanoscale wire may create a depletion region 62 within the nanoscale wire. In some cases, the depletion region may limit current passing through the wire. The depletion region can be depleted of holes or electrons, depending upon the type of channel Certain aspects of the present invention include a nanoscopic wire or other nanostructured material comprising one or more semiconductor and/or metal compounds, for example, for use in any of the above-described embodiments. In some cases, the semiconductors and/or metals may be chemically and/or physically combined, for example, as in a doped nanoscopic wire. The nanoscopic wire may be, for example, a nanorod, a nanowire, a nanowhisker, or a nanotube. The nanoscopic wire may be used in a device, for example, as a semiconductor component, a pathway, etc. The criteria for selection of nanoscale wires and other conductors or semiconductors for use in the invention are based, in some instances, upon whether the nanoscale wire is able to interact with an analyte, or whether the appropriate reaction entity, e.g. a binding partner, can be easily attached to the surface of the nanoscale wire, or the appropriate reaction entity, e.g. a binding partner, is near the surface of the nanoscale wire. Selection of suitable conductors or semiconductors, including nanoscale wires, will be apparent and readily reproducible by those of ordinary skill in the art with the benefit of the present disclosure.

Many nanoscopic wires as used in accordance with the present invention are individual nanoscopic wires. As used herein, "individual nanoscopic wire" means a nanoscopic wire free of contact with another nanoscopic wire (but not excluding contact of a type that may be desired between individual nanoscopic wires, e.g., as in a crossbar array). For example, an "individual" or a "free-standing" article may, at some point in its life, not be attached to another article, for example, with another nanoscopic wire, or the to free-standing article may be in solution. This is in contrast to nanotubes produced primarily by laser vaporization techniques that produce materials formed as ropes having diameters of about 2 nm to about 50 nm or more and containing many individual nanotubes. This is also in contrast to conductive portions of articles which differ from surrounding material only by having been altered chemically or physically, in situ, i.e., where a portion of a uniform article is made different from its surroundings by selective doping, etching, etc. An "individual" or a "free-standing" article is one that can be (but need not be) removed from the location where it is made, as an individual article, and transported to a different location and combined with different components to make a functional device such as those described herein and those that would be contemplated by those of ordinary skill in the art upon reading this disclosure.

In another set of embodiments, the nanoscopic wire (or other nanostructured material) may include additional materials, such as semiconductor materials, dopants, organic compounds, inorganic compounds, etc. The following are non-limiting examples of materials that may be used as dopants within the nanoscopic wire. The dopant may be an elemental semiconductor, for example, silicon, germanium, tin, selenium, tellurium, boron, diamond, or phosphorous. The dopant may also be a solid solution of various elemental semiconductors. Examples include a mixture of boron and carbon, a mixture of boron and $P(BP_6)$, a mixture of boron and silicon, a mixture of silicon and carbon, a mixture of silicon and germanium, a mixture of silicon and tin, a mixture of germanium and tin, etc. In some embodiments, the dopant may include mixtures of Group IV elements, for example, a mixture of silicon and carbon, or a mixture of silicon and germanium. In other embodiments, the dopant may include mixtures of Group III and Group V elements, for example, BN, BP, BAs, AlN, AlP, AlAs, AlSb, GaN, GaP, GaAs, GaSb, InN, InP, InAs, or InSb. Mixtures of these combinations may also be used, for example, a mixture of BN/BP/BAs, or BN/AlP. In other embodiments, the dopants may include mixtures of Group III and Group V elements. For example, the mixtures may include AlGaN, GaPAs, InPAs, GaInN, AlGaInN, GaInAsP, or the like. In other embodiments, the dopants may also include mixtures of Group II and Group VI elements. For example, the dopant may include mixtures of ZnO, ZnS, ZnSe, ZnTe, CdS, CdSe, CdTe, HgS, HgSe, HgTe, BeS, BeSe, BeTe, MgS, MgSe, or the like. Alloys or mixtures of these dopants are also be possible, to for example, ZnCdSe, or ZnSSe or the like. Additionally, mixtures of different groups of semiconductors may also be possible, for example, combinations of Group II-Group VI and Group III-Group V elements, such as $(GaAs)_x(ZnS)_{1-x}$. Other non-limiting examples of dopants may include mixtures of Group IV and Group VI elements, for example GeS, GeSe, GeTe, SnS, SnSe, SnTe, PbO, PbS, PbSe, PbTe, etc. Other dopant mixtures may include mixtures of Group I elements and Group VII elements, such as CuF, CuCl, CuBr, CuI, AgF, AgCl, AgBr, AgI, or the like. Other dopant mixtures may include different mixtures of these elements, such as $BeSiN_2$, $CaCN_2$, $ZnGeP_2$, $CdSnAs_2$, $ZnSnSb_2$, $CuGeP_3$, $CuSi_2P_3$, $Si_3N_4$, $Ge_3N_4$, $Al_2O_3$, $(Al, Ga, In)_2(S, Se, Te)_3$, $Al_2CO$, $(Cu, Ag)(Al, Ga, In, Tl, Fe)(S, Se, Te)_2$ or the like.

As a non-limiting example, a p-type dopant may be selected from Group III, and an n-type dopant may be selected from Group V. For instance, a p-type dopant may include at least one of B, Al and In, and an n-type dopant may include at least one of P, As and Sb. For Group III-Group V mixtures, a p-type dopant may be selected from Group II, including one or more of Mg, Zn, Cd and Hg, or Group IV, including one or more of C and Si. An n-type dopant may be selected from at least one of Si, Ge, Sn, S, Se and Te. It will be understood that the invention is not limited to these dopants, but may include other elements, alloys, or mixtures as well.

As used herein, the term "Group," with reference to the Periodic Table, is given its usual definition as understood by one of ordinary skill in the art. For instance, the Group II elements include Mg and Ca, as well as the Group II transition elements, such as Zn, Cd, and Hg. Similarly, the Group III elements include B, Al, Ga, In and Tl; the Group IV elements include C, Si, Ge, Sn, and Pb; the Group V elements include N, P, As, Sb and Bi; and the Group VI elements include O, S, Se, Te and Po. Combinations involving more than one element from each Group are also possible. For example, a Group II-VI material may include at least one element from Group II and at least one element from Group VI, e.g., ZnS, ZnSe, ZnSSe, ZnCdS, CdS, or CdSe. Similarly, a Group III-V material may include at least one element from Group III and at least one element from Group V, for example GaAs, GaP, GaAsP, InAs, InP, AlGaAs, or InAsP. Other dopants may also be included with these materials and combinations thereof, for example, transition metals such as Fe, Co, Te, Au, and the like. The nanoscale wire of the present invention may further include, in some cases, any organic or inorganic to molecules. In some cases, the organic or inorganic molecules are polarizable and/or have multiple charge states.

In some embodiments, at least a portion of a nanoscopic wire may be a bulk-doped semiconductor. As used herein, a "bulk-doped" article (e.g. an article, or a section or region of an article) is an article for which a dopant is incorporated substantially throughout the crystalline lattice of the article, as opposed to an article in which a dopant is only incorporated in particular regions of the crystal lattice at the atomic scale, for example, only on the surface or exterior. For example, some articles such as carbon nanotubes are typically doped after the base material is grown, and thus the dopant only extends a finite distance from the surface or exterior into the interior of the crystalline lattice. It should be understood that "bulk-doped" does not define or reflect a concentration or amount of doping in a semiconductor, nor does it necessarily indicate that the doping is uniform. In particular, in some embodiments, a bulk-doped semiconductor may comprise two or more bulk-doped regions. Thus, as used herein to describe nanoscopic wires, "doped" refers to bulk-doped nanoscopic wires, and, accordingly, a "doped nanoscopic (or nanoscale) wire" is a bulk-doped nanoscopic wire. "Heavily doped" and "lightly doped" are terms the meanings of which are understood by those of ordinary skill in the art.

In one set of embodiments, the invention includes a nanoscale wire (or other nanostructured material) that is a single crystal. As used herein, a "single crystal" item (e.g., a semiconductor) is an item that has covalent bonding, ionic bonding, or a combination thereof throughout the item. Such a single-crystal item may include defects in the crystal, but is to be distinguished from an item that includes one or more crystals, not ionically or covalently bonded, but merely in close proximity to one another.

In yet another set of embodiments, the nanoscale wire (or other nanostructured material) may comprise two or more regions having different compositions. Each region of the nanoscale wire may have any shape or dimension, and these can be the same or different between regions. For example, a region may have a smallest dimension of less than 1 micron, less than 100 nm, less than 10 nm, or less than 1 nm. In some cases, one or more regions may be a single monolayer of atoms (i.e., "delta-doping"). In certain cases, the region may be less than a single monolayer thick (for example, if some of the atoms within the monolayer are absent).

The two or more regions may be longitudinally arranged relative to each other, and/or radially arranged (e.g., as in a core/shell arrangement) within the nanoscale wire. As one example, the nanoscale wire may have multiple regions of semiconductor materials arranged longitudinally. In another example, a nanoscale wire may have two regions having different compositions arranged longitudinally, surrounded by a third region or several regions, each having a composition different from that of the other regions. As a specific example, the regions may be arranged in a layered structure within the nanoscale wire, and one or more of the regions may be delta-doped or at least partially delta-doped. As another example, the nanoscale wire may have a series of regions positioned both longitudinally and radially relative to each other. The arrangement can include a core that differs in composition along its length (changes in composition or concentration longitudinally), while the lateral (radial) dimensions of the core do, or do not, change over the portion of the length differing in composition. The shell portions can be adjacent each other (contacting each other, or defining a change in composition or concentration of a unitary shell structure longitudinally), or can be separated from each other by, for example, air, an insulator, a fluid, or an auxiliary, non-nanoscale wire component. The shell portions can be positioned directly on the core, or can be separated from the core by one or more intermediate shells portions that can themselves be constant in composition longitudinally, or varying in composition longitudinally, i.e., the invention allows the provision of any combination of a nanowire core and any number of radially-positioned shells (e.g., concentric shells), where the core and/or any shells can vary in composition and/or concentration longitudinally, any shell sections can be spaced from any other shell sections longitudinally, and different numbers of shells can be provided at different locations longitudinally along the structure.

In still another set of embodiments, a nanoscale wire may be positioned proximate the surface of a substrate, i.e., the nanoscale wire may be positioned within about 50 nm, about 25 nm, about 10 nm, or about 5 nm of the substrate. In some cases, the proximate nanoscale wire may contact at least a portion of the substrate. In one embodiment, the substrate comprises a semiconductor and/or a metal. Non-limiting examples include Si, Ge, GaAs, etc. Other suitable semiconductors and/or metals are to described above with reference to nanoscale wires. In certain embodiments, the substrate may comprise a nonmetal/nonsemiconductor material, for example, a glass, a plastic or a polymer, a gel, a thin film, etc. Non-limiting examples of suitable polymers that may form or be included in the substrate include polyethylene, polypropylene, poly(ethylene terephthalate), polydimethylsiloxane, or the like.

In certain aspects, the present invention provides a method of preparing a nanostructure. In one set of embodiments, the method involves allowing a first material to diffuse into at least part of a second material, optionally creating a new compound. For example, the first and second materials may each be metals or semiconductors, one material may be a metal and the other material may be a semiconductor, etc. In one set of embodiments, a semiconductor may be annealed to a metal. For example, a portion of the semiconductor and/or a portion of the metal may be heated such that at least some metal atoms are able to diffuse into the semiconductor, or vice versa. In one embodiment, a metal electrode (e.g., a nickel, gold, copper, silver, chromium electrode, etc.), may be positioned in physical contact with a semiconductor nanoscopic wire, and then annealed such that at least a portion of the semiconductor diffuses into at least a portion of the metal, optionally forming a metal-semiconductor compound, e.g., as disclosed in International Patent Application No. PCT/US2005/004459, filed Feb. 14, 2005, entitled "Nanostructures Containing Metal-Semiconductor Compounds," by Lieber, et al., incorporated herein by reference. For example, the semiconductor may be annealed with the metal at a temperature of about 300° C., about 350° C., about 400° C., about 450° C., about 500° C., about 550° C., or about 600° C. for a period of time of at least about 30 minutes, at least about 1 hour, at least about 2 hours, at least about 4 hours, at least about 6 hours etc. Such annealing may allow, for example, lower contact resistances or impedances between the metal and the semiconductor.

In some cases, the metal may be passivated, e.g., as described herein. For example, the metal, or at least a portion of the metal, may be exposed to one or more passivating agents, for example, $Si_3N_4$. Insulation of the metal by the passivating agent may be used to form a layer covering the surface of the metal, for example, to prevent reaction or nonspecific binding between an analyte and the metal. For instance, a metal electrode may be in electrical communication with a semiconductor comprising one or more immobilized reaction entities, and the metal electrode may be passivated to prevent a reaction or nonspecific binding between the metal and the reaction entity, and/or to reduce or prevent leakage current from the metal. In some cases, the passivation may be conducted at a relatively high temperature, for example, within a plasma CVD chamber.

In certain embodiments, the present invention involves controlling and altering the doping of semiconductors in a nanoscale wire. In some cases, the nanoscale wires (or other nanostructure) may be produced using techniques that allow for direct and controlled growth of the nanoscale wires. In some cases, the nanoscale wire may be doped during growth of the nanoscale wire. Doping the nanoscale wire during growth may result in the property that the doped nanoscale wire is bulk-doped. Furthermore, such doped nanoscale wires may be controllably doped, such that a concentration of a dopant within the doped nanoscale wire can be controlled and therefore reproduced consistently.

Certain arrangements may utilize metal-catalyzed CVD techniques ("chemical vapor deposition") to synthesize individual nanoscale wires. CVD synthetic procedures useful for preparing individual wires directly on surfaces and in bulk form are generally known, and can readily be carried out by those of ordinary skill in the art. Nanoscopic wires may also be grown through laser catalytic growth. With the same basic principles as LCG, if uniform diameter nanoclusters (less than 10% to 20% variation depending on how uniform the nanoclusters are) are used as the catalytic cluster, nanoscale wires with uniform size (diameter) distribution can be produced, where the diameter of the wires is determined by the size of the catalytic clusters. By controlling growth time, nanoscale wires with different lengths can be grown.

One technique that may be used to grow nanoscale wires is catalytic chemical vapor deposition ("C-CVD"). In C-CVD, reactant molecules are formed from the vapor phase. Nanoscale wires may be doped by introducing the doping element into the vapor phase reactant (e.g. diborane and phosphane). The doping concentration may be controlled by controlling the relative amount of the doping compound introduced in the composite target. The final doping concentration or ratios are not necessarily the same as the vapor-phase concentration or ratios. By controlling growth conditions, such as temperature, pressure or the like, nanoscale wires having the same doping concentration may be produced.

Another technique for direct fabrication of nanoscale wire junctions during synthesis is referred to as laser catalytic growth ("LCG"). In LCG, dopants are controllably introduced during vapor phase growth of nanoscale wires. Laser vaporization of a composite target composed of a desired material (e.g. silicon or indium phosphide) and a catalytic material (e.g. a nanoparticle catalyst) may create a hot, dense vapor. The vapor may condense into liquid nanoclusters through collision with a buffer gas. Growth may begin when the liquid nanoclusters become supersaturated with the desired phase and can continue as long as reactant is available. Growth may terminate when the nanoscale wire passes out of the hot reaction zone and/or when the temperature is decreased. The nanoscale wire may be further subjected to different semiconductor reagents during growth.

Other techniques to produce nanoscale semiconductors such as nanoscale wires are also contemplated. For example, nanoscale wires of any of a variety of materials may be grown directly from vapor phase through a vapor-solid process. Also, nanoscale wires may also be produced by deposition on the edge of surface steps, or other types of patterned surfaces. Further, nanoscale wires may be grown by vapor deposition in or on any generally elongated template. The porous membrane may be porous silicon, anodic alumina, a diblock copolymer, or any other similar structure. The natural fiber may be DNA molecules, protein molecules carbon nanotubes, any other elongated structures. For all the above described techniques, the source materials may be a solution or a vapor. In some cases, while in solution phase, the template may also include be column micelles formed by surfactant.

In some cases, the nanoscale wire may be doped after formation. In one technique, a nanoscale wire having a substantially homogeneous composition is first synthesized, then is doped post-synthetically with various dopants. Such doping may occur throughout the entire nanoscale wire, or in one or more portions of the nanoscale wire, for example, in a wire having multiple regions differing in composition.

One aspect of the invention provides for the assembly, or controlled placement, of nanoscale wires on a surface. Any substrate may be used for nanoscale wire placement, for example, a substrate comprising a semiconductor, a substrate comprising a metal, a substrate comprising a glass, a substrate comprising a polymer, a substrate to comprising a gel, a substrate that is a thin film, a substantially transparent substrate, a non-planar substrate, a flexible substrate, a curved substrate, etc. In some cases, assembly can be carried out by aligning nanoscale wires using an electrical field. In other cases, assembly can be performed using an arrangement involving positioning a fluid flow directing apparatus to direct fluid containing suspended nanoscale wires toward and in the direction of alignment with locations at which nanoscale wires are desirably positioned.

In certain cases, a nanoscale wire (or other nanostructure) is formed on the surface of a substrate, and/or is defined by a feature on a substrate. In one example, a nanostructure, such as a nanoscale wire, is formed as follows. A substrate is imprinted using a stamp or other applicator to define a pattern, such as a nanoscale wire or other nanoscale structure. After removal of the stamp or other applicator, at least a portion of the imprintable layer is removed, for example, through etching processes such as reactive ion etching (RIE), or other known techniques. In some cases, enough imprintable material may be removed from the substrate so as to expose portions of the substrate free of the imprintable material. A metal or other materials may then be deposited onto at least a portion of the substrate, for example, gold, copper, silver, chromium, etc. In some cases, a "lift-off" step may then be performed, where at least a portion of the imprintable material is removed from the substrate. Metal or other material deposited onto the imprintable material may be removed along with the removal of the imprintable material, for example, to form one or more nanoscale wires. Structures deposited on the surface may be connected to one or more electrodes in some cases. The substrate may be any suitable substrate that can support an imprintable layer, for example, comprising a semiconductor, a metal, a glass, a polymer, a gel, etc. In some cases, the substrate may be a thin film, substantially transparent, non-planar, flexible, and/or curved, etc.

In certain cases, an array of nanoscale wires may be produced by providing a surface having a plurality of substantially aligned nanoscale wires, and removing, from the surface, a portion of one or more of the plurality of nanoscale wires. The remaining nanoscale wires on the surface may then be connected to one or more electrodes. In certain cases, the nanoscopic wires are arranged such that they are in contact with each other; in other instances, however, the aligned nanoscopic wires may be at a pitch such that they are substantially not in physical contact.

In certain cases, nanoscale wires are positioned proximate a surface using flow techniques, i.e., techniques where one or more nanoscale wires may be carried by a fluid to a substrate. Nanoscale wires (or any other elongated structures) can be aligned by inducing a flow of a nanoscale wire solution on surface, where the flow can include channel flow or flow by any other suitable technique. Nanoscale wire arrays with controlled position and periodicity can be produced by patterning a surface of a substrate and/or conditioning the surface of the nanoscale wires with different functionalities, where the position and periodicity control may be achieved by designing specific complementary forces between the patterned surface and the nanoscale wires. Nanoscale wires can also be assembled using a Langmuir-Blodgett (LB) trough. Nanoscale wires may first be surface-conditioned and dispersed to the surface of a liquid phase to form a Langmuir-Blodgett film. In some cases, the liquid may include a surfactant, which can, in some cases, reduce aggregation of the nanoscale wires and/or reduce the ability of the nanoscale wires to interact with each other. The nanoscale wires can be aligned into different patterns (such as parallel arrays or fibers) by compressing the surface or reducing the surface area of the surface.

Another arrangement involves forming surfaces on a substrate including regions that selectively attract nanoscale wires surrounded by regions that do not selectively attract them. Surfaces can be patterned using known techniques such as electron-beam patterning, "soft-lithography" such as that described in International Patent Application Serial No. PCT/US96/03073, entitled "Microcontact Printing on Surfaces and Derivative Articles," filed Mar. 1, 1996, published as Publication No. WO 96/29629 on Jul. 26, 1996; or U.S. Pat. No. 5,512,131, entitled "Formation of Microstamped Patterns on Surfaces and Derivative Articles," issued Apr. 30, 1996, each of which is incorporated herein by reference. Additional techniques are described in U.S. Patent Application Ser. No. 60/142,216, entitled "Molecular Wire-Based Devices and Methods of Their Manufacture," filed Jul. 2, 1999, incorporated herein by reference. Fluid flow channels can be created at a size scale advantageous for placement of nanoscale wires on surfaces using a variety of techniques such as those described in International Patent Application Serial No. PCT/US97/04005, entitled "Method of Forming Articles and Patterning Surfaces via Capillary Micromolding," filed Mar. 14, 1997, published as Publication No. WO 97/33737 on Sep. 18, 1997, and incorporated herein by reference. Other to techniques include those described in U.S. Pat. No. 6,645,432, entitled "Microfluidic Systems Including Three-dimensionally Arrayed Channel Networks," issued Nov. 11, 2003, incorporated herein by reference.

Chemically patterned surfaces other than SAM-derivatized surfaces can be used, and many techniques for chemically patterning surfaces are known. Another example of a chemically patterned surface may be a micro-phase separated block copolymer structure. These structures may provide a stack of dense lamellar phases, where a cut through these phases reveals a series of "lanes" wherein each lane represents a single layer. The assembly of nanoscale wires onto substrate and electrodes can also be assisted using bimolecular recognition in some cases. For example, one biological binding partner may be immobilized onto the nanoscale wire surface and the other one onto a substrate or an electrode using physical adsorption or covalently linking. An example technique which may be used to direct the assembly of a nanoscopic wires on a substrate is by using "SAMs," or self-assembled monolayers. Any of a variety of substrates and SAM-forming material can be used along with microcontact printing techniques, such as those described in International Patent Application Serial No. PCT/US96/03073, entitled "Microcontact Printing on Surfaces and Derivative Articles,"

filed Mar. 1, 1996, published as Publication No. WO 96/29629 on Jul. 26, 1996, incorporated herein by reference in its entirety.

In some cases, the nanoscale wire arrays may also be transferred to another substrate, e.g., by using stamping techniques. In certain instances, nanoscale wires may be assembled using complementary interaction, i.e., where one or more complementary chemical, biological, electrostatic, magnetic or optical interactions are used to position one or more nanoscale wires on a substrate. In certain cases, physical patterns may be used to position nanoscale wires proximate a surface. For example, nanoscale wires may be positioned on a substrate using physical patterns, for instance, aligning the nanoscale wires using corner of the surface steps or along trenches on the substrate.

In one aspect, the present invention provides any of the above-mentioned devices packaged in kits, optionally including instructions for use of the devices. As used herein, "instructions" can define a component of instructional utility (e.g., directions, guides, warnings, labels, notes, FAQs ("frequently asked questions"), etc., and typically involve written instructions on or associated with packaging of the invention. Instructions can to also include instructional communications in any form (e.g., oral, electronic, digital, optical, visual, etc.), provided in any manner such that a user will clearly recognize that the instructions are to be associated with the device, e.g., as discussed herein. Additionally, the kit may include other components depending on the specific application, for example, containers, adapters, syringes, needles, replacement parts, etc. As used herein, "promoted" includes all methods of doing business including, but not limited to, methods of selling, advertising, assigning, licensing, contracting, instructing, educating, researching, importing, exporting, negotiating, financing, loaning, trading, vending, reselling, distributing, replacing, or the like that can be associated with the methods and compositions of the invention, e.g., as discussed herein. Promoting may also include, in some cases, seeking approval from a government agency to sell a composition of the invention for medicinal purposes. Methods of promotion can be performed by any party including, but not limited to, businesses (public or private), contractual or subcontractual agencies, educational institutions such as colleges and universities, research institutions, hospitals or other clinical institutions, governmental agencies, etc. Promotional activities may include instructions or communications of any form (e.g., written, oral, and/or electronic communications, such as, but not limited to, e-mail, telephonic, facsimile, Internet, Web-based, etc.) that are clearly associated with the invention.

DEFINITIONS

The following definitions will aid in the understanding of the invention. Certain devices of the invention may include wires or other components of scale commensurate with nanometer-scale wires, which includes nanotubes and nanowires. In some embodiments, however, the invention comprises articles that may be greater than nanometer size (e.g., micrometer-sized). As used herein, "nanoscopic-scale," "nanoscopic," "nanometer-scale," "nanoscale," the "nano-" prefix (for example, as in "nanostructured"), and the like generally refers to elements or articles having widths or diameters of less than about 1 micron, and less than about 100 nm in some cases. In all embodiments, specified widths can be a smallest width (i.e. a width as specified where, at that location, the article can have a larger width in a different dimension), or a largest width (i.e. where, at that location, the article has a width that is no wider than as specified, but can have a length that is greater).

As used herein, a "wire" generally refers to any material having a conductivity of or of similar magnitude to any semiconductor or any metal, and in some embodiments may be used to connect two electronic components such that they are in electronic communication with each other. For example, the terms "electrically conductive" or a "conductor" or an "electrical conductor" when used with reference to a "conducting" wire or a nanoscale wire, refers to the ability of that wire to pass charge. Typically, an electrically conductive nanoscale wire will have a resistivity comparable to that of metal or semiconductor materials, and in some cases, the electrically conductive nanoscale wire may have lower resistivities, for example, resistivities of less than about 100 microOhm cm ($\mu\Omega$ cm). In some cases, the electrically conductive nanoscale wire will have a resistivity lower than about $10^{-3}$ ohm meters, lower than about $10^{-4}$ ohm meters, or lower than about $10^{-6}$ ohm meters or $10^{-7}$ ohm meters.

A "semiconductor," as used herein, is given its ordinary meaning in the art, i.e., an element having semiconductive or semi-metallic properties (i.e., between metallic and non-metallic properties). An example of a semiconductor is silicon. Other non-limiting examples include gallium, germanium, diamond (carbon), tin, selenium, tellurium, boron, or phosphorous.

A "nanoscopic wire" (also known herein as a "nanoscopic-scale wire" or "nanoscale wire") generally is a wire, that at any point along its length, has at least one cross-sectional dimension and, in some embodiments, two orthogonal cross-sectional dimensions less than 1 micron, less than about 500 nm, less than about 200 nm, less than about 150 nm, less than about 100 nm, less than about 70, less than about 50 nm, less than about 20 nm, less than about 10 nm, or less than about 5 nm. In other embodiments, the cross-sectional dimension can be less than 2 nm or 1 nm. In one set of embodiments, the nanoscale wire has at least one cross-sectional dimension ranging from 0.5 nm to 100 nm or 200 nm. In some cases, the nanoscale wire is electrically conductive. Where nanoscale wires are described having, for example, a core and an outer region, the above dimensions generally relate to those of the core. The cross-section of a nanoscopic wire may be of any arbitrary shape, including, but not limited to, circular, square, rectangular, annular, polygonal, or elliptical, and may be a regular or an irregular shape. The nanoscale wire may be solid or hollow. A non-limiting list of examples of materials to from which nanoscale wires of the invention can be made appears below. Any nanoscale wire can be used in any of the embodiments described herein, including carbon nanotubes, molecular wires (i.e., wires formed of a single molecule), nanorods, nanowires, nanowhiskers, organic or inorganic conductive or semiconducting polymers, and the like, unless otherwise specified. Other conductive or semiconducting elements that may not be molecular wires, but are of various small nanoscopic-scale dimensions, can also be used in some instances, e.g. inorganic structures such as main group and metal atom-based wire-like silicon, transition metal-containing wires, gallium arsenide, gallium nitride, indium phosphide, germanium, cadmium selenide, etc. A wide variety of these and other nanoscale wires can be grown on and/or applied to surfaces in patterns useful for electronic devices in a manner similar to techniques described herein involving the specific nanoscale wires used as examples, without undue experimentation. The nanoscale wires, in some cases, may be formed having dimensions of at least about 1 micron, at least about 3 microns, at least about 5 microns, or at least about 10 microns or about 20 microns in length, and can be less than about 100 nm, less than about 80 nm, less than about 60 nm, less than about 40 nm, less than about 20 nm, less than about 10 nm, or less than about 5 nm in thickness (height and width). The nanoscale wires may have an aspect ratio (length to thickness) of greater than about 2:1, greater than about 3:1, greater than about 4:1, greater than about 5:1, greater than about 10:1, greater than about 25:1, greater than about 50:1, greater than about 75:1, greater than about 100:1, greater than about 150:1, greater than about 250:1, greater than about 500:1, greater than about 750:1, or greater than about 1000:1 or more in some cases.

A "nanowire" (e.g. comprising silicon and/or another semiconductor material) is a nanoscopic wire that is typically a solid wire, and may be elongated in some cases. Preferably, a nanowire (which is abbreviated herein as "NW") is an elongated semiconductor, i.e., a nanoscale semiconductor. A "non-nanotube nanowire" is any nanowire that is not a nanotube. In one set of embodiments of the invention, a non-nanotube nanowire having an unmodified surface (not including an auxiliary reaction entity not inherent in the nanotube in the environment in which it is positioned) is used in any arrangement of the invention described herein in which a nanowire or nanotube can be used.

As used herein, a "nanotube" (e.g. a carbon nanotube) is a nanoscopic wire that is hollow, or that has a hollowed-out core, including those nanotubes known to those of ordinary skill in the art. "Nanotube" is abbreviated herein as "NT." Nanotubes are used as one example of small wires for use in the invention and, in certain embodiments, devices of the invention include wires of scale commensurate with nanotubes. Examples of nanotubes that may be used in the present invention include, but are not limited to, single-walled nanotubes (SWNTs). Structurally, SWNTs are formed of a single graphene sheet rolled into a seamless tube. Depending on the diameter and helicity, SWNTs can behave as one-dimensional metals and/or semiconductors. SWNTs. Methods of manufacture of nanotubes, including SWNTs, and characterization are known. Methods of selective functionalization on the ends and/or sides of nanotubes also are known, and the present invention makes use of these capabilities for molecular electronics in certain embodiments. Multi-walled nanotubes are well known, and can be used as well.

As used herein, an "elongated" article (e.g. a semiconductor or a section thereof) is an article for which, at any point along the longitudinal axis of the article, the ratio of the length of the article to the largest width at that point is greater than 2:1.

A "width" of an article, as used herein, is the distance of a straight line from a point on a perimeter of the article, through the center of the article, to another point on the perimeter of the article. As used herein, a "width" or a "cross-sectional dimension" at a point along a longitudinal axis of an article is the distance along a straight line that passes through the center of a cross-section of the article at that point and connects two points on the perimeter of the cross-section. The "cross-section" at a point along the longitudinal axis of an article is a plane at that point that crosses the article and is orthogonal to the longitudinal axis of the article. The "longitudinal axis" of an article is the axis along the largest dimension of the article. Similarly, a "longitudinal section" of an article is a portion of the article along the longitudinal axis of the article that can have any length greater than zero and less than or equal to the length of the article. Additionally, the "length" of an elongated article is a distance along the longitudinal axis from end to end of the article.

As used herein, a "cylindrical" article is an article having an exterior shaped like a cylinder, but does not define or reflect any properties regarding the interior of the to article. In other words, a cylindrical article may have a solid interior, may have a hollowed-out interior, etc. Generally, a cross-section of a cylindrical article appears to be circular or approximately circular, but other cross-sectional shapes are also possible, such as a hexagonal shape. The cross-section may have any arbitrary shape, including, but not limited to, square, rectangular, or elliptical. Regular and irregular shapes are also included.

As used herein, an "array" of articles (e.g., nanoscopic wires) comprises a plurality of the articles, for example, a series of aligned nanoscale wires, which may or may not be in contact with each other. As used herein, a "crossed array" or a "crossbar array" is an array where at least one of the articles contacts either another of the articles or a signal node (e.g., an electrode).

The invention provides, in certain embodiments, a nanoscale wire or wires forming part of a system constructed and arranged to determine an analyte in a sample to which the nanoscale wire(s) is exposed. "Determine," in this context, generally refers to the analysis of a species, for example, quantitatively or qualitatively, and/or the detection of the presence or absence of the species. "Determining" may also refer to the analysis of an interaction between two or more species, for example, quantitatively or qualitatively, and/or by detecting the presence or absence of the interaction, e.g. determination of the binding between two species. As an example, an analyte may cause a determinable change in an electrical property of a nanoscale wire (e.g., electrical conductivity, resistivity, impedance, etc.), a change in an optical property of the nanoscale wire, etc. Examples of determination techniques include, but are not limited to, piezoelectric measurement, electrochemical measurement, electromagnetic measurement, photodetection, mechanical measurement, acoustic measurement, gravimetric measurement, and the like. "Determining" also means detecting or quantifying interaction between species.

A "fluid," as used herein, generally refers to a substance that tends to flow and to conform to the outline of its container. Typically, fluids are materials that are unable to withstand a static shear stress. When a shear stress is applied to a fluid, it experiences a continuing and permanent distortion. Typical fluids include liquids and gases, but may also include free-flowing solid particles, viscoelastic fluids, and the like.

As used herein, a component that is "immobilized relative to" another component to either is fastened to the other component or is indirectly fastened to the other component, e.g., by being fastened to a third component to which the other component also is fastened. For example, a first entity is immobilized relative to a second entity if a species fastened to the surface of the first entity attaches to an entity, and a species on the surface of the second entity attaches to the same entity, where the entity can be a single entity, a complex entity of multiple species, another particle, etc. In certain embodiments, a component that is immobilized relative to another component is immobilized using bonds that are stable, for example, in solution or suspension. In some embodiments, non-specific binding of a component to another component, where the components may easily separate due to solvent or thermal effects, is not preferred.

As used herein, "fastened to or adapted to be fastened to," as used in the context of a species relative to another species or a species relative to a surface of an article (such as a nanoscale wire), or to a surface of an article relative to another surface, means that the species and/or surfaces are chemically or biochemically linked to or adapted to be linked to, respectively, each other via covalent attachment, attachment via specific biological binding (e.g., biotin/streptavidin), coordinative bonding such as chelate/metal binding, or the like. For example, "fastened" in this context includes multiple chemical linkages, multiple chemical/biological linkages, etc., including, but not limited to, a binding species such as a peptide synthesized on a nanoscale wire, a binding species specifically biologically coupled to an antibody which is bound to a protein such as protein A, which is attached to a nanoscale wire, a binding species that forms a part of a molecule, which in turn is specifically biologically bound to a binding partner covalently fastened to a surface of a nanoscale wire, etc. A species also is adapted to be fastened to a surface if a surface carries a particular nucleotide sequence, and the species includes a complementary nucleotide sequence.

"Specifically fastened" or "adapted to be specifically fastened" means a species is chemically or biochemically linked to or adapted to be linked to, respectively, another specimen or to a surface as described above with respect to the definition of "fastened to or adapted to be fastened," but excluding essentially all non-specific binding. "Covalently fastened" means fastened via essentially nothing other than one or more covalent bonds.

The term "binding" refers to the interaction between a corresponding pair of to molecules or surfaces that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones and the like. Specific non-limiting examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, virus/cell surface receptor, etc.

The term "binding partner" refers to a molecule that can undergo binding with a particular molecule. Biological binding partners are examples. For example, Protein A is a binding partner of the biological molecule IgG, and vice versa. Other non-limiting examples include nucleic acid-nucleic acid binding, nucleic acid-protein binding, protein-protein binding, enzyme-substrate binding, receptor-ligand binding, receptor-hormone binding, antibody-antigen binding, etc. Binding partners include specific, semi-specific, and non-specific binding partners as known to those of ordinary skill in the art. For example, Protein A is usually regarded as a "non-specific" or semi-specific binder. The term "specifically binds," when referring to a binding partner (e.g., protein, nucleic acid, antibody, etc.), refers to a reaction that is determinative of the presence and/or identity of one or other member of the binding pair in a mixture of heterogeneous molecules (e.g., proteins and other biologics). Thus, for example, in the case of a receptor/ligand binding pair the ligand would specifically and/or preferentially select its receptor from a complex mixture of molecules, or vice versa. An enzyme would specifically bind to its substrate, a nucleic acid would specifically bind to its complement, an antibody would specifically bind to its antigen. Other examples include nucleic acids that specifically bind (hybridize) to their complement, antibodies specifically bind to their antigen, binding pairs such as those described above, and the like. The binding may be by one or more of a variety of mechanisms including, but not limited to ionic interactions, and/or covalent interactions, and/or hydrophobic interactions, and/or van der Waals interactions, etc.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

As used herein, terms such as "polynucleotide" or "oligonucleotide" or grammatical equivalents generally refer to a polymer of at least two nucleotide bases covalently linked together, which may include, for example, but not limited to, natural nucleosides (e.g., adenosine, thymidine, guanosine, cytidine, uridine, deoxyadenosine, deoxythymidine, deoxyguanosine and deoxycytidine), nucleoside analogs (e.g., 2-aminoadenosine, 2-thiothymidine, inosine, pyrrolopyrimidinez, 3-methyladenosine, C5-bromouridine, C5-fluorouridine, C5-iodouridine, C5-propynyluridine, C5-propynylcytidine, C5-methylcytidine, 7-deazaadenosinez, 7-deazaguanosine, 8-oxoadenosine, 8-oxoguanosine, 06-methylguanosine, 2-thiocytidine, 2-aminopurine, 2-amino-6-chloropurine, 2,6-diaminopurine, hypoxanthine), chemically or biologically modified bases (e.g., methylated bases), intercalated bases, modified sugars (2'-fluororibose, arabinose, or hexose), modified phosphate moieties (e.g., phosphorothioates or 5'-N-phosphoramidite linkages), and/or other naturally and non-naturally occurring bases substitutable into the polymer, including substituted and unsubstituted aromatic moieties. Other suitable base and/or polymer modifications are well-known to those of skill in the art. Typically, an "oligonucleotide" is a polymer having 20 bases or less, and a "polynucleotide" is a polymer having at least 20 bases. Those of ordinary skill in the art will recognize that these terms are not precisely defined in terms of the number of bases present within the polymer strand.

A "nucleic acid," as used herein, is given its ordinary meaning as used in the art. Nucleic acids can be single-stranded or double stranded, and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469, 863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp. 169-176). Several nucleic acid analogs are described in Rawls, *Chemical & Engineering News*, Jun. 2, 1997 page 35. These modifications of the ribose-phosphate backbone may be done to facilitate the addition of additional moieties such as labels, or to increase the stability and half-life of such molecules in physiological environments.

As used herein, an "antibody" refers to a protein or glycoprotein including one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well characterized fragments produced by digestion with various peptidases. Thus, for example, pepsin digests an antibody below (i.e. toward the Fc domain) the disulfide linkages in the hinge region to produce F(ab)'2, a dimer of Fab which itself is a light chain joined to $V_H$-$C_H$1 by a disulfide bond. The F(ab)'2 may be reduced under mild conditions to break the disulfide linkage in the hinge region thereby converting the (Fab')$_2$ dimer into an Fab' monomer. The Fab' monomer is essentially a Fab with part of the hinge region (see, Paul (1993) *Fundamental Immunology*, Raven Press, N.Y. for a more detailed description of other antibody fragments). While various antibody fragments are defined in terms of the digestion of an intact antibody, one of skill will appreciate that such fragments may be synthesized de novo either chemically, by utilizing recombinant DNA methodology, or by "phage display" methods (see, e.g., Vaughan et al. (1996) *Nature Biotechnology*, 14(3): 309-314, and PCT/US96/10287). Preferred antibodies include single chain antibodies, e.g., single chain Fv (scFv) antibodies in which a variable heavy and a variable light chain are joined together (directly or through a peptide linker) to form a continuous polypeptide.

The term "quantum dot" is known to those of ordinary skill in the art, and generally refers to semiconductor or metal nanoparticles that absorb light and quickly re-emit light in a different color depending on the size of the dot. For example, a 2 nanometer quantum dot emits green light, while a 5 nanometer quantum dot emits red light. Cadmium selenide quantum dot nanocrystals are available from Quantum Dot Corporation of Hayward, Calif.

The following documents are incorporated herein by reference in their entirety for all purposes, and include additional description of teachings usable with the present invention: U.S. Provisional Patent Application Ser. No. 60/142,216, filed Jul. 2, 1999, entitled "Molecular Wire-Based Devices and Methods of Their Manufacture," by Lieber, et al.; International Patent Application No. PCT/US00/18138, filed Jun. 30, 2000, entitled "Nanoscopic Wire-Based Devices, Arrays, and Methods of Their Manufacture," by Lieber, et al., published as WO 01/03208 on Jan. 11, 2001; U.S. Provisional Patent Application Ser. No. 60/226,835, filed Aug. 22, 2000, entitled "Semiconductor Nanowires," by Lieber, et al.; U.S. Provisional Patent Application Ser. No. 60/254,745, filed Dec. 11, 2000, entitled "Nanowire and Nanotube Nanosensors," by Lieber, et al.; U.S. Provisional Patent Application Ser. No. 60/291,896, filed May 18, 2001, entitled "Nanowire Devices Including Emissive Elements and Sensors," by Lieber, et al.; U.S. Provisional Patent Application Ser. No. 60/292,035, filed May 18, 2001, entitled "Nanowire and Nanotube Sensors," by Lieber, et al.; U.S. Provisional Patent Application Ser. No. 60/292,045, filed May 18, 2001, entitled "Nanowire Electronic Devices Including Memory and Switching Devices," by Lieber, et al.; U.S. Provisional Patent Application Ser. No. 60/292,121, filed May 18, 2001, entitled "Semiconductor Nanowires," by Lieber, et al.; U.S. patent application Ser. No. 09/935,776, filed Aug. 22, 2001, entitled "Doped Elongated Semiconductors, Growing Such Semiconductors, Devices Including Such Semiconductors, and Fabricating Such Devices," by Lieber, et al., published as U.S. Patent Application Publication No. 2002/0130311 on Sep. 19, 2002; International Patent Application No. PCT/US01/26298, filed Aug. 22, 2001, entitled "Doped Elongated Semiconductors, Growing Such Semiconductors, Devices Including Such Semiconductors, and Fabricating Such Devices," by Lieber, et al., published as WO 02/17362 on Feb. 28, 2002; U.S. patent application Ser. No. 10/033,369, filed Oct. 24, 2001, entitled "Nanoscopic Wire-Based Devices and Arrays," by Lieber, et al., published as U.S. Patent Application Publication No. 2002/0130353 on Sep. 19, 2002, now U.S. Pat. No. 6,781,166, issued Aug. 24, 2004; U.S. Provisional Patent Application Ser. No. 60/348,313, filed Nov. 9, 2001, entitled "Transistors, Diodes, Logic Gates and Other Devices Assembled from Nanowire Building Blocks," by Lieber, et al.; U.S. patent application Ser. No. 10/020,004, filed Dec. 11, 2001, entitled "Nanosensors," by Lieber, et al., published as U.S. Patent Application Publication No. 2002/0117659 on Aug. 29, 2002; International Patent Application No. PCT/US01/48230, filed Dec. 11, 2001, entitled "Nanosensors," by Lieber, et al., published as WO 02/48701 on Jun. 20, 2002; U.S. Provisional Patent Application Ser. No. 60/354,642, filed Feb. 6, 2002, entitled "Nanowire Devices Including Emissive Elements and Sensors," by Lieber, et al.; U.S. patent application Ser. No. 10/152,490, filed May 20, 2002, entitled "Nanoscale Wires and Related Devices," by Lieber, et al.; International Patent Application No. PCT/US02/16133, filed May 20, 2002, entitled "Nanoscale Wires and Related Devices," by Lieber, et al., published as WO 03/005450 on Jan. 16, 2003; U.S. patent application Ser. No. 10/196,337, filed Jul. 16, 2002, entitled "Nanoscale Wires and Related Devices," by Lieber, et al., published as U.S. Patent Application Publication No. 2003/0089899 on May 15, 2003; U.S. Provisional Patent Application Ser. No. 60/397,121, filed Jul. 19, 2002, entitled "Nanowire Coherent Optical Components," by Lieber, et al.; International Patent Application No. PCT/US03/22061, filed Jul. 16, 2003, entitled "Nanoscale Wires and Related Devices," by Lieber, et al.; U.S. patent application Ser. No. 10/624,135, filed Jul. 21, 2003, entitled "Nanowire Coherent Optical Components," by Lieber, et al.; International Patent Application No. PCT/US03/11078, filed Jul. 21, 2003, entitled "Nanowire Coherent Optical Components," by Lieber, et al., published as WO 2004/010552 on Jan. 29, 2004; U.S. Provisional Patent Application Ser. No. 60/524,301, filed Nov. 20, 2003, entitled "Nanoscale Arrays and Related Devices," by Whang, et al.; U.S. patent application Ser. No. 10/720,020, filed Nov. 21, 2003, entitled "Nanoscale Wires and Related Devices," by Lieber, et al., published as U.S. Patent Application Publication No. 2003/0089899 on May 15, 2003; U.S. patent application Ser. No. 10/734,086, filed Dec. 11, 2003, entitled "Nanowire Coherent Optical Components," by Lieber, et al., published as U.S. Patent Application Publication No. 2004/0213307 on Oct. 28, 2004; U.S. Provisional Patent Application Ser. No. 60/544,800, filed Feb. 13, 2004, entitled "Nanostructures Containing Metal-Semiconductor Compounds," by Lieber, et al.; U.S. Provisional Patent Application Ser. No. 60/551,634, filed Mar. 8, 2004, entitled "Robust Nanostructures," by McAlpine, et al.; U.S. patent application Ser. No. 10/812,653, filed Mar. 29, 2004, entitled "Nanoscopic Wire-Based Devices and Arrays," by Lieber, et al., published as U.S. Patent Application Publication No. 2004/0188721 on Sep. 30, 2004; U.S. Provisional Patent Application Ser. No. 60/579,996, filed Jun. 15, 2004, entitled "Nanosensors," by Wang, et al.; U.S. patent application Ser. No. 10/973,665, filed Oct. 26, 2004, entitled "Nanoscopic Wire-Based Devices and Arrays," by Lieber, et al., published as U.S. Patent Application Publication No. 2005/0117441 on Jun. 2, 2005; U.S. patent application Ser. No. 10/995,075, filed Nov. 22, 2004, entitled "Nanoscale Arrays and Related Devices," by Whang, et al., published as U.S. Patent Application Publication No. 2005/0253137 on Nov. 17, 2005; U.S. Provisional Patent Application Ser. No. 60/633,733, filed Dec. 6, 2004, entitled "Nanoscale Wire Based Data Storage," by Lieber, et al.; U.S. patent application Ser. No. 11/058,443, filed Feb. 14, 2005, entitled "Nanoscale Wires and Related Devices," by Lieber, et al.; International Patent Application No. PCT/US2005/004459, filed Feb. 14, 2005, entitled "Nanostructures Containing Metal-Semiconductor Compounds," by Lieber, et al., published as WO 2005/093831 on Oct. 6, 2005; U.S. patent application Ser. No. 11/082,372, filed Mar. 17, 2005, entitled "Doped Elongated Semiconductors, Growing Such Semiconductors, Devices Including Such Semiconductors, and Fabricating Such Devices," by Lieber, et al., published as U.S. Patent Application Publication No. 2005/0164432 on Jul. 28, 2005; U.S. patent application Ser. No. 11/137,784, filed May 25, 2005, entitled "Nanoscale Sensors," by Lieber, et al.; U.S. Provisional Patent Application Ser. No. 60/707,136, filed Aug. 9, 2005, entitled "Nanoscale Sensors," by Lieber, et al.; U.S. Provisional Patent Application Ser. No. 60/790,322, filed Apr. 7, 2006, entitled "Nanoscale Wire Methods and Devices," by Lieber, et al.; and U.S. Provisional Patent Application Ser. No. 60/812,884, filed Jun. 12, 2006, entitled "Nanosensors and Related Technologies," by Lieber, et al.

The following examples are intended to illustrate certain embodiments of the present invention, but do not exemplify the full scope of the invention.

Example 1

This example illustrates the design and characteristics of an array, according to one embodiment of the invention. The conversion of silicon nanowire field-effect transistors into sensors for cancer protein marker detection was carried out by attaching monoclonal antibodies to the nanowire surfaces following device fabrication. The basic linkage chemistry is as follows. First, aldehyde propyltrimethoxysilane (APTMS) was coupled to oxygen plasma-cleaned silicon nanowire surfaces in order to present terminal aldehyde groups at the nanowire surface. Second, aldehyde groups were coupled to the monoclonal antibodies, and third, unreacted free aldehyde groups were blocked by reaction with ethanolamine. These studies thus show that the surface chemistry may affect the nanowire device sensitivity and selectivity.

The basic sensor chip (FIGS. 9A and 10) included integrated electrically addressable silicon nanowires with the potential for about 200 individually addressable devices. This particular chip allowed the incorporation of different types of addressable nanowires, for example p-type and/or n-type doped silicon nanowires, during fabrication steps to form the addressable electrical contacts; that is, solutions of different nanowires can be sequentially assembled in different regions of the device, and electrical contacts formed in parallel by photolithography and metal deposition steps.

The nanowire arrays were fabricated as follows. The silicon nanowires were synthesized by chemical vapor deposition using 20 nm gold nanoclusters as catalysts, silane as reactant. For p-type silicon nanowires, diborane was used as dopant, with a B:Si ratio of 1:4000; for n-type silicon nanowires, phosphine was used as dopant, with a P:Si ratio of 1:4000. Arrays of silicon nanowire devices were defined using photolithography with Ni metal contacts on silicon substrates with 600 nm thick oxide layer. The metal contacts were passivated by subsequent deposition of a roughly 50 nm thick $Si_3N_4$ coating. The spacing between source-drain electrodes (active sensor area) was 2 microns in all experiments. The protein samples were delivered to the nanowire device arrays using fluidic channels formed by a flexible PDMS polymer channel sealed to the device chip, and samples were delivered through inlet/outlet connection in the polymer.

Figure 9A:
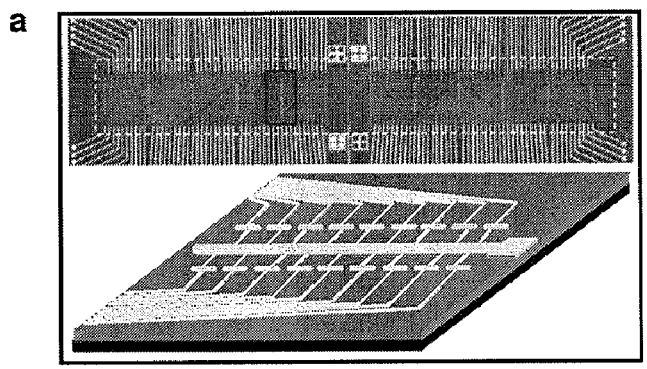
FIGS. 9A-9E illustrate various nanoscale wire sensors and some of their to properties, according to certain embodiments of the invention.

FIG. 9A is an optical image (top) of the device. The white line features in the image correspond to the silicon nitride passivated metal electrodes that connect to individual nanowire devices. The rectangle highlights one of the repeated (vertical) regions where the nanowire devices are formed (see FIGS. 10A-10B for higher resolution images of devices). The position of the microfluidic channel used to deliver sample is highlighted by the dashed white rectangle and has a total size of 6 mm×500 microns, length×width. The image field is 8 mm×1.2 mm The schematic diagram (bottom) shows details of metal electrodes (gold) connecting nanowires (white lines) in this region with orientation rotated 90° relative to red rectangle. FIG. 10A is an optical image of one row of addressable device elements from the region highlighted by the dashed box in FIG. 9B. The white arrow highlights the position of a single device. The image field is to 350 microns×400 microns. FIG. 10B is a scanning electron microscopy image of one silicon nanowire device. The two parallel electrode contacts are visible at the upper and lower regions of the image; the nanowire, which is oriented approximately horizontally, is highlighted by the white arrow. The scale bar is 2 microns.

Figure 9B:
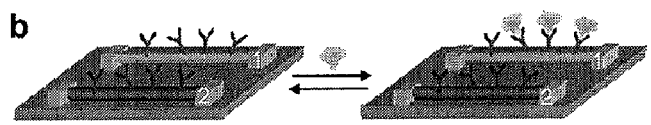

In addition, different receptors can be printed on the nanowire device array to allow selective multiplexed detection (FIG. 9B). This figure is a schematic showing two nanowire devices, 1 and 2, within an array, where the nanowires are modified with different antibody receptors, i.e., a first antibody receptor 5 on nanowire 1, and a second antibody receptor 6 on nanowire 2. A cancer marker protein 4 that binds specifically to its antibody receptor 5 (on nanowire 1) will produce a conductance change characteristic of the surface charge of the protein only on nanowire 1. However, cancer marker protein 4 does not bind to second antibody receptor 6.

Selective binding of cancer marker proteins to a surface-linked monoclonal antibodies would produce a conductance change in the corresponding receptor-modified silicon nanowire device, but not in devices without the specific antibody receptor. For a p-type doped silicon nanowire the conductance may increase (decrease) when a protein with negative (positive) surface charge bound to the antibody, while the opposite response may be observed for an n-type doped nanowire.

Figure 9C:
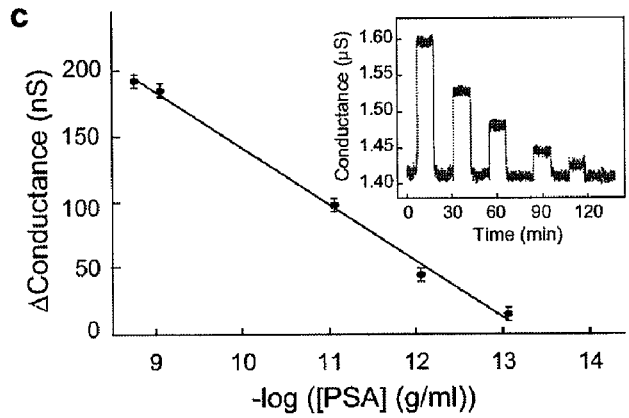

The sensitivity limits of these silicon nanowire devices for cancer marker protein detection were determined by measuring conductance changes as the solution concentration of prostate specific antigen (PSA) was varied, where the devices were modified with monoclonal antibodies for PSA (Ab1). Representative time-dependent data (inset, FIG. 9C) showed a well-defined conductance increase and subsequent return to baseline when PSA solution and pure buffer, respectively, were alternately delivered through a microfluidic channel to the devices. The data were recorded following alternate delivery of PSA and pure buffer solutions; the PSA concentrations were 5 ng/ml, 0.9 ng/ml, 9 pg/ml, 0.9 pg/ml and 90 fg/ml, respectively. The buffer solutions used in all measurements were 1 micromolar phosphate (potassium salt) containing 2 micromolar KCl, pH=7.4. A plot of these data (FIG. 9C) showed that the conductance change is directly proportional to the solution PSA concentration for values from about 5 ng/mL down to about 90 fg/mL. This figure shows a change in conductance vs. concentration of PSA for a p-type silicon nanowire modified with PSA-Ab1 receptor.

There were several important features observed. First, the reversibility of the conductance changes demonstrated that non-specific irreversible protein binding did not occur to a measurable extent on the devices. Second, the increases in conductance with PSA binding to the Ab1-linked p-type nanowire devices were consistent with binding of a protein with negative overall charge as expected from the pI of PSA, 6.8, and the pH, 7.4, of these experiments. Third, these data showed that direct label-free detection of PSA was routinely achieved with signal to noise >3 for concentrations down to about 75 fg/ml or about 2 fM. Similar ultrasensitive detection was achieved in studies of carcinoembryonic antigen (CEA), about 100 fg/ml or about 0.55 fM, and mucin-1, about 75 fg/ml or about 0.49 fM, (FIG. 11) using silicon nanowire devices modified with monoclonal antibodies for CEA and mucin-1, respectively. In these figures, FIG. 11A illustrates the change in conductance of a silicon nanowire device element modified with monoclonal antibody receptor for CEA vs. concentration of CEA, and FIG. 11B illustrates the change in conductance of a silicon nanowire device element modified with monoclonal antibody receptor for mucin-1 vs. concentration of mucin-1. The error bars correspond to ±1 standard deviation.

The surfaces of the nanowires were modified using the following procedure to covalently link antibody receptors and oligonucleotides to the surfaces of the silicon nanowire devices. First, the devices were reacted with a 1% ethanol solution of 3-(trimethoxysilyl)propyl aldehyde (United Chemical Technologies, Inc.) for about 30 min, washed with ethanol and heated at 120° C. for 15 min. Monoclonal antibody receptors, anti-PSA (AbI, NeoMarkers Inc. clone ER-PR8), anti-ACT-PSA (AbII, clone PSA1 with 59% cross-reactivity to ACT-PSA, abcam Inc.), anti-CEA antibody (clone COL-1, Neomarkers) and anti-mucin-1 (clone B413, abcam Inc.) were coupled to the aldehyde-terminated nanowire surfaces by reaction of 10-100 microgram/ml antibody in a pH=8.4, 10 mM phosphate buffer solution containing 4 mM sodium cyanoborohydride for a period of 2-3 hrs. Unreacted aldehyde surface groups were subsequently passivated by reaction with ethanolamine, in the presence of 4 mM cyanoborohydride, under similar conditions for a period of 1-2 hours. The device arrays for multiplexed experiments were made in generally the same way, except that distinct antibody solutions (1% v/v glycerol) were spotted on different regions of the array. The antibody surface density vs. reaction time was quantified by reacting Au-labeled IgG to antibodies (Ted Pella laboratories, 5 nm Au-nanoparticles) with aldehyde-terminated nanowires, and then imaging the modified nanowire by transmission electron microscopy.

PSA, PSA-ACT, CEA and mucin-1 were purchased from Calbiochem Inc. All protein samples were used as received without further purification and diluted in the assay buffer (1 micromolar phosphate buffer solution containing 2 micromolar KCl with pH 7.1) prior to the sensing measurements.

The electrical measurements were performed as follows. Electrical measurements were made using lock-in detection with a modulation frequency of 79 Hz, inclusive. The modulation amplitude was 30 mV and the dc source-drain potential was set at zero to avoid electrochemical reactions. Conductance vs. time data was recorded while buffer solutions, or different protein solutions, were flowed through the microfluidic channel. Protein sensing experiments were performed in the microfluidic channel under a flow rate of 0.15 ml/h in 1 micromolar phosphate buffer solution containing 2 micromolar KCl with pH 7.1. The multiplexing experiments were carried out by interfacing up to three independent lock-in amplifiers to different nanowire elements within the sensor arrays; the output was recorded simultaneous as a function of time by computer through analog-to-digital converter.

It was also noted that frequency dependent measurements showed that for a 12.6-times increase in detection frequency (from value used in these studies) the binding time increased by approximately 5 times. This behavior suggested that electrokinetic effects may contribute to and enhance the observed binding kinetics in some of these measurements.

Figure 9D:
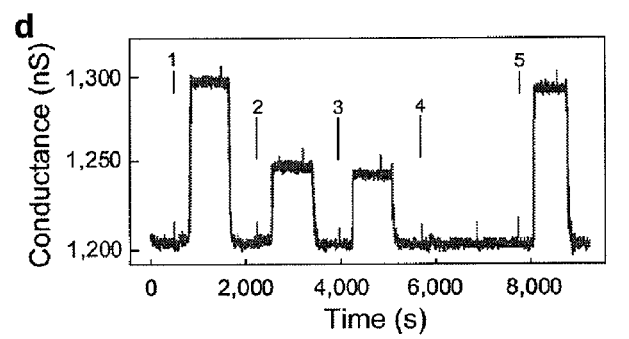

The reproducibility and selectivity of the nanowire devices was further investigated in competitive binding experiments with bovine serum albumin (BSA) as shown in FIG. 9D. Conductance versus time measurements recorded on a silicon nanowire device modified with Ab1 (i.e., a PSA-Ab1 modified p-type silicon nanowire) exhibited similar conductance changes as above when 9 pg/ml and 0.9 pg/ml solutions of PSA were delivered to the device. In FIG. 9D, the data were recorded following alternate delivery of the following protein and pure buffer solutions: (1) 9 pg/ml PSA, (2) 0.9 pg/ml PSA, (3) 0.9 pg/ml PSA and 10 microgram/ml BSA, (4) 10 microgram/ml BSA, and (5) 9 pg/ml PSA. These results showed that reproducible device to device sensitivity was achieved with these particular silicon nanowire sensors. Moreover, delivery of a solution containing 0.9 pg/ml PSA and 10 microgram/ml BSA showed the same conductance increase as a solution containing only PSA at this concentration, while no conductance change was observed in the device when the BSA solution alone was delivered. These latter data demonstrated selectivity using the antibody receptors and also that sensitivity was not lost even with a 10-million fold higher concentration of other proteins in solution.

Figure 9E:
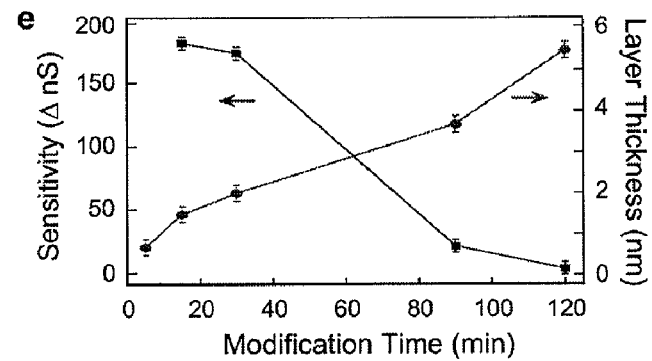

In addition, the details of the modification chemistry were investigated to define limits for high sensitivity detection of cancer marker proteins using these silicon nanowire field-effect devices. Specifically, atomic force microscopy measurements of the initial aldehyde-silane layer thickness on single nanowires (FIG. 9E) demonstrated a systematic increase with modification time. FIG. 9E shows the thickness dependence (curve 9) of aldehyde silane layer on the SiNW surfaces extracted from AFM measurements after different modification time of the aldehyde propyltrimethoxysilane, and the sensitivity dependence (curve 8) of the detection of 1 ng/ml of PSA, after different modification times, using a p-type SiNW device. Significantly, measurements of the nanowire device sensitivity showed that the sensor response decreases rapidly for initial reaction times >30 minutes.

In the AFM measurements, the increase in the thickness of silicon nanowires as a function of silane modification times was measured by atomic force microscopy (AFM, Digital Instruments Inc., Nanoscope IIIa) on a lithographically marked-Au surface, in order to localize and measure the same nanowires each time.

Example 2

Figure 12A:
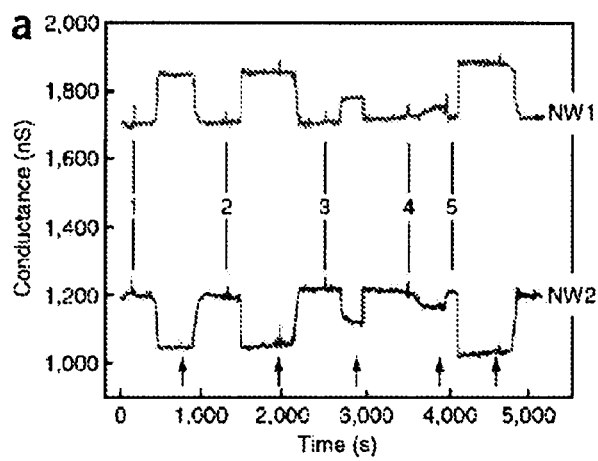
FIGS. 12A-12B illustrate multiplexed detection using various nanoscale wire sensors, according to other embodiments of the invention.

In this example, multiplexed detection with nanowire arrays is illustrated. Initially, the effectiveness of the nanowire device arrays for multiplexed detection was characterized using an array containing both p-type and n-type silicon nanowire devices that were modified with Ab1 as the marker protein receptor. The incorporation of p- and n-type nanowires in a single sensor chip allowed possible electrical cross-talk and/or false positive signals to be discriminated by correlating the response versus time from the two distinct types of device elements. Notably, simultaneous conductance versus time data recorded from p-type nanowire (NW1, FIG. 12A) and n-type nanowire (NW2, FIG. 12A) devices showed that introduction of 0.9 ng/ml of PSA resulted in a conductance increase in NW1 and a conductance decrease in NW2, while the conductance returned to the baseline value of each device following introduction of buffer solution without PSA. The magnitude of the conductance changes in the two devices were nearly the same and consistent with the concentration dependent conductance measurements show in FIG. 9. Similar behavior was observed from the two devices as the solution was alternated between different concentrations of PSA and pure buffer solution (FIG. 12A); that is, the p- and n-type devices showed concentration dependent increases and decreases, respectively, in conductance when the PSA solutions were added. In FIG. 12A, the complementary sensing of PSA using p-type (NW1) and n-type (NW2) silicon nanowire devices in the same array can be seen. The vertical solid lines correspond to times at which PSA solutions of (1) 0.9 ng/ml, (2) 0.9 ng/ml, (3) 9 pg/ml, (4) 0.9 pg/ml, and (5) 5 ng/ml were connected to the microfluidic channel Arrows correspond to the points where the solution flow was switched from protein to pure buffer solutions.

These experiments demonstrated several points about multiplexed electrical detection with nanowire devices. First, the complementary conductance changes observed for the p-type and n-type elements were consistent with specific binding of PSA to field-effect devices, since the negatively-charged protein caused accumulation and depletion in the p- and n-type nanowire elements, respectively. Second, the complementary electrical signals from p- and n-type devices provided simple yet robust means for detecting false positive signals from either electrical noise or nonspecific binding of protein to one device; that is, real and selective binding events must show complementary responses in the p- and n-type devices. The presence of correlated conductance signals in both devices (FIG. 12A), which occurred at points when buffer and PSA/buffer solutions were changed, illustrate how this multiplexing capability can be used to distinguish noise from protein binding signals.

Figure 12B:
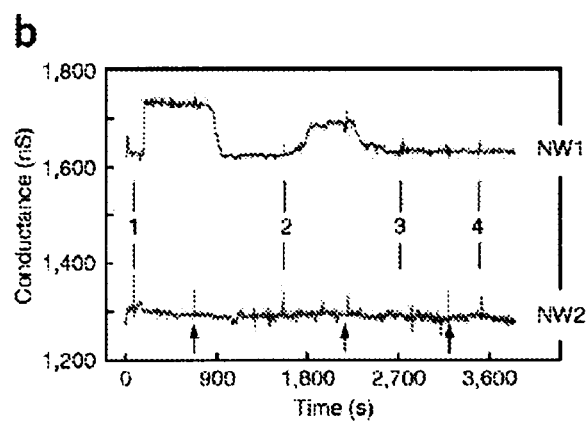

A second test of multiplexing capabilities was carried out using a device array consisting of p-type silicon nanowire elements with either PSA Ab1 receptors (NW1, FIG. 12B) or surfaces passivated with ethanolamine (NW2, FIG. 12B). Simultaneous measurements of the conductance of NW1 and NW2 showed that well-defined concentration-dependent conductance increases were only observed in NW1 upon delivery of PSA solutions (9 pg/ml and 1 pg/ml), although small conductance spikes were observed in both devices at the points where PSA and buffer solutions are changed. Delivery of BSA at 10 micrograms/ml showed no response in either NW1 or NW2, and subsequent delivery of a solution of PSA (1 ng/ml) and Ab1 (10 micrograms/ml), which complexes the free PSA, did not exhibit measurable conductance changes in either device. Together, these multiplexing experiments demonstrated that the electronic signals measured in the nanowire arrays can be readily attributed to selective marker protein binding, showing that the surface passivation chemistry effectively prevented non-specific protein binding, and also provided a robust means for discriminating against false positive signals arising from either electronic noise or nonspecific binding.

In FIG. 12B, the conductance vs. time data was recorded simultaneously from two p-type silicon nanowire devices in the array, where NW1 was functionalized with PSA Ab1, and NW2 was modified with ethanolamine. The vertical lines correspond to times when solutions of (1) 9 pg/ml PSA, (2) 1 pg/ml PSA, (3) 10 microgram/ml BSA, (4) a mixture of 1 ng/ml PSA and 10 μg/ml PSA Ab1 were connected to the microfluidic channel. The arrows correspond to the points where the solution flow was switched from protein to pure buffer solutions.

Example 3

This example illustrates the multiplexed detection of cancer markers. To test the capabilities of the nanowire arrays for multiplexed detection of marker proteins relevant to cancer diagnosis, the initial experiments focused on prostate cancer where concentrations of both free PSA (f-PSA) and PSA-alpha-1-antichymotrypsin (PSA-ACT) complex are generally measured. In these experiments, a device array was fabricated from p-type silicon nanowire elements that were then modified either with monoclonal antibody receptors for f-PSA, Ab1, or monoclonal antibody receptors that show cross-binding reactivity for f-PSA and the PSA-ACT complex, Ab2. Simultaneous conductance measurements of NW1, which was modified with Ab1, and NW2, which was modified with Ab2, were carried out for a wide-range of conditions (FIG. 13) and are summarized in Table 1.

Figure 13:
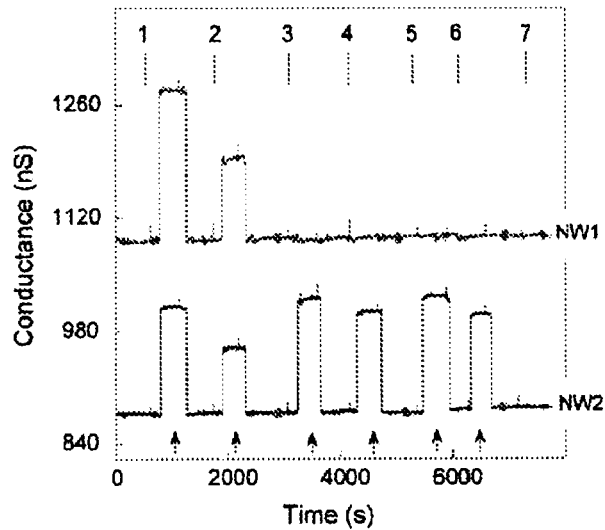
FIG. 13 illustrates the multiplexed detection of certain marker proteins, according to one embodiment of the invention.

FIG. 13 shows representative conductance vs. time data recorded simultaneously from two p-type silicon nanowire devices in an array, where NW1 was modified with Ab1, which is selective to f-PSA, and NW2 was modified with Ab2, which is cross reactive to f-PSA and PSA-ACT. The protein solutions were added at the numbered points as follows: (1) 850 pg/ml f-PSA; (2) 8.5 pg/ml f-PSA; (3) 3200 pg/ml PSA-ACT; (4) 320 pg/ml PSA-ACT; (5) 850 pg/ml f-PSA, 3200 pg/ml PSA-ACT, and $1\times10^7$ pg/ml Ab1; (6) 8.5 pg/ml f-PSA, 320 pg/ml PSA-ACT, and $1\times10^7$ pg/ml Ab1; (7) 850 pg/ml f-PSA and $1\times10^7$ pg/ml Ab1. Arrows correspond to the points where the fluid delivery was switched from protein to pure buffer solutions.

TABLE 1

| Protein Sample | [Protein] pg/ml | Conductance Change, nS | |
|---|---|---|---|
| | | NW1-Ab1 | NW2-Ab2 |
| f-PSA | 1700 | 192 | 154 |
| f-PSA | 850 | 185 | 132 |
| f-PSA | 8.5 | 98 | 81 |
| f-PSA | 0.85 | 45 | 50 |
| f-PSA | 0.085 | 15 | 10 |
| PSA-ACT | 3200 | ND | 143 |
| PSA-ACT | 320 | ND | 124 |
| PSA-ACT | 3.2 | ND | 67 |
| PSA-ACT | 0.32 | ND | 19 |
| f-PSA, PSA-ACT, Ab1 | 850, 3200, $1 \times 10^7$ | ND | 140 |
| f-PSA, PSA-ACT, Ab1 | 8.5, 320, $1 \times 10^7$ | ND | 118 |
| f-PSA, PSA-ACT, Ab1 | 0.85, 3200, $1 \times 10^7$ | ND | 138 |
| f-PSA, PSA-ACT, Ab1 | 850, 0.32, $1 \times 10^7$ | ND | 15 |
| f-PSA, Ab1 | 850, $1 \times 10^7$ | ND | ND |

ND corresponds to no detected conductance change. Sensor data used to obtain conductance changes are shown in FIG. 13.

The data show that delivery of f-PSA resulted in concentration-dependent conductance changes in both NW1 and NW2, while the introduction of PSA-ACT yielded concentration-dependent conductance changes only in NW2. In addition, control experiments in which solutions of f-PSA, PSA-ACT, and Ab1 were delivered to the device array showed concentration conductance changes in NW2 but not NW1, since f-PSA was blocked by Ab1 present in the solution. These multiplexing results thus demonstrate selective, high-sensitivity detection of both markers, and showed that nanowire sensor arrays could be used to measure the f-PSA and PSA-ACT concentrations in a single real-time assay.

Figure 14:
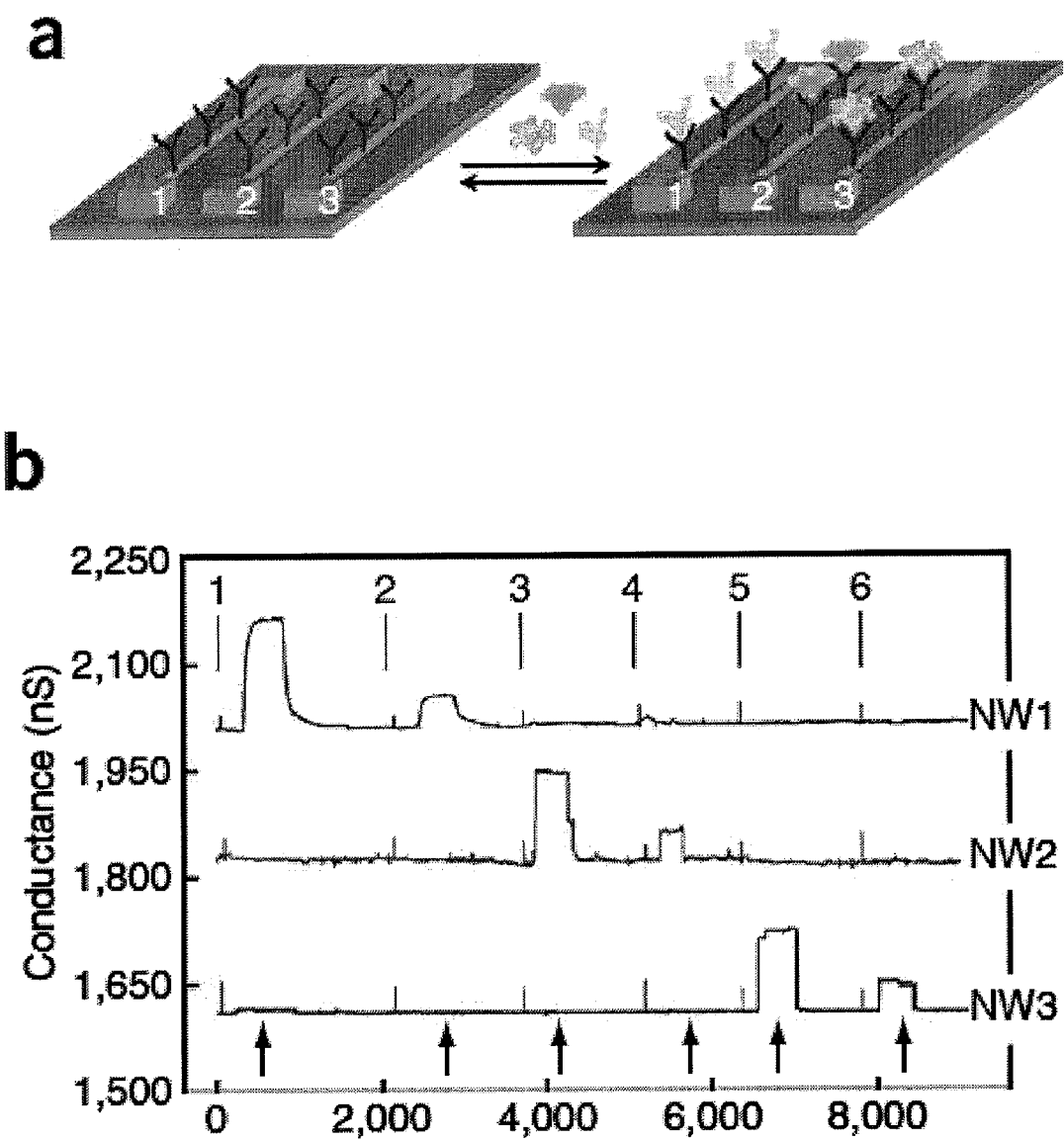
FIGS. 14A-14B illustrate the detection of certain cancer marker proteins, according to still another embodiment of the invention.

Multiplexed detection of distinct marker proteins, which may facilitate pattern analysis of existing and emerging markers for robust cancer diagnosis, can also be carried out with high sensitivity and selectivity using nanowire arrays modified with distinct antibody receptors as shown in FIG. 14A, where three silicon nanowire devices in an array are used for multiplexed protein detection. The devices were fabricated from the similar nanowires, and then differentiated with distinct monoclonal antibody receptors specific to three different cancer markers, f-PSA (NW1), CEA (NW2), and mucin-1 (NW3). Conductance vs. time measurements were recorded simultaneously from NW1, NW2 and NW3 as different protein solutions were sequentially delivered to to the device array as shown in FIG. 14B. The solutions were delivered to the nanowire array sequentially as follows: (1) 0.9 ng/ml PSA, (2) 1.4 pg/ml PSA, (3) 0.2 ng/ml CEA, (4) 2 pg/ml CEA, (5) 0.5 ng/ml mucin-1, (6) 5 pg/ml mucin-1. Buffer solutions were injected following each protein solution at points indicated by black arrows.

The introduction of f-PSA and buffer solutions led to concentration-dependent conductance increases only when NW1 was exposed to PSA solution; no conductance changes were observed in NW2 or NW3. Similarly, introduction of CEA solutions to the device array yielded concentration dependent conductance changes only in NW2, while subsequent delivery of mucin-1 solutions to the array resulted in concentration dependent conductance changes only in NW3. These results demonstrate capability for multiplexed real-time, label-free marker protein detection with sensitivity at the femtomolar level and a high degree of selectivity.

Example 4

The multiplexed examples described above demonstrate a unique level of sensitivity and selectivity. To impact cancer diagnosis and treatment in the most significant way will require rapid analysis of clinically relevant samples, such as blood serum. This example demonstrates the detection of PSA in undiluted donkey and human serum samples that were desalted by a rapid and simple purification step. The measurements were made using p-type silicon nanowire elements with either PSA Ab1 receptors (NW1, FIGS. 14C-14E) or surfaces passivated with ethanolamine (NW2, FIGS. 14C-14E) in the same sensor array.

Donkey serum (pooled preparation obtained from normal donor herd, total protein 59 mg/ml), and human serum (from clotted human male whole blood, 40-90 mg/ml total protein) were purchased from Sigma, desalted using a microcentrifuge filter (Centricon YM-3, 3,000 MWCO, Millipore Corp.) and diluted back to the original protein concentration with the assay buffer solution (1 micromolar phosphate buffer+2 micromolar KCl, pH 7.1) prior to injection into the detection system. PSA was added to donkey serum prior to the desalting step for data presented in the paper; however, similar results were also obtained from samples in which PSA was added after desalting.

Conductance vs. time measurements recorded simultaneously from NW1 and NW2 as different donkey serum solutions were sequentially delivered to the devices are shown in FIGS. 14C and 14D. FIG. 14C shows conductance vs. time data recorded for the to detection of PSA-containing donkey serum samples on a p-type silicon nanowire array in which NW1 was functionalized with Ab1 and NW2 was passivated with ethanolamine. The solutions were delivered to the nanowire array sequentially as follows: (1) 1 micromolar phosphate buffer+2 micromolar KCl, pH=7.1, (2) donkey serum, (3) a mixture of donkey serum and 90 pg/ml of PSA, (4) a mixture of donkey serum and 0.9 ng/ml of PSA. The donkey serum was injected at points indicated by the black arrows. FIG. 14D shows conductance vs. time data recorded for the same two p-type silicon nanowire devices as FIG. 14C following addition of (1) donkey serum, (2) a mixture of donkey serum and 0.9 pg/ml of PSA.

The introduction of donkey serum containing 59 mg/ml total protein did not lead to appreciable conductance change relative to the standard assay buffer. Also, introduction of donkey serum solutions containing f-PSA led to concentration-dependent conductance increases only for NW1; no conductance changes were observed in NW2 (FIGS. 14C and 14D). Well-defined conductance changes were observed for PSA concentrations as low as 0.9 pg/ml, which corresponded to ~100 billion times lower concentration than that of the background serum proteins.

Similar results were also obtained in conductance vs. time data recorded simultaneously from NW1 and NW2 for different human serum samples (FIG. 14E). FIG. 14E shows conductance vs. time data recorded for the detection of PSA-containing human serum samples on a p-type silicon nanowire array in which NW1 was functionalized with Ab1 and NW2 was passivated with ethanolamine. The solutions were delivered to the nanowire array sequentially as follows: (1) 1 micromolar phosphate buffer+2 micromolar KCl, pH=7.1, (2) a mixture of human serum preblocked with 10 micrograms/ml Ab1, (3) human serum, and (4) same as (2). Specifically, addition of undiluted human serum, which contained f-PSA, blocked with an excess of Ab1 showed little change in baseline for either NW1 or NW2, although subsequent addition of undiluted human serum showed well-defined conductance increase in NW1. These results thus demonstrate the ability to detect cancer markers with high sensitivity and selectivity in human serum.

Example 5

This example illustrates telomerase detection and activity. To define further the potential of the silicon nanowire arrays described herein as broad-based cancer to diagnostic tools, in this example, an orthogonal nucleic acid based marker assay involving detection of telomerase was investigated. Telomerase is a eukaryotic ribonucleoprotein (RNP) complex that catalyzes the addition of the telomeric repeat sequence TTAGGG (SEQ ID NO: 1) to the ends of chromosomes using its intrinsic RNA as a template for reverse transcription. Telomerase is inactive in most normal somatic cells but has been found to be active in at least 80% of known human cancers, and thus been proposed as both a marker and therapeutic target for cancer detection and treatment, respectively.

The underlying concept of the telomerase assay is illustrated in the schematic shown in FIG. 1. First, silicon nanowire device elements within an array are functionalized with oligonucleotide primers complementary to the telomerase binding site (FIG. 1A). Second, a solution containing telomerase 235 is delivered to the device, and the presence/absence of telomerase is then detected by monitoring the nanowire conductance following delivery of a sample cell extract to the device array (FIG. 1B). In some cases, telomerase binds in a concentration dependent manner. In the case of p-type nanowire device elements, binding may produce a reduced conductance since telomerase (pI~10) is positively charged at physiological pH. Third, the addition of deoxynucleotide triphosphates (dNTPs) 236 leads, in the presence of active telomerase, to telomerase catalyzed primer extension/elongation that may produce an increase in conductance due to the incorporation of negatively-charged nucleotides near the nanowire surface (FIG. 1C).

Figure 15:
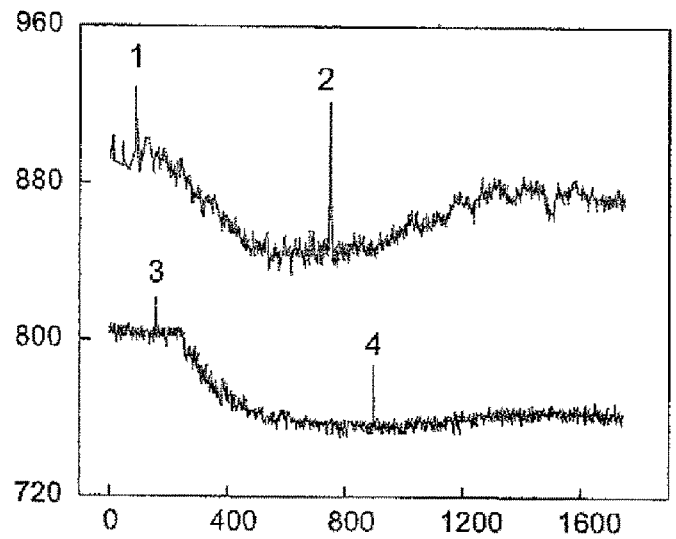
FIGS. 15A-15C illustrate data showing the binding of telomerase, in another embodiment of the invention.
Figure 15:
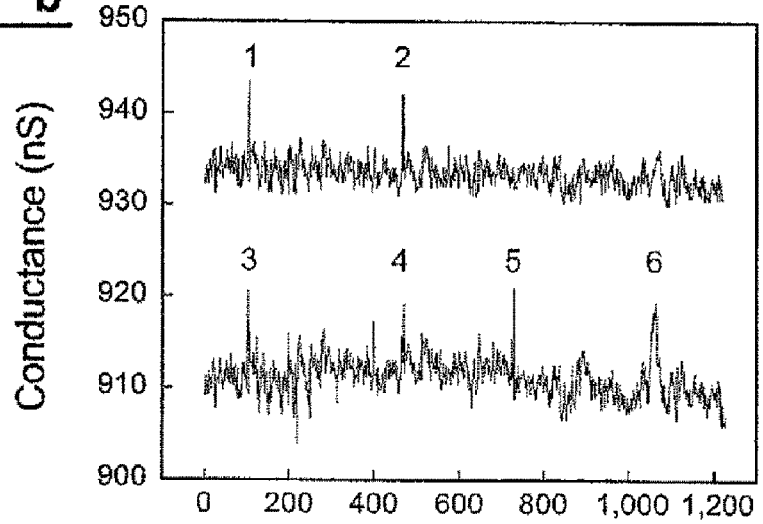
Figure 15:
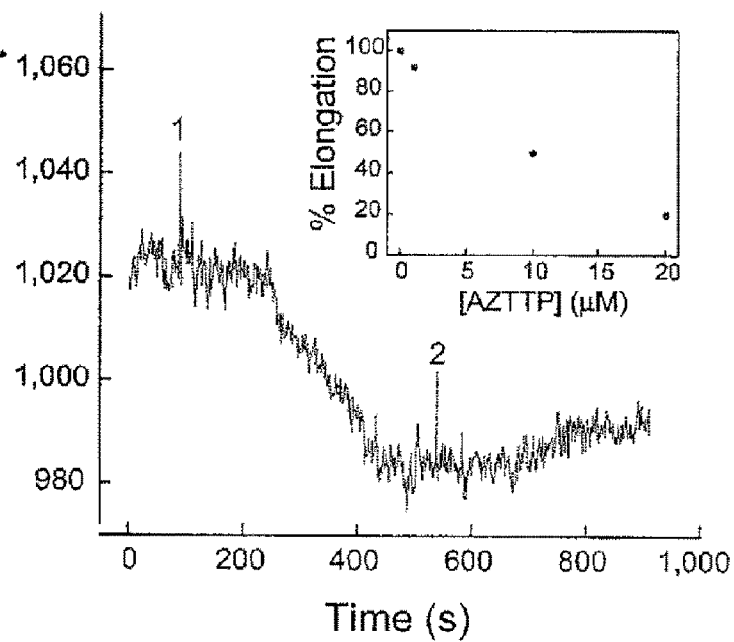

Representative conductance versus time data recorded from an oligonucleotide primer modified p-type silicon nanowire element (FIG. 15A) shows a well-defined conductance decrease following delivery of the extract from 100 HeLa cells to the device array. This conductance decrease may be attributed to selective binding of positively charged telomerase at the surface of p-type nanowires in the array. The conductance decrease was directly proportional to number of HeLa cells (and hence telomerase concentration) used to prepare the extract (FIG. 16) as expected for an equilibrium binding process. In FIG. 15A, the conductance vs. time data was recorded following the introduction of (1) a solution containing extract from 100 HeLa cells and 0.4 mM dCTP, (2) a mixture all four dNTPs (dATP, dGTP, dUTP and dCTP) each at 0.1 mM, (3) a solution containing extract from 100 HeLa cells and 0.4 mM dCTP, and (4) 0.4 mM dCTP only. Points (3) and (4) were recorded using a second device.

Figures 16A, 16B:
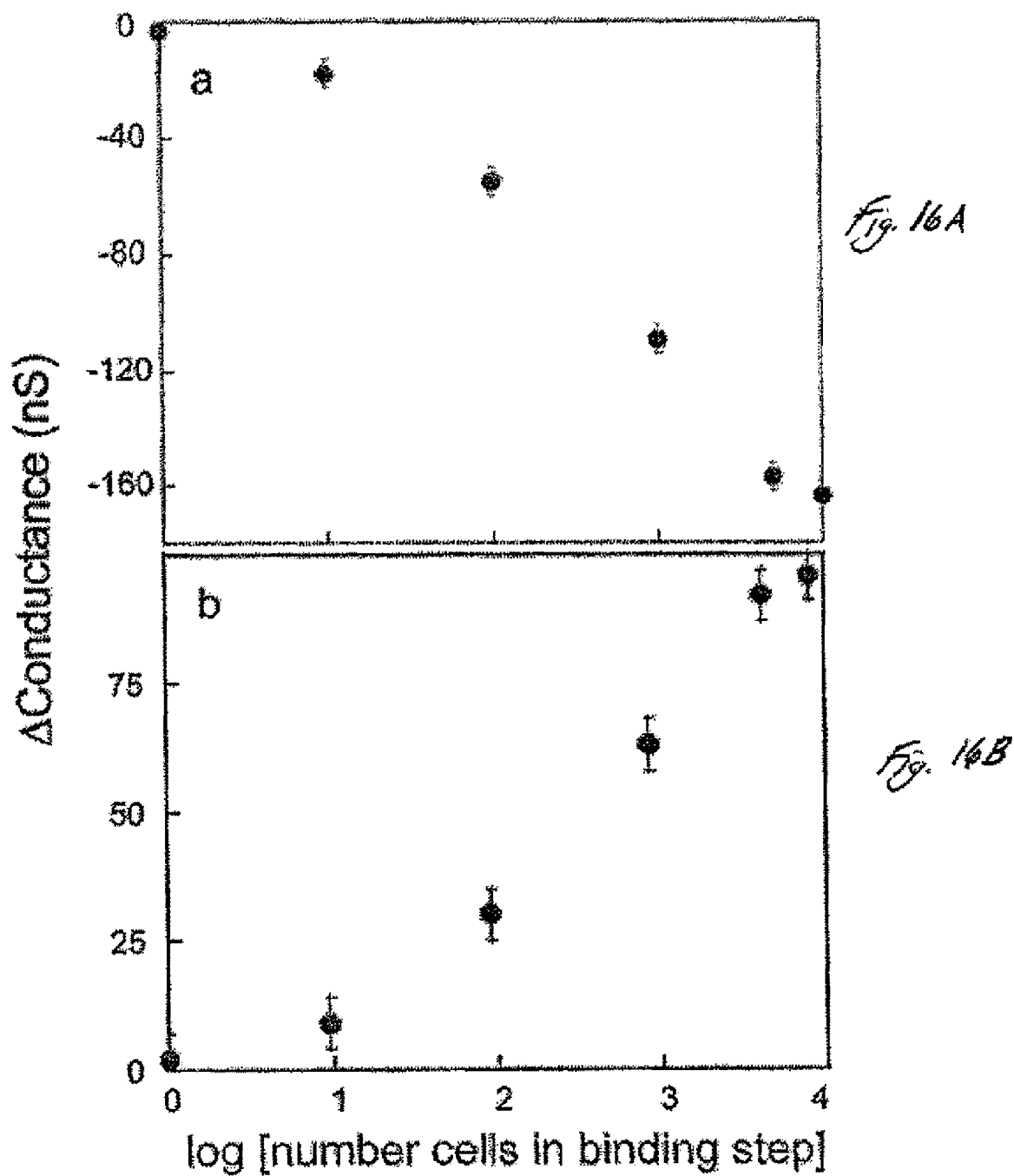
FIGS. 16A-16B illustrate telomerase binding in yet another embodiment of the invention.

These data also showed that binding was readily detectable at the 10 cell level without amplification. In FIG. 16A, the steady-state conductance change was associated with telomerase binding to oligonucleotide primer-modified p-type silicon nanowires as a function of the number of HeLa cells used to prepare extract solution. Each solution contained dCTP at 0.4 mM. FIG. 16B shows the steady state conductance when a mixture of all four dNTPs each at 0.1 mM was delivered to the nanowire devices following initial telomerase binding step using extract from different numbers of HeLa cells.

Additionally, delivery of a solution extract prepared from 100,000 normal human fibroblasts cells to nanowire device (FIG. 15B, point 1) showed no conductance change. Moreover, delivery of HeLa cell extracts that were pre-incubated with a solution of oligonucleotide, which blocks binding to the much lower concentration of surface-bound primers, did not result in an observable conductance change (FIG. 15B, point 3). Also, experiments carried out using heat denatured HeLa cell extracts exhibited essentially no conductance decrease above background (FIG. 15B, point 5). In FIG. 15B, the data are presented as conductance vs. time data, recorded following delivery of (1) a solution containing extract from 100,000 normal human fibroblast cells and 0.4 mM dCTP, (2) a mixture of all four dNTPs each at 0.1 mM, (3) a solution containing extract from 10,000 HeLa cells, 0.4 mM dCTP, and 5 micromolar oligonucleotide (amino-modified oligonucleotide 5'-$H_2N$—$(CH_2)_6$-TTTTTTAATCCGTCGAG-CAGAGTT-3' (SEQ ID NO. 60)), (4) a mixture of all four dNTPs each at 0.1 mM, (5) a solution containing extract from 10,000 heat-deactivated HeLa cells (90° C., 10 min) and 0.4 mM dCTP, and (6) a mixture of all four dNTPs each at 0.1 mM.

All cell extracts from frozen cell pellets were prepared using CHAPS lysis buffer (Centricon International Inc., 100 microliter 1×CHAPS buffer, 10 mM Tris-HCl pH 7.5, 1 mM $MgCl_2$, 1 mM EGTA, 0.1 mM benzamidine, 0.5% CHAPS (3-[(3-cholamidopropyl)dimethylammonio]propanesulfonic acid), 5 micromolar alpha-mercaptoethanol and 10% Glycerol) fractionated and stored at −80° C. until used and diluted in telomerase assay buffer (10 micromolar Hepes buffer, 1.5 mM KCl, 100 micromolar $MgCl_2$ and 10 micromolar EGTA, pH 7.4). Normal human fibroblast cells to (ATCC), HeLa cells (Chemicon International), AZTTP (azido deoxythymidine triphosphate, Sigma-Aldrich), and dATP, dGTP, dUTP and dCTP (Sigma) were used as received. Aldehyde functionalized SiNWs were modified with the amino-modified oligonucleotide 5'-$H_2N$—$(CH_2)_6$-TTTTTTAATCCGTCGAG-CAGAGTT-3' (SEQ ID NO: 60) (Sigma-Genosys Inc.) in 100 mM phosphate buffer pH 8.4 and 5 mM $NaCNBH_3$ for 2 h. The sensor array was washed using the microfluidic channel with 100 mM phosphate buffer pH 8.4, and then the telomerase assay buffer (10 micromolar Hepes buffer, 1.5 mM KCl, 100 micromolar $MgCl_2$ and 10 micromolar EGTA, pH 7.4).

The primer-modified nanowire arrays were used to monitor directly telomerase activity. FIG. 15A showed that adding a solution of dNTPs following initial telomerase binding lead to an increase in the device conductance. This increase is consistent with the incorporation of negatively charged nucleotide units on the nanowire surface during the elongation catalyzed by telomerase. In the absence of a mixture of dNTPs, no significant conductance increase was observed after the telomerase binding step (FIG. 15A), which may show that the observed increases did not correspond to unbinding of telomerase on the time scale of the experiment. In addition, the conductance increase at fixed concentration of dNTPs was proportional to number of HeLa cells used for initial binding step (FIG. 16), which showed that the overall nucleotide addition depended on the telomerase concentration bound initially to primers. These data also demonstrated that telomerase activity could be monitored at least to the 10 cell level without amplification. Further experiments showed that the delivery of dNTP solutions following an initial addition of (1) extract from normal human fibroblasts cells (FIG. 15B, point 2), (2) HeLa cell extracts pre-incubated with a primer-oligonucleotides (FIG. 15B, point 4), or (3) heat denatured HeLa cell extracts (FIG. 15B, point 6) to the nanowire devices did not result in conductance increases. These control experiments showed that conductance increases observed in the presence of dNTPs is indeed due to telomerase catalyzed nucleotide addition. Significantly, the telomerase activity measurements were distinct from current approaches based upon variations of telomeric repeat amplification protocol (TRAP), since PCR amplification was not required to achieve high sensitivity.

Lastly, the nanowire detectors, which allow direct monitoring of telomerase binding and/or activity, could be used to screen for inhibitors that might serve as therapeutic agents. This was shown by investigating the inhibition of telomerase elongation activity in the presence of azido deoxythymidine triphosphate (AZTTP), which is a known reverse transcriptase inhibitor. Significantly, FIG. 15C shows that the conductance increase associated with elongation was reduced when a solution of dNTPs and AZTTP is delivered to a nanowire device following initial telomerase binding. Studies of AZTTP concentration-dependent inhibition (inset, FIG. 15C) showed up to a 80% reduction of elongation as the AZTTP concentration is increased to 20 micromolar, and thus demonstrated the capability to evaluate directly inhibition of telomerase activity. In FIG. 15C, conductance vs. time data are shown as recorded on a p-type silicon nanowire device following the introduction of (1) a solution containing extract from 100 HeLa cells and 0.4 mM dCTP, and (2) a mixture of all four dNTPs each at 0.1 mM and 20 micromolar AZTTP. The inset is a plot of the inhibition of elongation vs. AZTTP concentration, where 100% corresponds to conductance change associated with elongation in absence of AZTTP.

Thus, these examples demonstrate the development and validation of nanowire sensor arrays for label-free, real-time, multiplexed electrical detection of cancer markers with ultra-high sensitivity and excellent selectivity. The nanowire arrays have been used to elucidate the surface modification details needed for ultrahigh device sensitivity, to demonstrate very good device to device absolute detection reproducibility, and also to show two distinct approaches for simultaneous discrimination against false positives. Using the nanowire sensor arrays modified with antibody receptors these examples demonstrate real-time multiplexed detection of f-PSA, PSA-ACT complex, CEA and mucin-1 with good signal-to-noise ratios down to a 50-100 fg/ml level, and showed that high selectivity with sensitivity to concentrations at least as low as 0.9 pg/ml could be achieved in undiluted serum samples containing as much as 100 billion times more protein than the cancer marker being detected. In addition, using the same chemistry to prepare nucleic acid primer modified devices it was shown that telomerase binding and activity could be measured down to a 10 cell level without amplification.

These examples also demonstrate a sensitive telomerase binding and activity assay, which exploits the same basic sensor array and modification chemistry used for protein marker detection, thus showing the power of the nanowire sensor arrays for cancer detection. The direct nanowire-based assay achieves at least a level of sensitivity in about 10 cells but can do so without the need for PCR cycling and labeling, unlike to TRAP-based protocols, where PCR-cycling is used for amplification and fluorescence or radiolabeling is used in detection. The direct measurement of telomerase binding and activity also makes possible straightforward studies of inhibition of both steps using added small molecules.

In conclusion, these examples demonstrate highly sensitive and selective multiplexed electrical detection of protein cancer markers and telomerase using arrays of silicon nanowire field-effect devices in both idealized solutions and clinically relevant blood serum and cell extract samples. The present example limited simultaneous real-time measurements to three distinct sensor devices, although it should be noted that this limit was only related to available measurement electronics, and could easily be improved with additional measurement electronics. At least 100 independently addressable sensor elements are available in the arrays described in this example and could be utilized with more sophisticated multiplexing electronics. Considering the capabilities demonstrated in this work and the potential to expand significantly this real-time multiplexing, it is believed that the nanowire sensor arrays will move beyond current technologies and take advantage of information emerging from genomics and proteomics to improve diagnosis and treatment of cancer and other complex diseases.

Example 6

This example describes direct, real-time electrical detection of single virus particles with high selectivity by using nanowire field effect transistors. Measurements made with nanowire arrays modified with antibodies for influenza A showed discrete conductance changes characteristic of binding and unbinding in the presence of influenza A but not paramyxovirus or adenovirus. Simultaneous electrical and optical measurements using fluorescently labeled influenza A were used to demonstrate conclusively that the conductance changes correspond to binding/unbinding of single viruses at the surface of nanowire devices. Also, pH-dependent studies further show that the detection mechanism is caused by a field effect, and that the nanowire devices can be used to determine rapidly isoelectric points and variations in receptor-virus binding kinetics for different conditions. Lastly, studies of nanowire devices modified with antibodies specific for either influenza or adenovirus show that multiple viruses can be selectively detected in parallel. The possibility of large-scale integration of these nanowire devices suggests potential for simultaneous detection of a large number of to distinct viral threats at the single virus level.

The underlying concept of these experiments is illustrated schematically in FIG. 17. When a virus particle binds to the antibody receptor on a nanowire device, the conductance of that device may change from a baseline value, and when the virus unbinds, the conductance should return to the baseline value. For a p-type nanowire, the conductance should decrease (increase) when the surface charge of the virus is positive (negative). The conductance of a second nanowire device at which binding does not occur during this same time period should show no change and can serve as an internal control. Modification of different nanowires within the array with receptors specific for different viruses provides a means for simultaneous detection of multiple viruses.

More specifically, FIG. 17A is a schematic showing two nanoscale wire devices, numbered 1 and 2, where the nanoscale wires are modified with different antibody receptors. In FIG. 17B, the specific binding of a single virus to the receptors on nanowire 2 produces a conductance change characteristic of the surface charge of the virus only in nanoscale wire 2. When the virus unbinds from the surface, the conductance returns to the baseline value.

This example uses arrays of individually addressable silicon nanowire field-effect transistors, which exhibit reproducible high-performance properties, for these experiments. Representative microscopy images of a silicon nanowire device array are shown in FIG. 5. The nanowire elements were confined to a central region that was coupled to a microfluidic channel for sample delivery; the larger-scale metal electrodes, which are used for electrical connections to measurement instrumentation, were passivated with silicon nitride in all areas exposed to solution. Nanowire elements within the arrays were functionalized with the same or different virus-specific antibodies as receptors for selective binding.

Figure 5A:
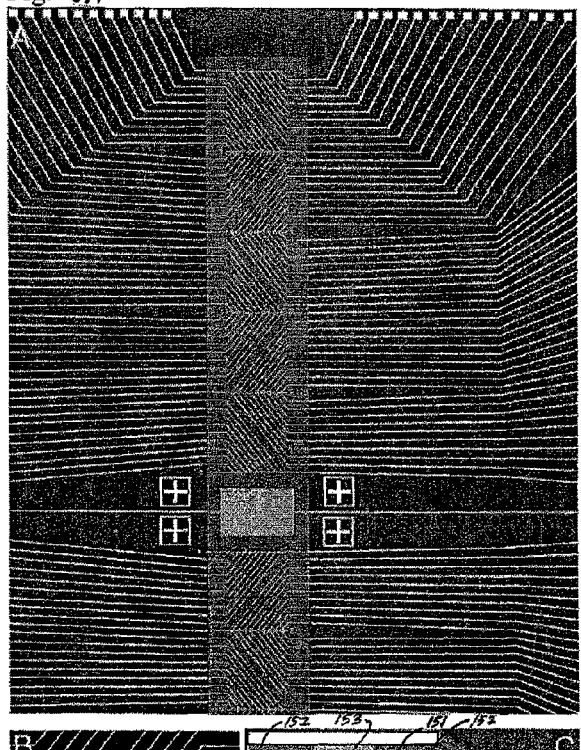
FIGS. 5A-5F illustrate various devices of the invention.
Figures 5B, 5C:
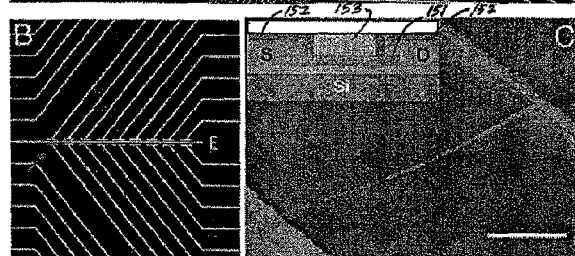
Figures 5D, 5E:
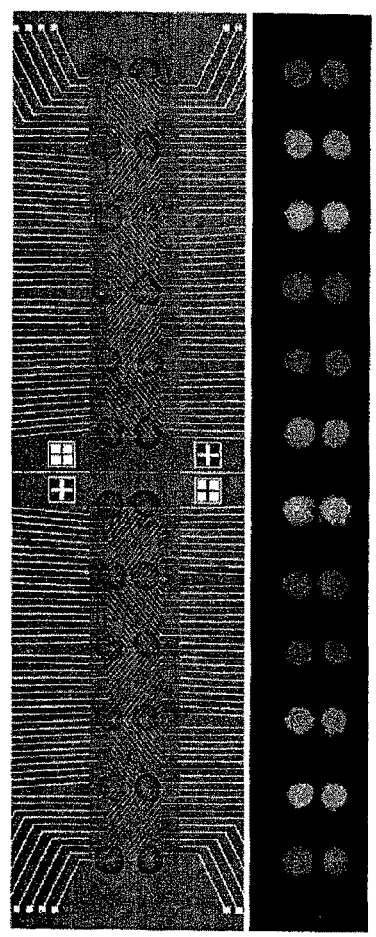
Figure 5F:
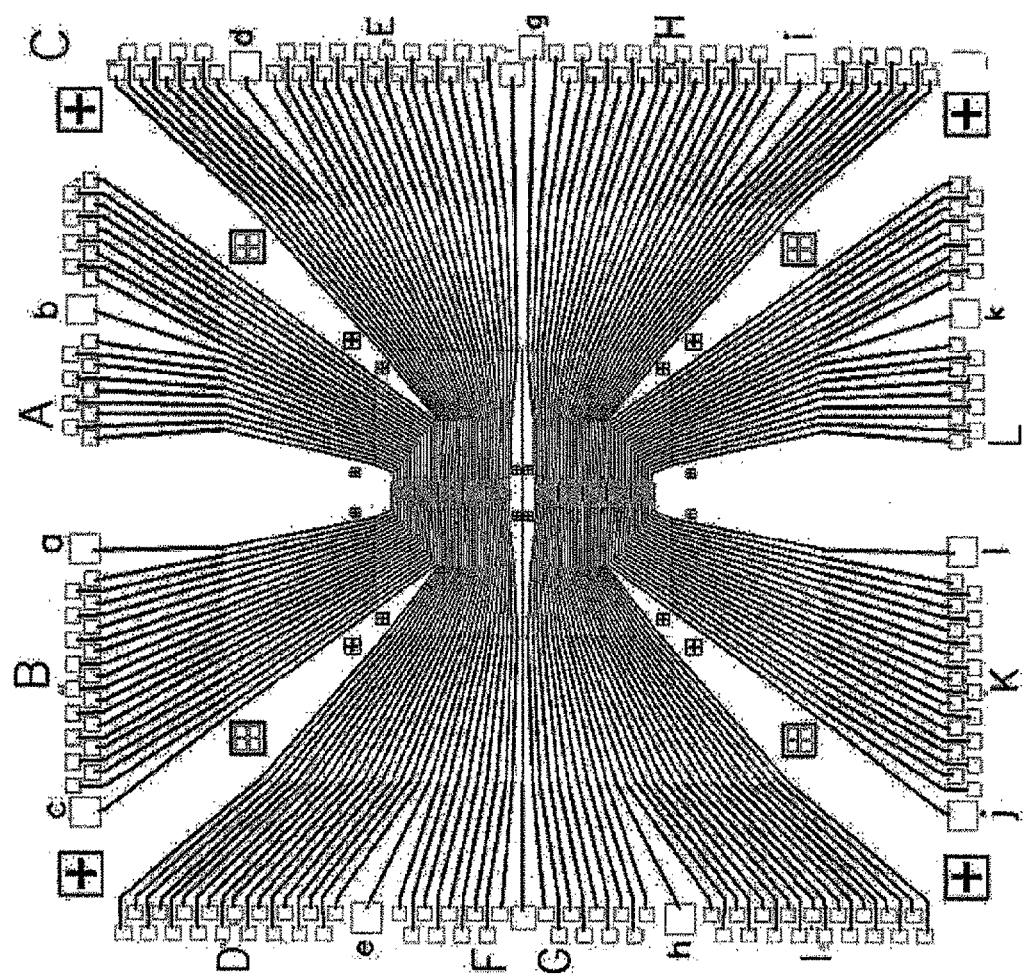

In this figure, FIG. 5A is an optical image of the upper portion of a device array (the entire device is shown in FIG. 5F). White lines correspond to metal electrodes that connect to individual nanowire devices. The position of the microfluidic channel used to deliver sample is highlighted (center portion) and has a total size of 6 mm×500 micrometers, length×width. The image field is 4.4×3.5 mm FIG. 5B is an optical image of one row of addressable device elements from the region highlighted by the dashed box in FIG. 5A. The arrow highlights the position of a device. The image field is to 500×400 micrometers. FIG. 5C is a scanning electron microscopy image of one sensing element. The electrode contacts are visible at the upper right and lower left regions of the image. The scale bar is 500 nm. The inset is a cross-sectional schematic of a single silicon nanowire device. The nanowire 151 is connected at its ends by source (S) and drain (D) metal electrodes, and the metal is insulated with a layer of silicon nitride 152. The microfluidic channel is 153. FIGS. 5D-5E illustrates the device after a series of fluidic droplets have been placed on each of the sensing elements, optically (FIG. 5D) and fluorescently (FIG. 5E).

Figure 18A:
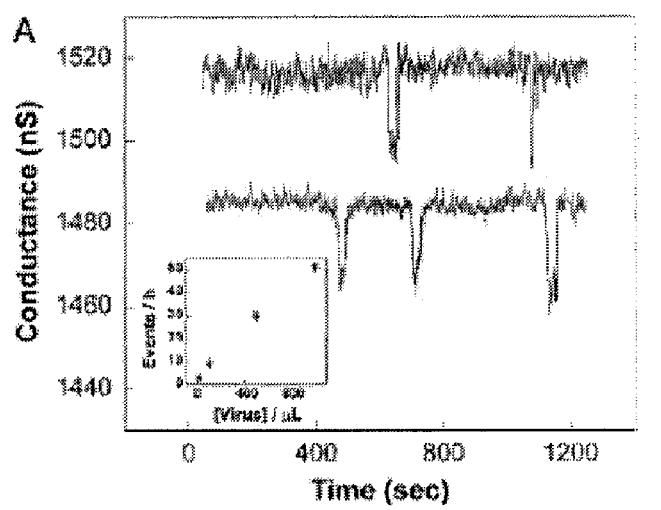
FIGS. 18A-18D illustrate the detection of certain viruses, according to another embodiment of the invention.

Time-dependent conductance data recorded simultaneously from two nanowires in the same device array modified with antibodies specific for influenza A virus (FIG. 18A) showed discrete changes in conductance when a solution containing about 100 virus particles per microliter was delivered to the sensor elements. There are several noteworthy features of these experiments. First, the magnitude and duration of the conductance drops are nearly the same for a given nanowire: for nanowires 1 and 2 the magnitude and duration were 24±1 nS and 20±4 s, and 20±3 nS and 15±7 s, respectively. The similarity in responses was consistent with good reproducibility in the nanowires electronic properties and a uniform density of antibody receptors on their surfaces, which determine the response to and duration of binding of a single virus, respectively. Second, an excess of free antibody added to the viral solution (monoclonal antihemagglutinin for influenza A was added to a standard solution containing 100 virons per microliter to yield an antibody concentration of 10 µg/ml) eliminated the well defined conductance changes, consistent with blocking sites on the viruses that are recognized by the same antibodies attached to the nanowire surfaces. Lower antibody concentrations produced partial reduction of the nanowire response. Third, the discrete conductance changes were uncorrelated for the two nanowire devices in the microfluidic channel and were thus consistent with stochastic binding events at or near the surfaces of the respective nanowires. Fourth, concentration-dependent measurements showed that the frequency of the discrete conductance drops was directly proportional to the number of virus particles in solution (FIG. 18A inset and FIG. 19). The observed frequencies also agreed with estimates for a diffusion limited process. Lastly, little or no purification of virus samples was required in these measurements; that is, similar results were obtained on samples purified by simple gel filtration or diluted directly from allantoic fluid.

Figure 18B:
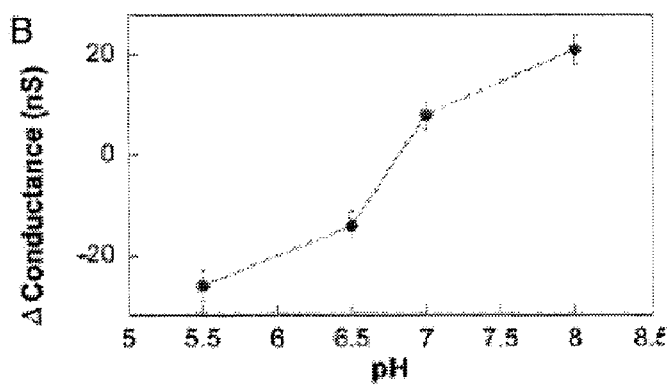
Figure 18C:
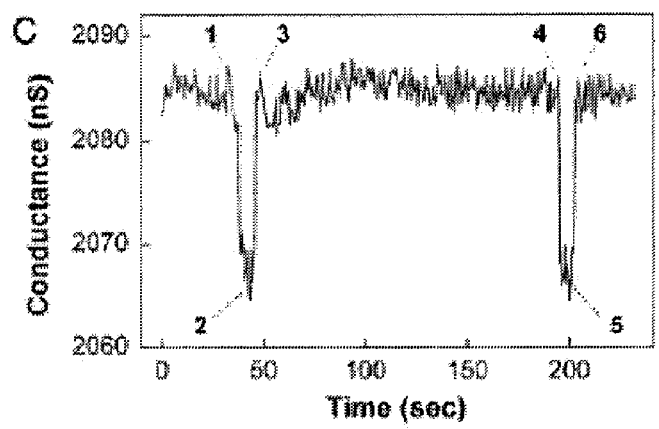
Figure 18D:
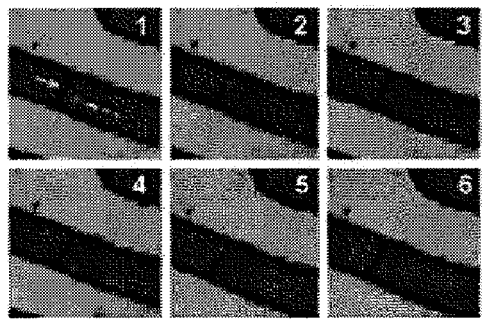

FIG. 18A is a plot of conductance vs. time data recorded simultaneously from two silicon nanowires elements, within a single device array after introduction of an influenza A solution. The inset is a plot of the frequency of single virus events as a function of virus solution concentration. FIG. 18B shows conductance changes associated with single influenza A virus binding/unbinding as a function of solution pH. FIG. 18C shows conductance and FIG. 18D shows optical data, each recorded simultaneously vs. time for a single silicon nanowire device after introduction of influenza A solution. Combined bright-field and fluorescence images correspond to time points 1-6 indicated in the conductance data; virus appears as a dot in the images. The solid white arrow in image 1 of FIG. 18D highlights the position of the nanowire device, and the dashed arrow indicates the position of a single virus. Images are 8×8 micrometers. All measurements were performed with solutions containing 100 viral particles per microliters. FIG. 19 shows additional conductance vs. time data, recorded as a function of influenza A concentration. FIG. 19A is virus-free buffer solution, FIG. 19B is 30 viral particles per microliter, FIG. 19C is 100 viral particles per microliter, and FIG. 19D is 1,000 viral particles per microliter.

Figure 20:
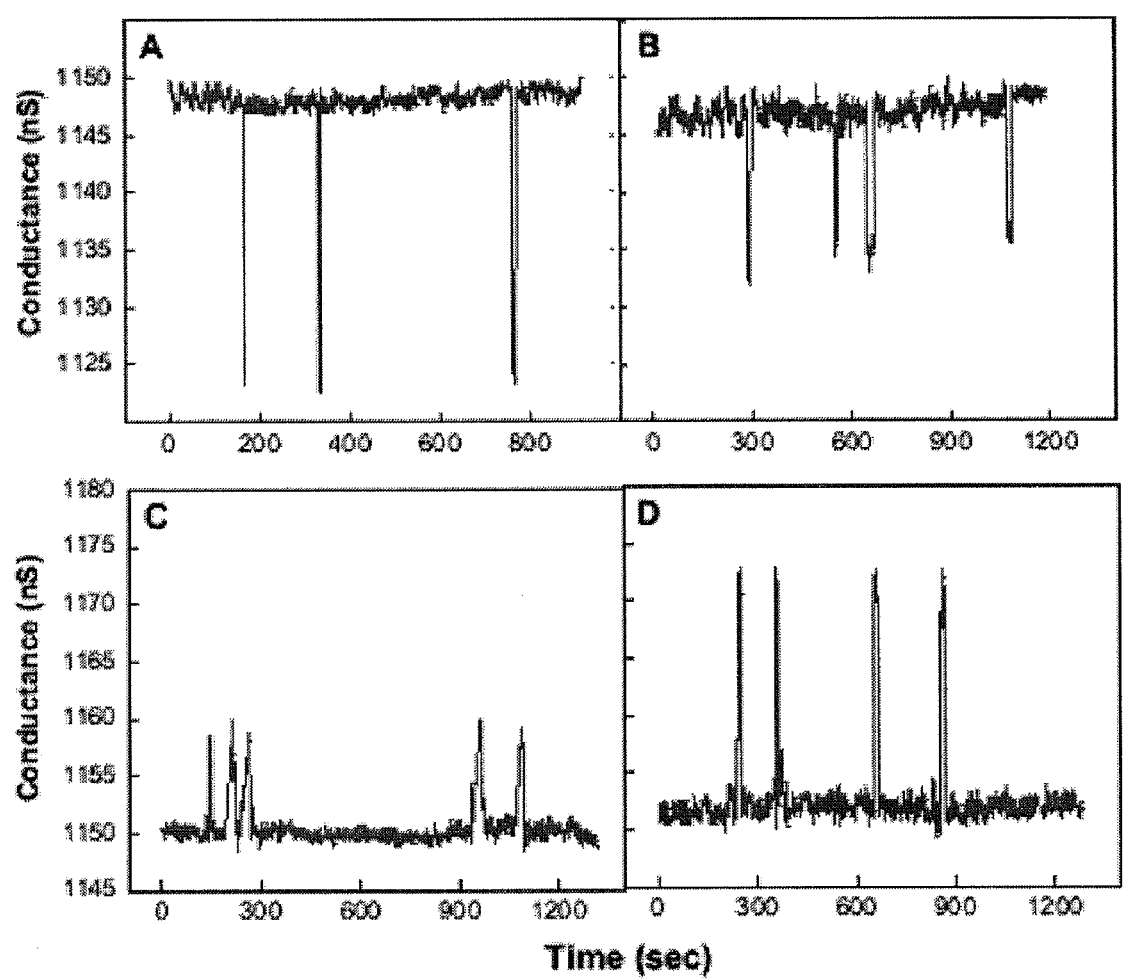
FIGS. 20A-20D illustrate single virus binding, in another embodiment of the invention.
Figure 21A:
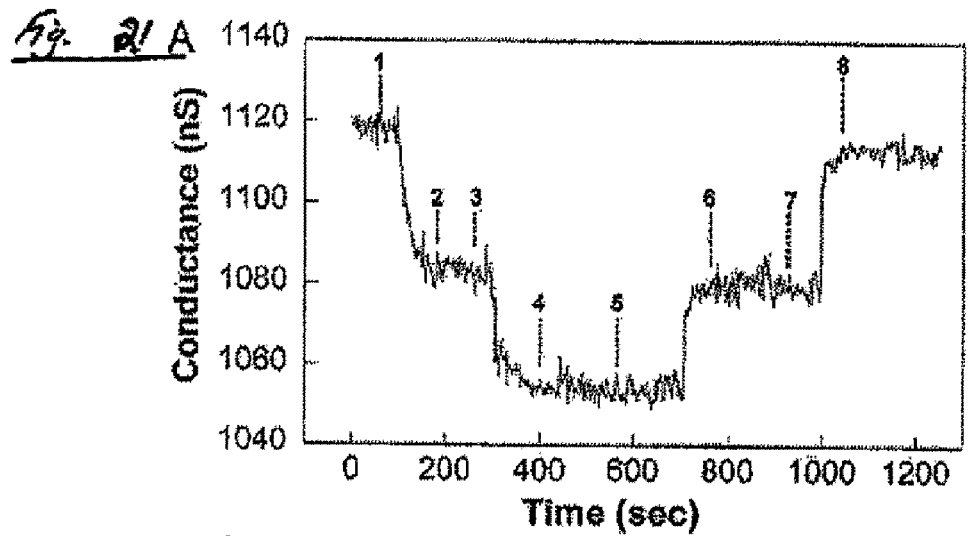
FIGS. 21A-21D illustrate the detection of certain viruses, according to yet another embodiment of the invention.
Figure 21B:
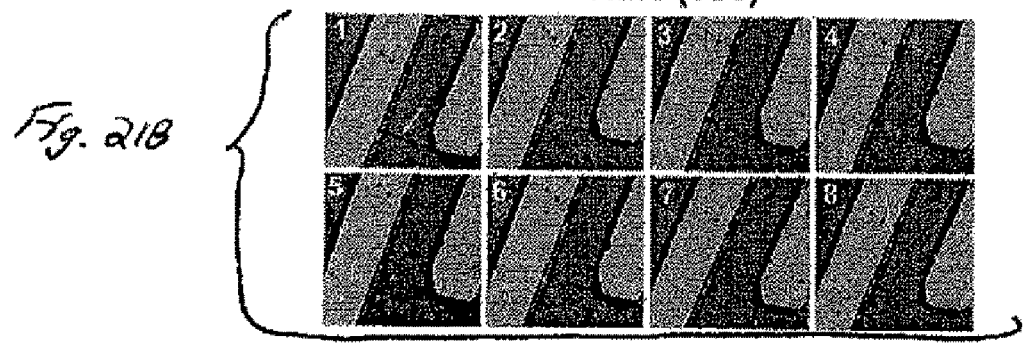
Figure 21C:
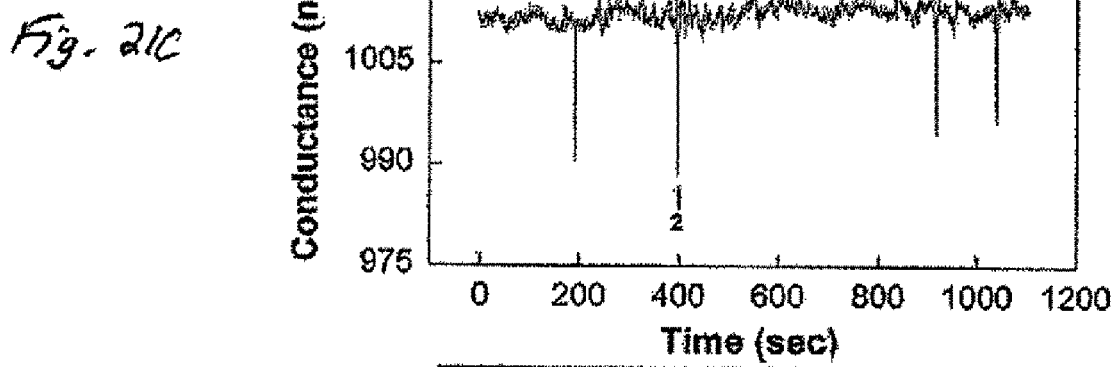
Figure 21D:
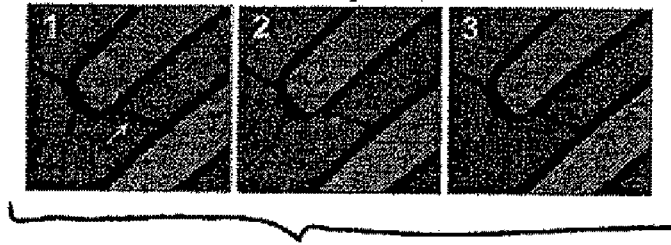
Figure 22A:
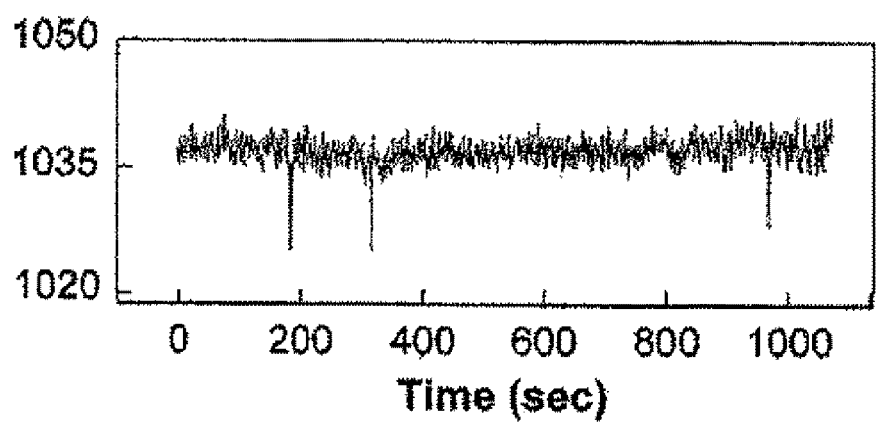
FIGS. 22A-22C illustrate the detection of viruses, according to still another embodiment of the invention.
Figure 22B:
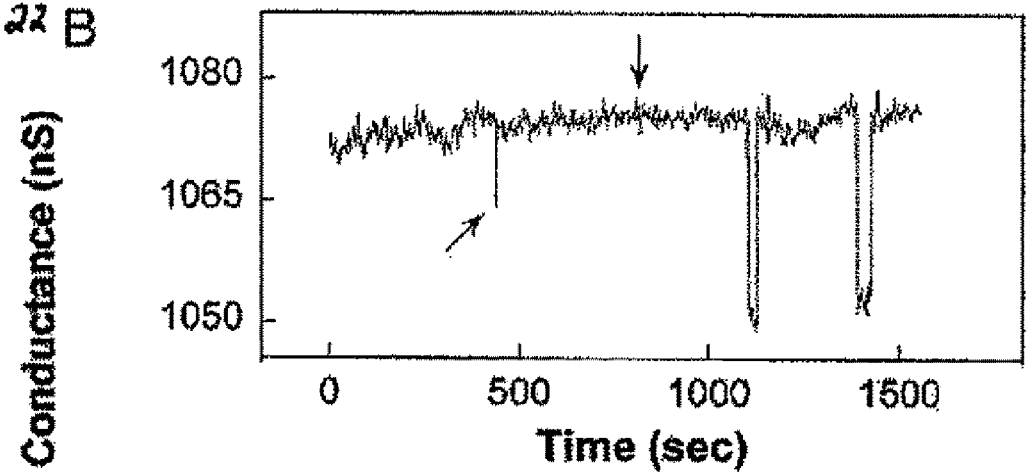
Figure 22C:
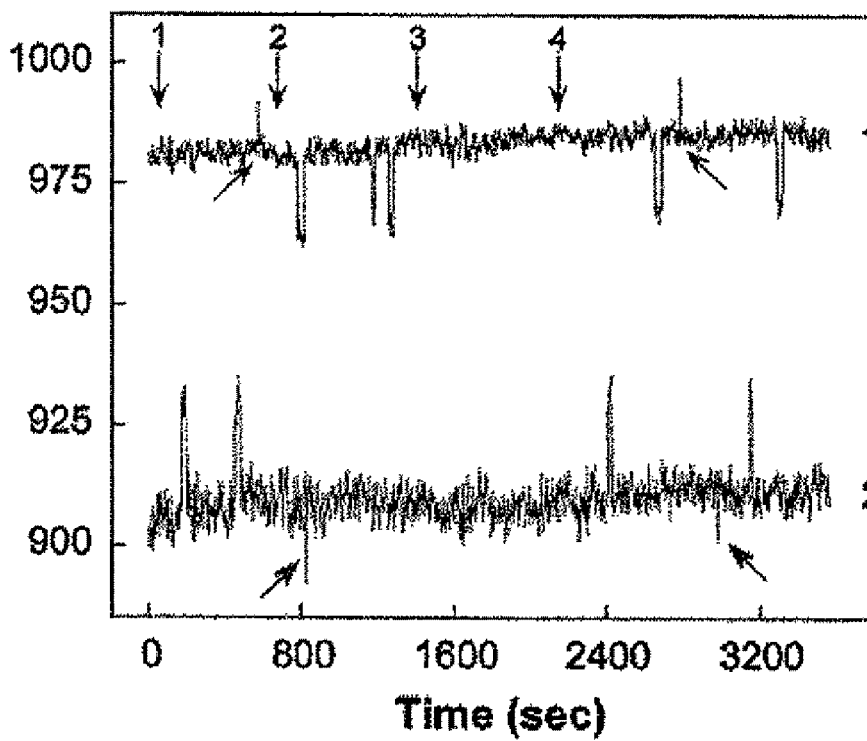

Measurements were also made as a function of pH at constant ionic strength to probe viral surface charge. These data (FIG. 18B and FIG. 20) show that the discrete conductance changes decreased and then increased in magnitude but with opposite sign as the pH increased from 5.5 to 8 with a point of zero conductance change (that is, the isoelectric point) occurring between pH 6.5 and 7.0. The results and estimated isoelectric point were consistent with electrophoretic mobility measurements made by using much higher concentrations and larger quantities of virus. The fact that the p-type nanowire devices show a reduced (increased) conductivity upon binding of single influenza A viruses at pH<7 ($\geq$7) also demonstrated that detection with the nanowire devices may be caused by a field effect and not a change in capacitance as reported for carbon nanotube sensors. More generally, these results suggest that these nanowire devices could be used to determine rapidly isoelectric points for small quantities of viruses and other biomolecules. In addition, the time scale of the discrete changes in conductance associated with binding/unbinding depended on pH (FIG. 20), which suggests that nanowire detectors could be used to assess directly variations in receptor-virus binding kinetics (for different conditions) from the single particle binding/unbinding data. In FIG. 20, the conductance data were recorded as a function of time for a nanowire modified with anti-influenza type A antibody at constant ionic strength for solution pH values of 5.5 (FIG. 20A), 6.5 (FIG. 20B), 7.0 (FIG. 20C), and 8.0 (FIG. 20D). The measurements were carried out with solutions containing 100 virus particles per microliter.

To characterize the discrete conductance changes further, additional simultaneous electrical and optical measurements were performed. Parallel collection of conductance, fluorescence, and bright-field data from a single nanowire device (FIG. 18C) with fluorescently labeled viruses demonstrated that each discrete conductance change corresponded to a single virus binding to and unbinding from the nanowire. The data showed that as a virus particle diffuses near a nanowire device the conductance remains at the baseline value, and only after binding at the nanowire surface does the conductance drop, where the conductance change, 18±1 nS, was similar to that observed with unlabeled viruses; as the virus unbinds and diffuses from the nanowire surface the conductance returns rapidly to the baseline value. Additional experiments showed that a bound virus can sample several nearby positions on the nanowire surface before unbinding, which may explain the smaller variations in conductance in the on state. The two events in FIG. 18C also exhibited similar conductance changes when virus particles bound to distinct sites on the nanowire, and thus demonstrated that the detection sensitivity is relatively uniform along the length of the nanowire. Lastly, these parallel measurements suggest that a virus particle should be in contact with the nanowire device to yield an electrical response, thus suggesting the potential for relatively dense integration without crosstalk.

The selectivity was first investigated by characterizing how variations in the density of the influenza A antibody receptors affect the binding/unbinding properties. Simultaneous conductance and optical data recorded on devices with average antibody coverage about 10 times higher than above (FIGS. 21A-21B) showed sequential binding of virus particles without unbinding on a 5- to 10-min time scale (vs. unbinding on a 20-s time scale in FIG. 18). Sequential unbinding of the viruses was observed after introducing pure buffer solution. These data showed that the unbinding kinetics can be substantially slowed through increases in the density of specific antibodies and provide strong evidence for selective binding of influenza A; that is, the unbinding kinetics may to be slowed as the number of specific antibody-virus contact points increases.

Thus, in FIG. 21, FIGS. 21A-21B show simultaneous conductance (FIG. 21A) and optical (FIG. 21B) vs. time data recorded from a single nanowire device with a high density of anti-influenza type A antibody. Influenza A solution was added before point 1, and the solution was switched to pure buffer between points 4 and 5 on the plot. The bright-field and fluorescence images corresponding to time points 1-8 are indicated in the conductance data; the viruses appear as dots in the images. Each image is 6.5×6.5 micrometers. FIGS. 21C-21D show simultaneous conductance (FIG. 18C) and optical (FIG. 21D) vs. time data recorded from a single nanowire device with a low density of anti-influenza type A antibody. Bright-field and fluorescence images corresponding to time points 1-3 are shown. Each image is 7×7 micrometers. Measurements were made by using solutions containing 100 viral particles per microliters. The solid white arrows highlight the positions of the nanowires in both devices.

In addition, parallel electrical and optical experiments carried out on devices with a low density of specific antibodies (FIGS. 21C-21D) showed discrete conductance changes caused by the interaction of single viruses with an average duration, 1.1±0.3 s. This average on time was about 20 times shorter than observed in FIG. 18, where an intermediate antibody density was used. Analysis showed that some of the conductance changes (e.g., event 2) had a time scale of 1-1.5 s, although other events had a time scale of 0.4±0.1 s that was characteristic of diffusion of the virus past and/or rapid touching of the nanowire surface (see below). Interestingly, further analysis of event 2 showed that the virus rapidly samples two nearby positions on the nanowire surface before unbinding. Overall, these coverage-dependent detection data were consistent with selective detection and the ability to vary unbinding kinetics with the density of specific antibodies. These experiments further suggest that it may be possible to determine the unbinding kinetics from a single antibody or other receptor, and how the interactions are perturbed, for example, by the addition of small molecules.

The delivery of a solution containing influenza A (100 virons per microliter) to a nanowire device functionalized with a high density of anti-adenovirus group III antibodies, which should have no specificity against influenza A, only exhibited discrete conductance changes of short duration, 0.4±0.1 s (FIG. 22A). These short events were consistent with diffusion of the virus past and/or rapid touching of the nanowire surface and can be distinguished on the basis of temporal behavior from selective binding exhibited by devices with a comparable density of specific antibody (FIG. 21A). A more stringent test of selectivity was also carried out by characterizing the response of a device to two different, but structurally similar, viruses, paramyxovirus and influenza A, by using nanowire devices modified with antibodies specific for influenza A (FIG. 22B). Delivery of a solution containing paramyxovirus exhibited only short-duration conductance changes characteristic of diffusion of the virus past and/or rapid touching of the nanowire surface and not specific binding; however, when the solution was changed to one containing influenza A, conductance changes consistent with well defined binding/unbinding behavior similar to that in FIG. 18 were observed. Importantly, these experiments demonstrated that the antibody-modified nanowire devices exhibited good binding selectivity, which is an important characteristic for detection of one or more viruses. These data also showed that the devices were sensitive to single charged virus particles (including the sign of the charge) as they diffuse by and sample the nanowire surface, and this capability finds uses, for example, for charge detection in microfluidic devices.

Lastly, multiplexed detection of different viruses at the single particle level by modifying nanowire device surfaces in an array with antibody receptors specific either for influenza A (nanowire 1) or adenovirus (nanowire 2) was investigated. Simultaneous conductance measurements obtained when adenovirus, influenza A, and a mixture of both viruses are delivered to the devices (FIG. 22C) showed several noteworthy points. Introduction of adenovirus, which, as negatively charged at the pH of the experiment, to the device array yielded positive conductance changes for nanowire 2 with an on time of 16±6 s, similar to the selective binding/unbinding in FIG. 18 for a comparable density of surface receptors. The magnitude of the conductance change for binding of single adenovirus particles differed from that of influenza A viruses, possibly because of differences in the surface charge densities for the two viruses. Shorter, roughly 0.4-s duration positive conductance changes were also observed for nanowire 1. These changes were characteristic of a charged virus diffusing past and rapidly sampling the nanowire element (see above) and may be distinguished from specific binding to the antibody receptors. On the other hand, addition of influenza A yielded negative conductance changes for nanowire 1, with a binding/unbinding behavior similar to that in FIG. 18 under comparable conditions. Nanowire 2 also exhibited short duration negative conductance changes, which may correspond to diffusion of influenza A viral particles past the nanowire device, although these were also distinguished from specific binding events by the temporal response. Significantly, delivery of a mixture of both viruses demonstrates unambiguously that selective binding/unbinding responses for influenza A and adenovirus may be detected in parallel by nanowire 1 and nanowire 2, respectively, at the single virus level.

FIG. 22A shows the conductance vs. time curve recorded from a silicon nanowire device after introduction of influenza A virus solution; the device had a high surface coverage of anti-adenovirus group III antibody. FIG. 22B shows conductance vs. time data recorded from a silicon nanowire device modified with an intermediate density of anti-influenza type A antibody. Initially, a solution of paramyxovirus (50 virons per microliter) was delivered to the device, and at the point indicated by the arrow the solution was changed to one containing influenza A (50 virons per microliter). FIG. 22C shows conductance vs. time data recorded simultaneously from two silicon nanowires elements; one nanowire (nanowire 1) was modified with anti-influenza type A antibody (upper curve), and the other (nanowire 2) was modified with anti-adenovirus group III antibody (lower curve). Arrows 1-4 correspond to the introduction of adenovirus, influenza A, pure buffer, and a 1:1 mixture of adenovirus and influenza A, where the virus concentrations were 50 viral particles per microliter in phosphate buffer (10 micromolar, pH 6.0). Small arrows in B and C highlight conductance changes corresponding to diffusion of viral particles past the nanowire and not specific binding.

These experiments thus show that single viruses may be detected directly with high selectivity, including parallel detection of different viruses, in electrical measurements using antibody functionalized nanowire field-effect transistors. This demonstrated potential, which was achieved with virtually unpurified samples, could impact virus detection for medical and biothreat applications and may exceed the capabilities of existing methods such as PCR and micromechanical devices.

The simplicity, single viral particle sensitivity, and capability of selective multiplexed detection of this approach suggest that this work may lead to useful viral sensing devices. Although parallel detection has been demonstrated for only two distinct viruses in this work, assembly methods have demonstrated much larger arrays of reproducible nanowire devices that can simultaneously screen for the presence of 100 or more different viruses. The potential to carry out multiplexing in large nanowire arrays could be exploited by including nanowires modified with general viral cell-surface receptors and/or antibody libraries. This enables rapid identification of viral families and provide an indication of mutations in samples, e.g., as required for robust medical and bioterrorism detection. Lastly, these capabilities and the potential to characterize a range of virus-receptor interactions provide unique opportunities for fundamental virology and drug discovery.

Additional details about these experiments follow. Silicon nanowires were synthesized by chemical vapor deposition with 20-nm gold nanoclusters as catalysts, silane as reactant, and diborane as p-type dopant with a B/Si ratio of 1:4,000. Arrays of silicon nanowire devices were defined by using photolithography with Ni metal contacts on silicon substrates with a 600-nm-thick oxide layer. The metal contacts to the nanowires were isolated by subsequent deposition of about 50-nm-thick $Si_3N_4$ coating. The spacing between source-drain electrodes (active sensor area) was 2 micrometers in all experiments.

Virus samples were delivered to the nanowire device arrays by using fluidic channels formed by either a flexible polymer channel or a 0.1-mm-thick glass coverslip sealed to the device chip. Virus samples were delivered through inlet/outlet connection in the polymer or holes made through the back of device chip in the case of the coverslip. Similar electrical results were obtained with both approaches, although the latter was used for all combined electrical/optical measurements.

A two-step procedure was used to covalently link antibody receptors to the surfaces of the silicon nanowire devices. First, the devices were reacted with a 1% ethanol solution of 3-(trimethoxysilyl)propyl aldehyde (United Chemical Technologies, Bristol, Pa.) for 30 mM, washed with ethanol, and heated at 120° C. for 15 mM (FIG. 23F, left). Second, mAb receptors, anti-hemagglutinin for influenza A (AbCam, Cambridge, U.K.) and anti-adenovirus group III (Charles River Breeding Laboratories), were coupled to the aldehyde-terminated nanowire surfaces by reaction of 10-100 microgram/ml antibody in a pH 8, 10 mM phosphate buffer solution containing 4 mM sodium cyanoborohydride (FIG. 23F, right). The surface density of antibody was controlled by varying the reaction time from 10 mM (low density) to 3 h (high density). Unreacted aldehyde surface groups were subsequently passivated by reaction with ethanolamine under similar conditions. Device arrays for multiplexed experiments were made in the same way except that distinct antibody solutions were spotted on different regions of the array. The antibody surface density vs. reaction time was quantified by reacting Au-labeled IgG antibodies (Ted Pella, Inc., Redding, Calif.; 5 nm Au nanoparticles) with aldehyde-terminated nanowires on a transmission electron microscopy grid, and then imaging the modified nanowire by transmission electron microscopy, which enabled the number of antibodies per unit length of nanowire to be counted (FIG. 23).

FIG. 23 shows transmission electron microscopy images of nanowires modified with antibodies. The antibodies were labeled with 5-nm gold nanoparticles (Au-NP). Different densities were obtained by varying the nanowire modification time. FIG. 23A shows low antibody coverage. FIG. 23B shows medium antibody coverage. FIG. 23C shows high antibody coverage. FIG. 23D is a summary of data from analysis of at least 10 images per coverage. These values represent a lower limit for true antibody densities since the reactivity of the free antibody may be higher than that of the antibody-NP conjugate. (Scale bars: FIG. 23A, 20 nm; FIG. 23B, 10 nm; FIG. 23C, 20 nm). In FIG. 23E, passivating the surface with ethanolamine prior to exposure to the nanoparticles did not result in any binding of the nanoparticles to the nanoscale wire. FIG. 23F is a schematic diagram of the process used to attach the antibody-gold nanoparticle conjugates to the nanoscale wires.

Different concentration virus solutions were prepared from stocks by dilution in phosphate buffer (10 micromolar, pH 6.0) containing 10 micromolar KCl (assay buffer); influenza type A, $10^9$ to $10^{10}$ particles per ml (Charles River Breeding Laboratories; purified virus supplied in 0.1 M Hepes buffer (pH 7.4), caprolactane inactivated), and unpurified avian adenovirus group III, influenza A, and avian paramyxovirus virus in allantoic fluid, $10^{10}$ to $10^{11}$ particles per ml (Charles River Breeding Laboratories), were used as received after dilution in assay buffer or purified by using a microfiltration device (5,000 rpm, Centricon 30, Millipore). Similar results (sensitivity and selectivity) were obtained with purified and unpurified samples. Viral concentrations were measured by transmission electron microscopy after staining samples with uranyl acetate and by fluorescence microscopy using 1,1'-dioctadecyl-3,3,3',3'-tetramethylindocarbocyanine-labeled viruses.

Electrical measurements were made by using lock-in detection with a modulation frequency chosen as a prime number between 17 and 79 Hz, inclusive. Measurements were independent of frequency within this range. The modulation amplitude was 30 mV and the dc source-drain potential was zero to avoid electrochemical reactions. Conductance vs. time data were recorded while buffer solutions, or different virus solutions, flowed through the microfluidic channel. Viral sensing experiments were performed in the microfluidic channel under a flow rate of 0.15 ml/hr in 10 micromolar phosphate buffer solution containing 10 micromolar KCl at pH 6.0.

Influenza virus solutions containing $10^8$ virus particles per ml were labeled with $DiIC_{18}$ (Molecular Probes) in a manner similar to previous studies. Optical data were acquired by using a Zeiss LSM 510 laser scanning confocal microscope with PMT detectors and water immersion objective (× 60, numerical aperture 1.2). The $DiIC_{18}$ dye was excited at 532 nm. Bright-field and fluorescence images together with conductance data were recorded simultaneously. The bright-field data, which highlight the positions of the nanowire and passivated metal contact electrodes, and fluorescence data were recorded simultaneously with two detectors and combined to show the relative positions of the nanowire and moving virus particles.

Example 7

This example illustrates multiplex detection of various toxins, using another embodiment of the invention. A microfluidic channel in fluidic communication with a microarray of nanowires was used in these experiments. The microarray contained a series of 11 nanoscale wires, some of which were able to bind PSA (prostate-specific antigen) using PSA antibodies (nanowires 1-3), some of which were able to bind cholera toxin (CT) using CT antibodies (nanowires 4 and 5), some of which were able to bind botulinum toxin (BT) using BT antibodies (nanowires 6 and 7), and some of which were passivated using ethanolamine and thus were not sensitive to any analytes (nanowires 8-11).

Figure 24A:
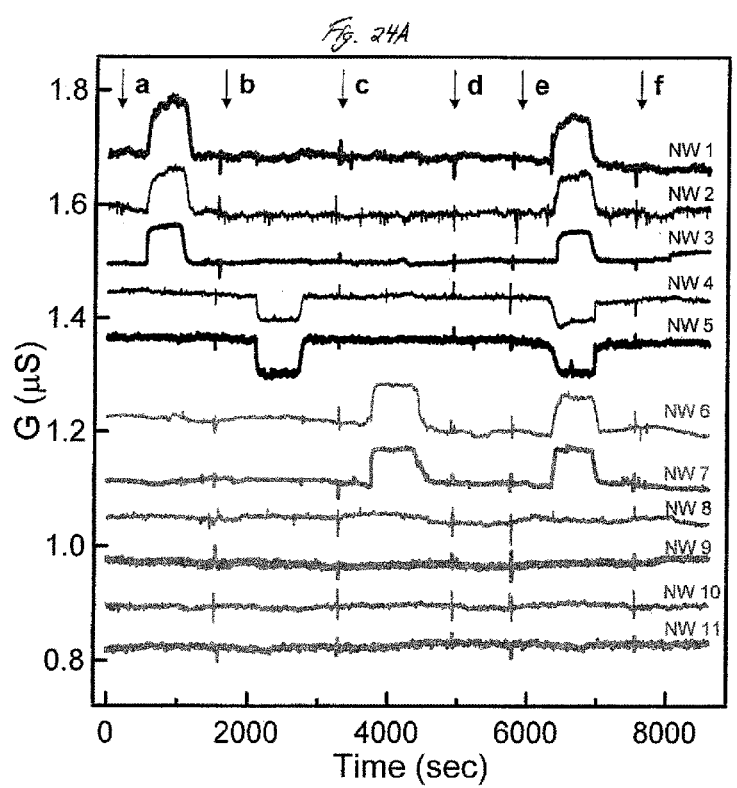

Liquid was urged through the microfluidic channels, containing varying amounts of analytes, and the conductance of each nanoscale wire was measured as a function of time. These results are shown in FIG. 24A (conductance scale is arbitrary). At time (a), 5 ng/ml PSA (an inert protein) was directed into the microfluidic channels. At (b), 5 to ng/ml CT subunit-B was directed into the microfluidic channels; at (c), 5 ng/ml BT; at (d), 10 micrograms/ml HAS (human serum albumin, an inert protein) at (e), 5 ng/ml PSA, 5 ng/ml CT, and 5 ng/ml BT, and (f) the solution included a pre-mixed solution of (e) along with free antibodies to PSA, CT, and BT at 10 microgram/ml.

At (a), only nanoscale wires 1-3 (which contained PSA antibodies) showed a response to the PSA injection. Similarly, at (b), only nanowires 4 and 5 (which contained CT antibodies) showed a response to the CT injection, and at (c), only nanowires 6 and 7 (which contained BT antibodies) showed a response to the BT injection. No response was observed in any of the nanowires during the HAS injection (d). At (e), nanowires 1-7 each showed a response to the simultaneous injection of PSA, CT, and BT. However, at (f), no response was observed in any of the nanoscale wires.

Figure 24B:
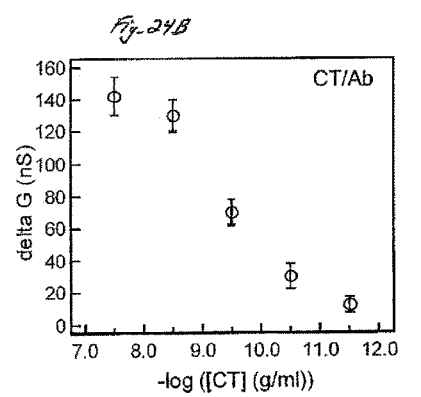
Figure 24C:
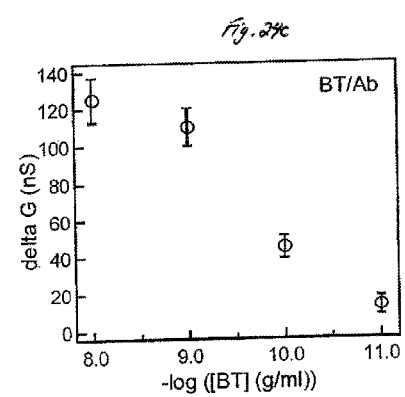

FIGS. 24B and 24C show the sensitivity of the device for CT antibodies (FIG. 24B) and BT antibodies (FIG. 24C). Both figures show that the change in conductance of the nanoscale wire detectors is a function of the concentration of CT or BT.

A similar experiment using gangliosides instead of antibodies, is illustrated in FIG. 24D. In these experiments, 8 nanoscale wires were simultaneously used. Nanoscale wires 1-3 included GT1b (sensitive to BT), nanoscale wires 4 and 5 included GM1 (sensitive to CT), and nanoscale wires 6-8 included asialo-GM1 which is not sensitive to either CT or BT. The experimental apparatus was similar to the one described above.

At time (a), 5 ng/ml of BT was directed into the microfluidic channels; at (b), 100 ng/ml PSA; at (c), 5 ng/ml CT and 5 ng/ml BT; at (d), 5 ng/ml CT; and at (e) 10 microgram/ml of BSA (bovine serum albumin, an inert protein). At certain times, as shown by the arrows at the bottom of FIG. 24B, injections of buffer (phosphate buffer, 10 micromolar, pH of 6.7) were also added to the microfluidic channel BT is negatively charged and CT is positively charged at this pH.

At (a), only nanoscale wires 1-3 (containing GT1b) showed a response to the BT injection. At (b), no response was observed in any of the nanowires for the PSA injection. At (c), nanoscale wires 1-3 (containing GT1b) and nanoscale wires 4 and 5 (containing GM1) both showed a response to the combined CT/BT injection. At (d), nanowires 4 and 5 showed a response to the injection of CT only. At (e), no response was observed in any of the nanowires for the BSA injection.

FIGS. 24E and 24F show the sensitivity of the device for CT with GM1 (FIG. 24E) and BT with GD1 (FIG. 24C). Similar to the previous graphs, both figures show that the change in conductance of the nanoscale wire detectors is a function of the concentration of CT or BT.

Figure 24G:
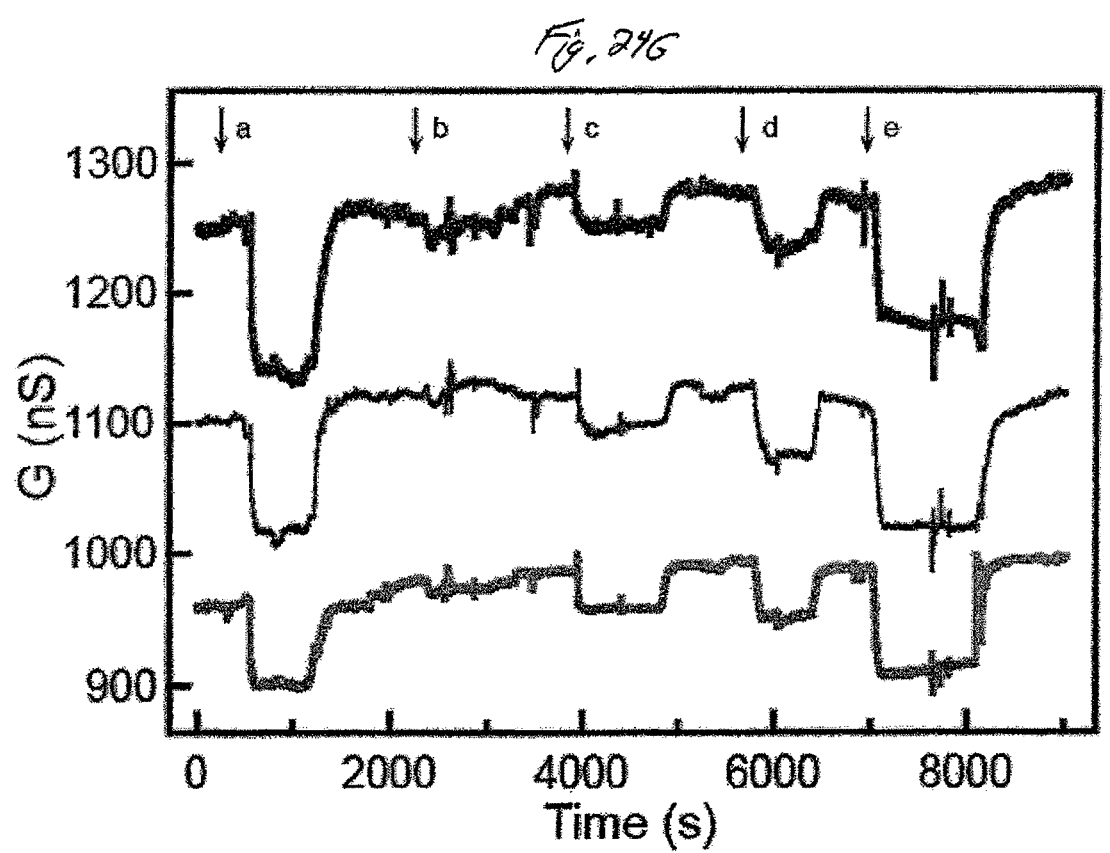
Figure 24H:
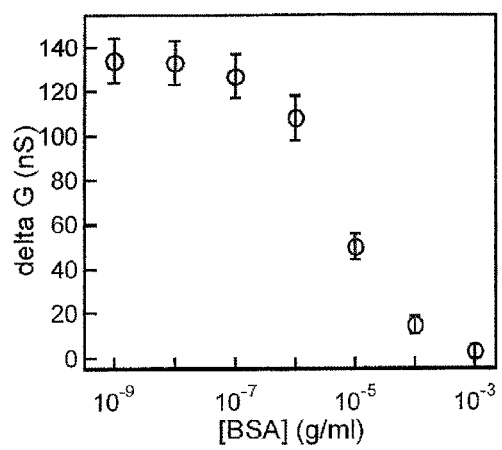

In FIG. 24G, 3 nanoscale wires including GM1 (sensitive to CT), were exposed to various injections, as follows (the buffer was 10 micromolar phosphate buffer at a pH of 6.7): (a) 5 ng/ml CT; (b) 20 microgram/ml BSA; (c) 5 ng/ml CT and 20 microgram/ml of BSA; (d) 5 ng/ml CT and 10 microgram/ml BSA; (e) 5 ng/ml CT and 1 microgram/ml BSA. The nanoscale wires in FIG. 24G each show large responses in conductivity for CT only, and somewhat smaller responses for CT and BSA solutions. However, it should be noted that detection of a change in conductivity was still evident even when the BSA was at a concentration of 4,000 times greater than CT (c). Additional experiments (data not shown) illustrate this sensitivity in FIG. 24H, as a plot of change in conductance verses the concentration of BSA for the detection of 5 ng/ml CT. Detection of 5 ng/ml CT was still possible even in concentrations of 1 mg/ml BSA (i.e., at a concentration of 200,000 times greater than CT.

Figure 24I:
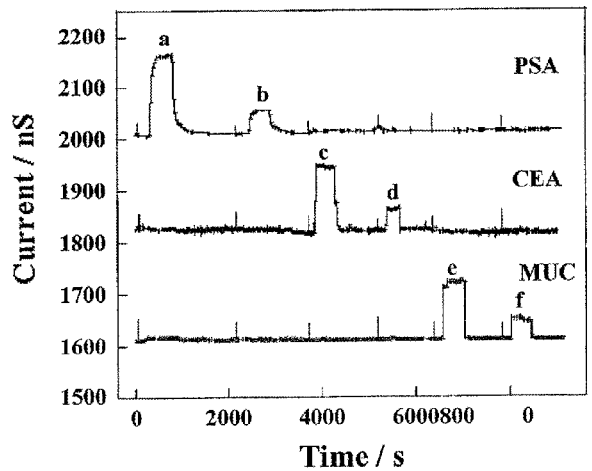

Yet another experiment, showing multiplexed cancer marker detection, is shown in FIG. 24I. In this figure, three nanoscale wires were prepared, having antibodies to PSA, carcinoembryonic antigen ("CEA"), and mucin-1 ("MUC"). The three nanoscale wires were exposed to various injections, as follows: (a) 0.9 ng/ml PSA; (b) 1.4 pg/ml PSA; (c) 0.2 ng/ml CEA; (d) 2 pg/ml CEA; (e) 0.5 ng/ml mucin-1; and (f) 5 pg/ml mucin-1. FIG. 24I shows that each nanoscale wire responded to its corresponding marker, but did not respond to any of the other markers.

Thus, this example illustrates that various analytes can be independently and specifically determined, even when the analytes are all present in a given sample.

Example 8

This example illustrates the preparation of a passivated nickel electrode, in accordance with an embodiment of the invention. In FIG. 25A, a substrate 250 is shown. On top of substrate 250 is a liftoff resist 252, a photoresist 254, and a nickel layer 256. In some locations of the substrate, where no liftoff resist (or photoresist) is present, the nickel layer 257 directly contacts the substrate. Thus, using suitable liftoff resist patterns, various nickel electrodes, other metal electrodes, and/or other connects may be to patterned on the surface of the substrate. The nickel layer (or other metal layer) can be used, for example, as an electrode that may be in contact with a semiconductor nanoscale wire.

On top of the nickel layer, $SiN_x$ 259 is directly deposited onto the nickel layer using PE-CVD deposition, forming layer 258 as shown in FIG. 25B. Layer 258 is deposited onto the nickel layer 256 that is positioned on top of the photoresist layer, as well as on the nickel layer 257 that is directly deposited on the substrate. In FIG. 25C, liftoff resist 252 is removed, thereby also removing photoresist layer 254 and nickel layer 256. Remaining on the substrate 250 is the nickel layer 257, forming an electrode, which is passivated by a layer of $SiN_x$ 258. A photomicrograph, determined optically, of such a passivated nickel electrode is shown in FIG. 25D. FIG. 25E is cross-section of the height profile of FIG. 25D at the line 251, as determined by AFM.

FIGS. 25F and 25G illustrate the leakage current for a nickel electrode passivated with $SiN_x$ as described above. In each case, the leakage current increased upon exposure of the nickel electrode to 100 mM KCl.

FIG. 25H is a table illustrating that the amount of leakage current observed in buffer solution decreases with the degree of passivation of the nickel electrode with $SiN_x$. The leakage current of the passivated electrodes generally decreased by approximately at least in order of magnitude relative to no passivation.

Example 9

This example illustrates a detailed protocol for realizing nanowire electronic sensors. First, the growth of uniform, single crystal silicon nanowires, and subsequent isolation of the nanowires as stable suspensions, are outlined. Second, the fabrication of addressable nanowire device arrays is discussed. Third, covalent modification of the nanowire device surface with specific receptors is described. Last, measurements of the electrical response from devices and sensors are detailed. The silicon nanowire devices have demonstrated applications for label-free, sensitive, and highly-selective real-time detection of a wide range of biological and chemical species, including proteins, nucleic acids, small molecules, and viruses.

In this example, semiconductor nanowires are configured within field-effect transistors (FETs), where the FETs exhibit a conductivity change in response to variations in the electric field or potential at the surface. In a typical FET, a to semiconductor such as p-type silicon (p-Si) is connected to metal source and drain electrodes through which a current is injected and collected, and the conductance of the semiconductor device is controlled by a third gate electrode capacitively coupled through a dielectric layer. In the case of p-Si, applying a positive gate voltage can deplete carriers and reduce the conductance, while applying a negative gate voltage can lead to an accumulation of carriers and an increase in conductance. The dependence of the FET conductance on gate voltage also allows direct, electrically-based sensing, since the electric field resulting from binding of a charged species to the surface may be analogous to applying a voltage using a gate electrode.

Silicon nanowires have a one-dimensional morphology and a nanometer scale cross-section that allows depletion or accumulation of carriers in the "bulk" of the device when a species binds to the surface. Silicon nanowires are used in this example since this material represents one of the best characterized examples of semiconductor nanowires with the structure, size and electronic properties reproducibly controlled, although other materials will also work, as previously described. Specifically, silicon nanowires can be prepared as single-crystal structures with controllable diameters as small as 2-3 nm, and moreover, as both p-type and n-type material with well-defined and reproducible high-performance FET device properties.

The sensor was prepared using a silicon nanowire device by linking recognition receptor groups to the surface of the nanowire. The native silicon oxide coating on silicon nanowires makes this receptor linkage relatively straightforward since extensive data exists for the chemical modification of silicon oxide or glass surfaces. When the sensor device with surface receptors was exposed to a solution containing a macromolecule like a protein, which may have a net negative (or positive) charge in aqueous solution, specific binding will lead to an increase (decrease) in the surface negative charge and an increase (decrease) in conductance for the nanowire device.

These nanowires can be used in for real-time, label-free and highly-sensitive detection of a wide-range of species, including proteins, nucleic acids, small molecules and viruses, in either single element or multiplexed formats, as discussed herein. In some cases, detection may involve a change in charge at the nanowire surface associated with binding and/or unbinding.

TABLE 2

Reagents

Silicon wafer substrate for growth and electrical measurement (3' N<100>, <0.005 ohm-cm, 356-406 micrometers thick with 600 nm thermal oxide, SSP prime grade, Nova Electronic Materials Ltd.)
Poly-L-lysine (0.1% w/v aqueous, Ted-Pella Inc.)
Gold nanoparticles, 20 nm diameter (Ted-Pella Inc.)
Gases for growth: silane (99.9+%, Voltaix Inc.), diborane (97 ppm in hydrogen, Voltaix Inc.), phosphine (1000 ppm in hydrogen, Voltaix Inc.), argon (99%, Matheson Tri-gas Inc.), hydrogen (99.9995%, Matheson Tri-gas Inc.)
S1805 photoresist (Shipley, Inc.)
LOR3A lift-off resist (MicroChem Corporation)
MF319 developer (Shipley Inc.)
Remover PG (MicroChem Corporation)
Buffered hydrofluoric acid (Fluoride-bifluoride-hydrofluoric acid buffer, Transene Inc.)
Gold slug (99.995%, 3.175 mm dia × 3.175 mm length, Alfa Aesar Inc.)
Nickel slug (99.995%, 3.175 mm dia × 3.175 mm length, Alfa Aesar Inc.)
Chromium coated tungsten wire (Cr 99.888%, W 96.5+%, 1.8 mm dia × 10 cm length, Alfa Aesar Inc.)
3-(trimethoxysilyl)propyl aldehyde (90%, United Chemical Technologies Inc.)
Carbon conductive tape (double coated, 8 mm wide, Ted Pella Inc.)
0.2 micrometer cut-off acrodisc syringe filter (0.2 micron HT tuffryn membrane, non-pyrogenic, #4192, Pall Corporation).
Polydimethylsiloxane (SYLGARD 184 silicone elastomer kit, BROWNELL Inc.)
Polyethylene tubing (ID/OD = 0.38/1.09 mm, Becton Dickinson Inc.)
Ethanolamine (99.5%, Sigma-Aldrich Inc.)
Buffer for antibody binding (10 mM phosphate buffer, pH 8.4)
Buffer for ethanolamine blocking (100 mM ethanolamine in 10 mM phosphate buffer, pH 8.4)
Buffer for protein sensing (10 micromolar phosphate buffer, containing 2 micromolar KCl, pH 7.4)
Prostate Specific Antigen Antibody (mouse monoclonal PSA antibody, without bovine serum albumin (BSA) and azides, NeoMarkers Inc.)
Prostate Specific Antigen (EMD Bioscience Inc.)
Bovine Serum Albumin (New England BioLabs Inc.)

Equipment

Nanowire chemical vapor deposition synthesis apparatus
Optical microscope (BX51, Olympus, Inc.)
Scanning electron microscope (SEM) for microscopic characterization of nanowires and devices (LEO982 field emission SEM, Zeiss Inc.)
Transmission electron microscope (TEM) for microscopic characterization of nanowires (JEOL2010, JEOL Inc.)
Sonicator (2510, Branson Inc.)
Hotplate (PMC720, Fisher Scientific Inc.)
Spin-coater (PWM32, Headway Research Inc.)
Photolithography mask aligner (2130-C2, AB-M Inc.)
Metal evaporator (thermal evaporator, Sharon Vacuum Inc.)
Rapid thermal annealer (RTA) (610, Metron Technology Inc.)
Oxygen plasma cleaner (PJ Benchtop, AST Products Inc.)
Plasma-enhanced chemical vapor deposition (PECVD) for silicon nitride deposition (Cirrus-150, Nexx Inc.)
Probe station (TTP-4, Dessert Cryogenics Inc.)
Semiconductor property analyzer (4156C, Agilent Inc.)
Wire-bonder (8850, West Bond Inc.)
Electrical measuring set-up, hardware and software
Syringe pump for sample delivery (PhD2000, Harvard Apparatus Inc.)
Centrifuge (epp5804r, VWR International Inc.)
Lock-in amplifier (SR830, DSP dual-phase, Stanford Research Systems Inc.)
Current pre-amplifer (1211, DL Instrument Inc.)
Multifunction I/O adaptor panel (BNC-2090, National Instrument Inc.)
DAC card (PCI-6030E, National Instrument Inc.)

Figure 26A:
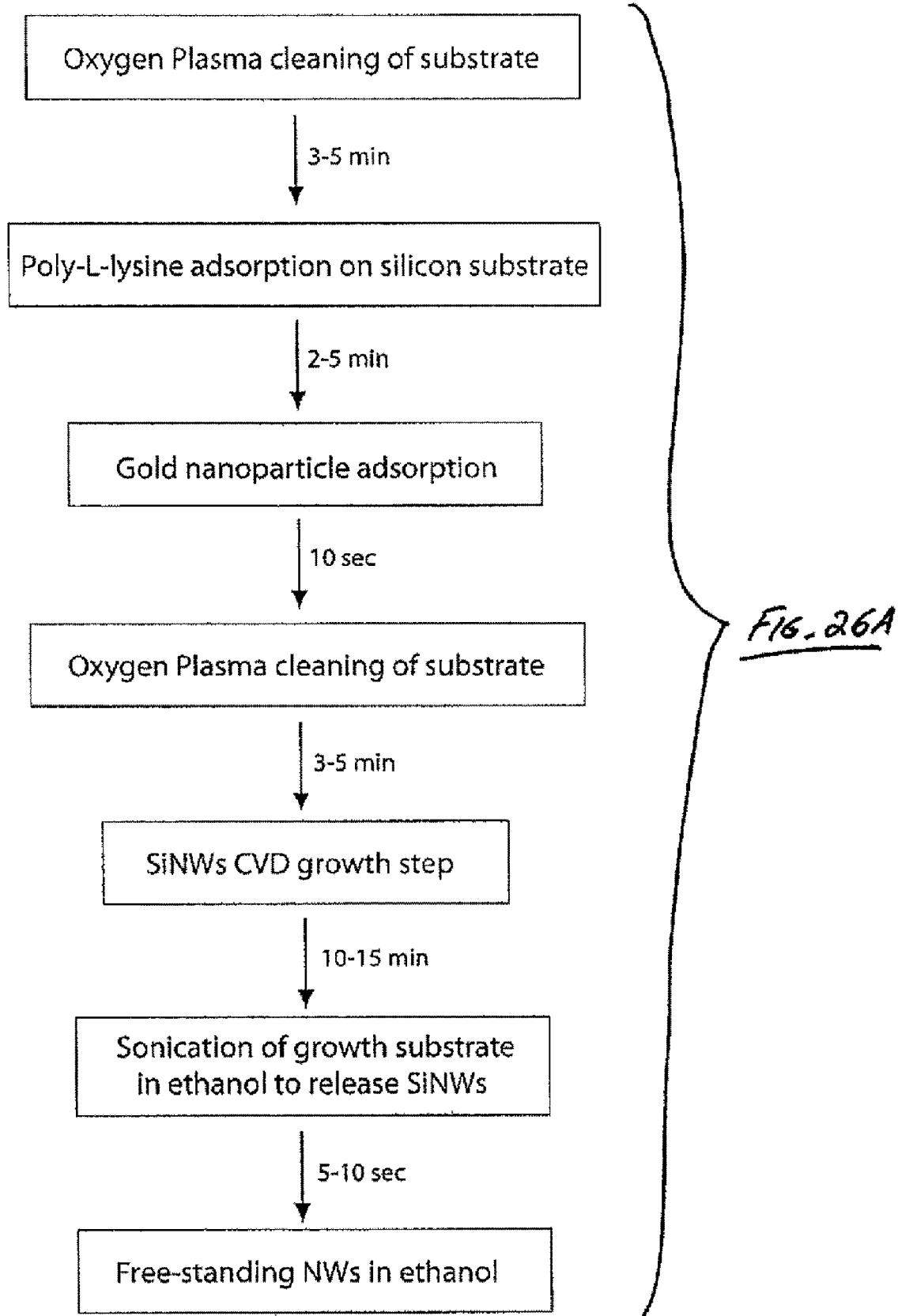
FIGS. 26A-26C are schematic diagrams illustrating processes useful in making certain embodiments of the invention.

The overall steps involved in the synthesis and isolation of silicon nanowires (SiNWs) are shown in FIG. 26A. The synthesis in this particular example involved nanoparticle-catalyzed vapor-liquid-solid (VLS) growth on an oxidized silicon substrate using gold nanoparticles and silane as the catalyst and silicon-reactant, respectively. The diameter of gold nanoparticle catalyst defined the diameter of the resulting silicon SiNWs. The isolation process involves removal of the SiNWs from the substrate into a solution suspension. The specific steps for SiNW synthesis and isolation are as follows.

1. The silicon dioxide ($SiO_2$) surface of a 1×2 $cm^2$ piece of silicon wafer (the growth chip) was cleaned with oxygen plasma: 100 W and 50 sccm $O_2$ for 200 sec. This plasma treatment removed organic residues and rendered the surface hydrophilic.

2. The clean surface of the growth chip was covered with a 0.1% poly-L-lysine (about 200 microliters), and the solution was allowed to stand for 2 min.

3. The poly-L-lysine was then removed by rinsing with a stream of DI water from a squeeze bottle for 5 sec (about 10 ml), and then surface was dried using a gentle stream of nitrogen gas for 10 sec.

4. The growth chip surface was covered with a solution of 20 nm Au nanoparticles (diluted 1:4, v/v with DI water; final concentration about $2 \times 10^{11}$ particles/ml). The solution was allowed to stand for 10 sec, and then surface was rinsed with a stream of DI water from a squeeze bottle for 5 sec (about 10 ml), and then surface was dried using a gentle stream of nitrogen gas for 10 sec. The negatively charged Au nanoparticles were electrostatically bound to the positively charged poly-L-lysine covered growth chip surface.

5. The growth chip with Au nanoparticles was cleaned in an oxygen plasma: 100 W and 50 sccm $O_2$ for 5 min The cleaning step allowed uniform nucleation and nanowire growth.

6. The clean growth chip was then placed in the middle of the quartz reactor tube inside the CVD growth furnace.

7. The reactor was evacuated to less than 3 mtorr and the temperature was raised to 460° C. in a 10 sccm Ar flow and total pressure of 10 mtorr.

8. When the growth temperature was stable, silane ($SiH_4$), which was the silicon reactant source, and dopant (e.g., diborane ($B_2H_6$) for p-type or phosphine ($PH_3$) for n-type nanowires) were introduced into the reactor. The typical growth conditions for p-type SiNWs were 10 sccm Ar, 6 sccm $SiH_4$, 7.5 sccm $B_2H_6$ (97 ppm in $H_2$), total chamber pressure 25 torr, temperature of 460° C., and growth time of about 10 min, where typical growth rates were 1.2-1.5 micrometers/min. The typical growth conditions for n-type SiNWs were 30 sccm $H_2$, 8 sccm $SiH_4$, 2 sccm $PH_3$ (1000 ppm in $H_2$), total chamber pressure 40 torr, temperature of 460° C., and growth time of about 15 min, where typical growth rates were 0.8-1.0 micrometers/min. At the end of the growth, the reactant flow was terminated, the reactor tube was evacuated (3 mtorr), and the furnace was shut-down and opened for cooling (about 30 min).

9. The nanowires were removed from the growth chip and suspended in 1-2 ml of ethanol by sonication for 5-10 seconds. The ethanol suspension of SiNWs was a transparent yellow-brown color. The nanowire solution was checked for uniformity by placing a drop onto a silicon chip, and imaging by SEM.

Figure 26B:
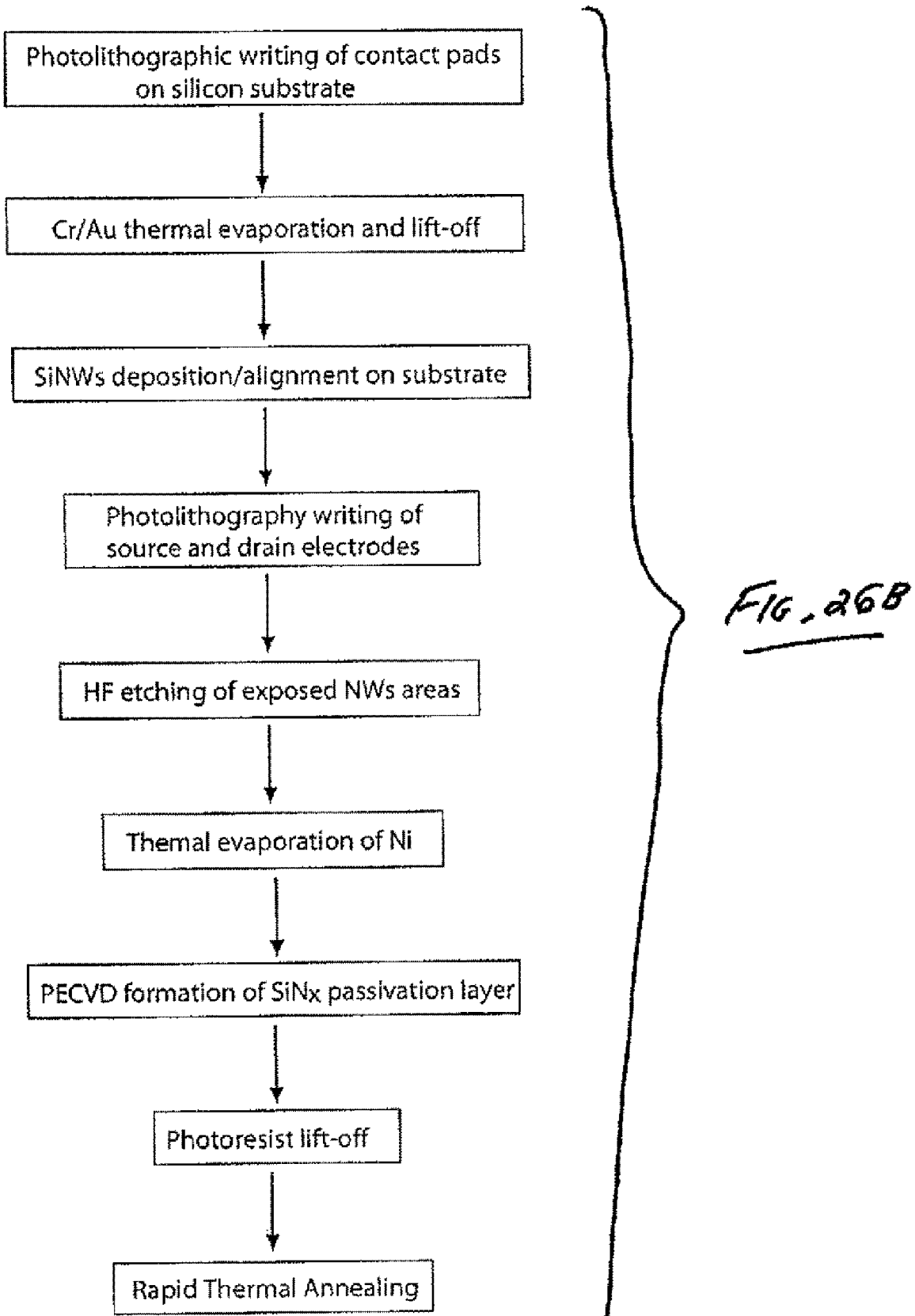

The steps involved in fabrication of nanowire electronic devices are shown in FIG. 26B. The fabrication of SiNW FET devices is relatively straightforward, and combines bottom-up assembly of the nanowires on a device chip together with a single step of photolithography to make contacts. Following FIG. 26B, the specific steps for SiNW synthesis and isolation were as follows.

10. The silicon dioxide ($SiO_2$) surface of a 2×2 $cm^2$ piece of silicon wafer (the sensor chip) was cleaned with oxygen plasma: 100 W and 50 sccm $O_2$ for 200 sec.

11. A two-layer photoresist of LOR3A and S1805 was deposited onto the sensor chip by spin coating. First, 0.5 ml of LOR3A was deposited by spinning at 500 rpm/5 sec, then 4000 rpm/40 sec, followed by baking on a hotplate at 185° C. for 5 min; the LOR3A layer thickness was about 300 nm Second, 0.5 ml of S1805 was deposited by spinning at 500 rpm/5 sec, then 4000 rpm/40 sec, followed by baking on a hotplate at 115° C. for 90 sec; the S1805 layer thickness was about 500 nm.

12. Photolithography (ABM photoaligner, wavelength 350-430 nm, exposure to time 0.8 sec) was used to define the outer contact pads and interconnects using the photomask shown in FIG. 5F.

13. The photopatterned chip was immersed in MF319 developer for 1 min, and then rinsed by immersing in DI water (30-50 ml) with gentle agitation for 1 min. The chip was dried in a stream of nitrogen gas for 30 sec.

14. The sensor chip was cleaned using an oxygen plasma: 30 W and 50 sccm $O_2$ for 60 sec, and then placed in a thermal evaporator.

15. The contact pads were metallized by sequentially depositing Cr and Au after the chamber pressure was reduced to the $10^{-7}$ torr range. 5 nm of Cr was deposited at 0.1 nm/sec followed immediately by 60 nm of Au at 0.1 nm/sec within the multi-source thermal evaporator.

16. The remaining resist was lifted off with PG Remover (immersion in 20-30 ml, 70° C., 30 min), washed with (i) acetone and (ii) ethanol for 5-10 sec/each using squeeze bottles, and then dried for 10 sec in a stream of nitrogen gas.

17. The sensor chip with outer metal contact pads was cleaned using an oxygen plasma: 100 W and 50 sccm $O_2$ for 200 sec.

18. The nanowire-containing ethanol solution was deposited drop-wise on the clean oxide surface of the sensor chip using 1 microliter aliquots, where typically on the order of 20 drops were used. The drops were deposited in the central region of the chip where the devices were made, and each drop was allowed to evaporate before the next drop was deposited. The nanowire density for device design used in the sensor chips was 1-2 nanowires per 100 $micrometer^2$, where the nanowire density was estimated using dark-field optical microscopy. Alternatively, the SiNWs could be aligned on the growth chip by using solvent flow-induced alignment or Langmuir-Blodgett methods.

19. A two-layer photoresist of LOR3A and S1805 was deposited onto the sensor chip by spin coating. First, 0.5 ml of LOR3A was deposited by spinning at 500 rpm/5 sec, then 4000 rpm/40 sec, followed by heating at 185° C. for 5 min; the LOR3A layer thickness was about 300 nm. Second, 0.5 ml of S1805 was deposited by spinning at 500 rpm/5 sec, then 4000 rpm/40 sec, followed by heating at 115° C. for 90 sec; the S1805 layer thickness was about 500 nm.

20. Photolithography (ABM photoaligner, wavelength 350-430 nm, exposure time 0.8 sec) was used to define the source/drain electrodes and inner interconnects using the photomask shown in FIG. 5F. The photomask was aligned using an optical microscope to the pattern previously defined above using common alignment markers.

21. The photopatterned chip was immersed in MF319 developer for 1 min, and then rinsed by immersing in DI water (30-50 ml) with gentle agitation for 1 min. The chip was dried in a stream of nitrogen gas for 30 sec.

22. The sensor chip was cleaned using an oxygen plasma: 30 W and 50 sccm $O_2$ for 60 sec, and then placed in a thermal evaporator.

23. Prior to placing the sensor chip in the metal evaporator, the contact regions were etched in buffered HF solution to remove oxide on the SiNW surface. The chip was immersed completely in HF solution for 5-8 sec, immersed in 30 ml of DI water for 10 sec, dried for <10 sec in a stream of nitrogen gas, and then immediately placed in the metal evaporator.

24. The source/drain contacts and inner interconnects were metallized by depositing 60 nm Ni at 0.1 nm/sec; the chamber pressure prior to the start of evaporation was in the $10^{-7}$ torr range.

25. After Ni deposition, the sensor chip was removed from the evaporator and transferred to the PE-CVD chamber for silicon nitride deposition. The $Si_3N_4$ passivation layer was 20-30 nm thick and deposited with the following conditions: Ar (20 sccm), $SiH_4$ (40 sccm, 3% in Ar), $N_2$ (6 sccm), total chamber pressure of 5 mtorr, microwave power of 375 W, and a deposition time of 600 sec.

26. The remaining resist was lifted off with PG Remover (immersion in 20-30 ml, 70° C., 30 min), washed with (i) acetone and (ii) ethanol for 5-10 sec/each using squeeze bottles, and then dried for 10 sec in a stream of nitrogen gas.

27. The metallized sensor chip was annealed using a rapid thermal annealer at 380° C. for 2 min in forming gas (10% H2/90% N2) to form low-resistance NiSi contacts at the interfaces between the SiNWs and source/drain Ni electrodes.

28. The sensor chips were examined at completion of annealing by optical microscopy. Metal contact pads, interconnection lines, and source drain contacts appeared well-formed, continuous, and sharp with a good yield of single SiNWs spanning source/drain electrodes. Sensor chips with a low-yield of nanowire devices, considerable nanowire aggregation and/or poorly defined/broken metal lines were discarded.

The basic electrical properties of the SiNW devices on the sensor chip were measured, as these provide a means for quality control prior to completion of the sensor device for use. Device measurements in air were used to identify good devices and any unsuitable devices. Subsequent measurements in aqueous solution were useful for testing integrity of good devices identified in air. The specific steps for SiNW device characterization were as follows.

29. For air characterization, individual SiNW devices on the sensor chip were connected to measurement electronics (semiconductor property analyzer) using a probe station. The probes were brought into contact with the outer metal contact pads on the sensor chip, while viewing optically.

30. The individual SiNW devices on the chip were tested to identify suitable and unsuitable devices. The current ($I_{ds}$) versus drain-source voltage ($V_{ds}$) for several gate voltages ($V_{gs}$) and Ids versus $V_{gs}$ for $V_{ds}=1V$ were measured. Data representative of suitable p-type and n-type SiNW devices are shown in FIGS. 27A-27B and FIGS. 27C-27D, respectively. In FIGS. 27A and 27C, the curves (as followed the direction of the arrow) correspond to gate voltage ($V_g$) values of −5, −4, −3, −2, −1, 0, 1, 2, and 3 V, respectively for a typical p-type SiNW FET (FIG. 27A) and a typical n-type SiNW FET (FIG. 27C). FIGS. 27B and 27D illustrate $I_{ds}$ V. $V_g$ data recorded for the nanowires shown in FIGS. 27A and 27C, respectively, plotted on linear (left) and logarithmic (right) scales at a $V_{ds}$ of 1V.

Figure 28A:
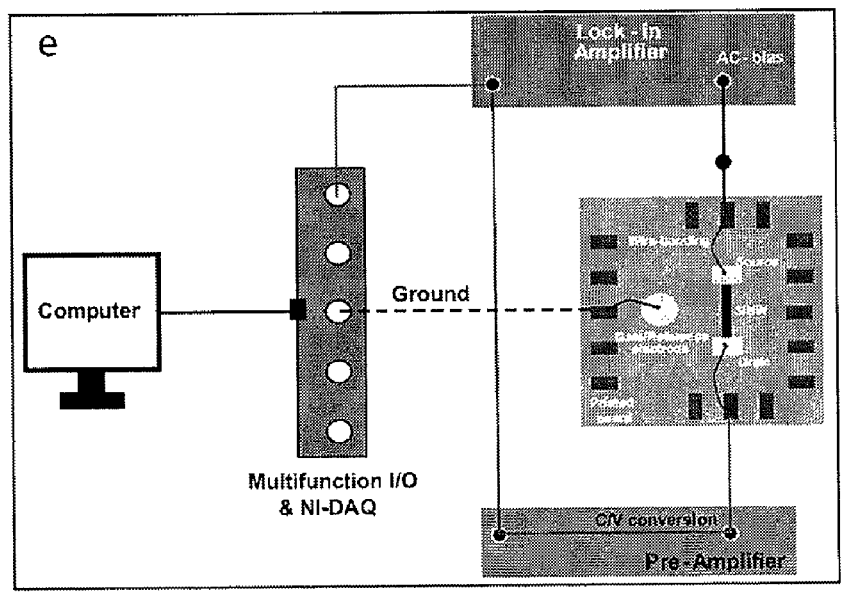
FIGS. 28A-28C illustrate the measurement of a nanowire FET, in yet another embodiment of the invention.

In some cases, the electrical properties of SiNW devices were also measured in aqueous solution. This process allows testing of the integrity of the $Si_3N_4$ passivation, and testing of the electronics and microfluidics that will be used in sensor experiments. The overall set-up for solution measurements and sensing are detailed with reference to FIG. 28A.

31. The sensor chip was mounted on a chip-carrier using double-sided conductive carbon tape, and then wire-bonding was used to connect contact pads of good devices to the 24 output pads of the chip carrier. This allowed about 11 devices and a reference/gate electrode to be connected, although a larger number of devices is also to possible with shared source electrodes.

32. A single channel microfluidic device was clamped on the chip carrier such that the channel overlaps the central region of the sensor chip, which contains the SiNW devices. The channel (0.5 mm width×0.05 mm height×10 mm length) was made from polydimethylsiloxane (PDMS) using published procedures. Solution was drawn into the channel through 0.38 mm ID polyethylene tubing attached to the inlet using a syringe pump attached to the channel outlet using the same size tubing. Typical flows used in the experiments were 0.3-0.4 ml/hour.

Figure 28B:
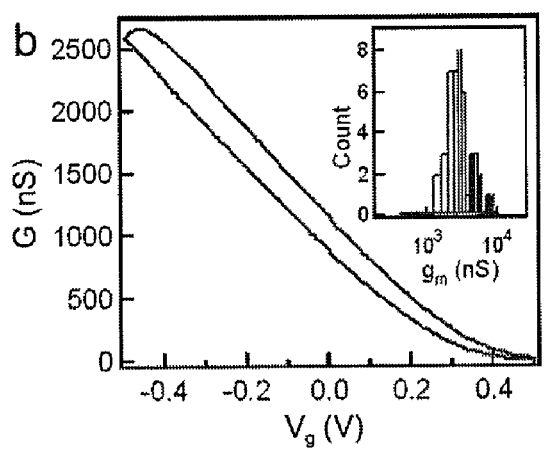
Figure 28C:
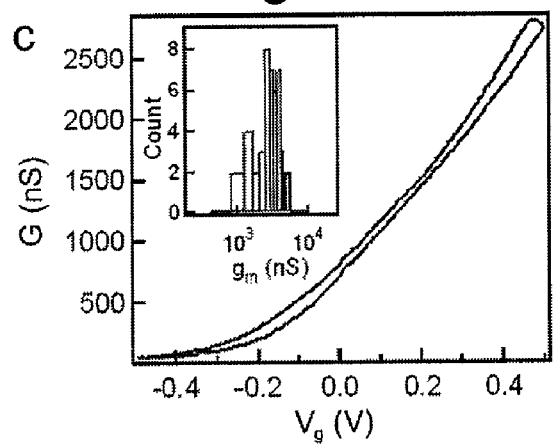

33. The individual SiNW devices were characterized in aqueous buffer solution (10 micromolar phosphate buffer, containing 2 micromolar KCl, pH 7.4) by measuring the conductance, G ($=dI_{ds}/dV_{ds}$) as a function of the water gate potential, $V_g$. G is measured in these and sensor experiments using a lock-in technique (FIG. 28), where $V_{gs}$ was modulated at 79 Hz with a 30 mV amplitude and $V_{ds}(dc)=0$ V, and the water gate electrode was located centrally within the sensor chip device array. Data representative of suitable p-type and n-type SiNW devices are shown in FIGS. 28B and 28C, respectively, which show electrical properties of SiNW FETs in aqueous solution. FIG. 28B shows a typical water-gate transconductance of a p-type SiNW. The inset shows a histogram of transconductance values of more than 50 p-type SiNW devices. FIG. 28C shows a typical water-gate transconductance of an n-type SiNW, with the inset showing a histogram of transconductance values of more than 50 n-type SiNW devices.

Figure 26C:
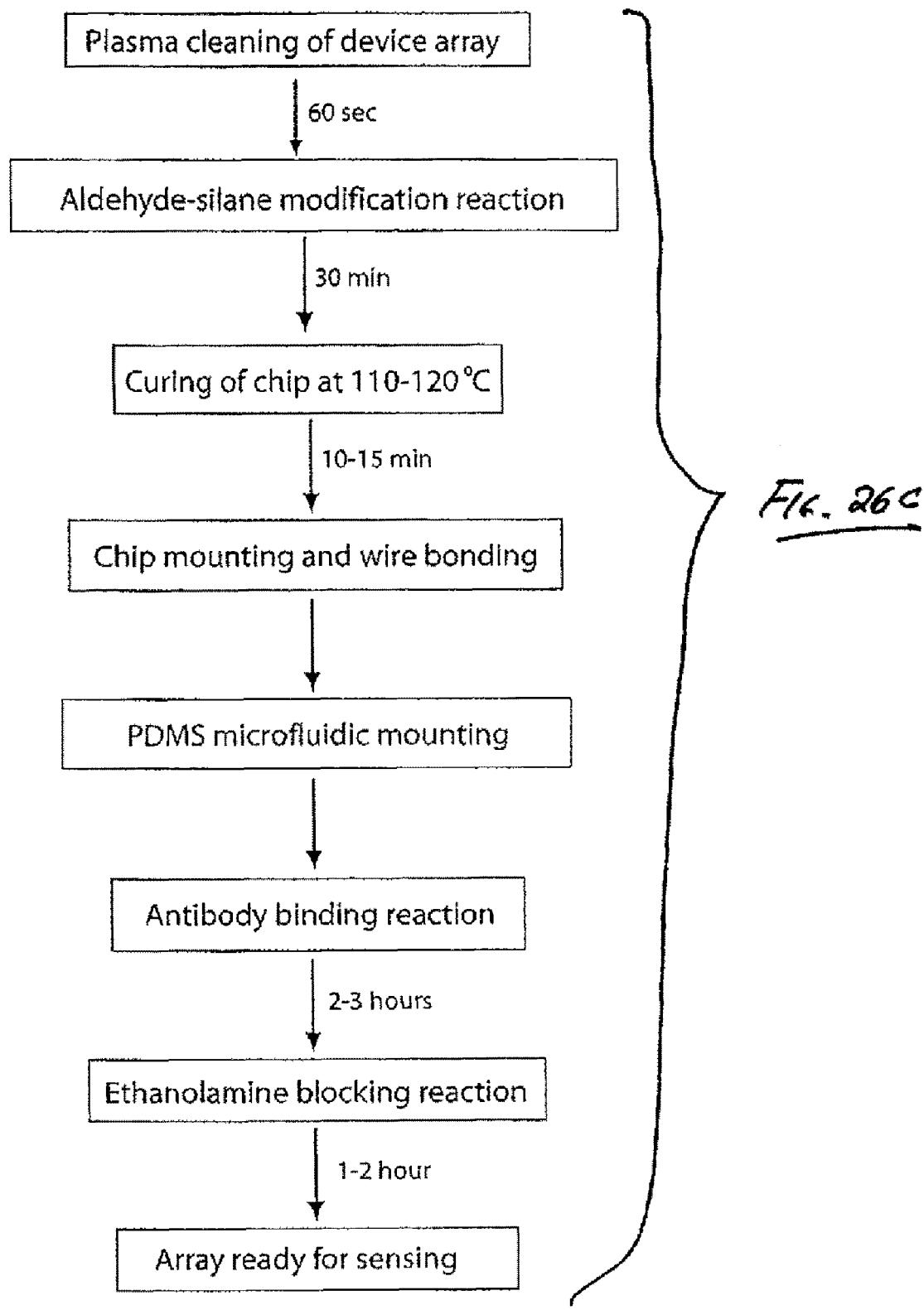
Figure 29:
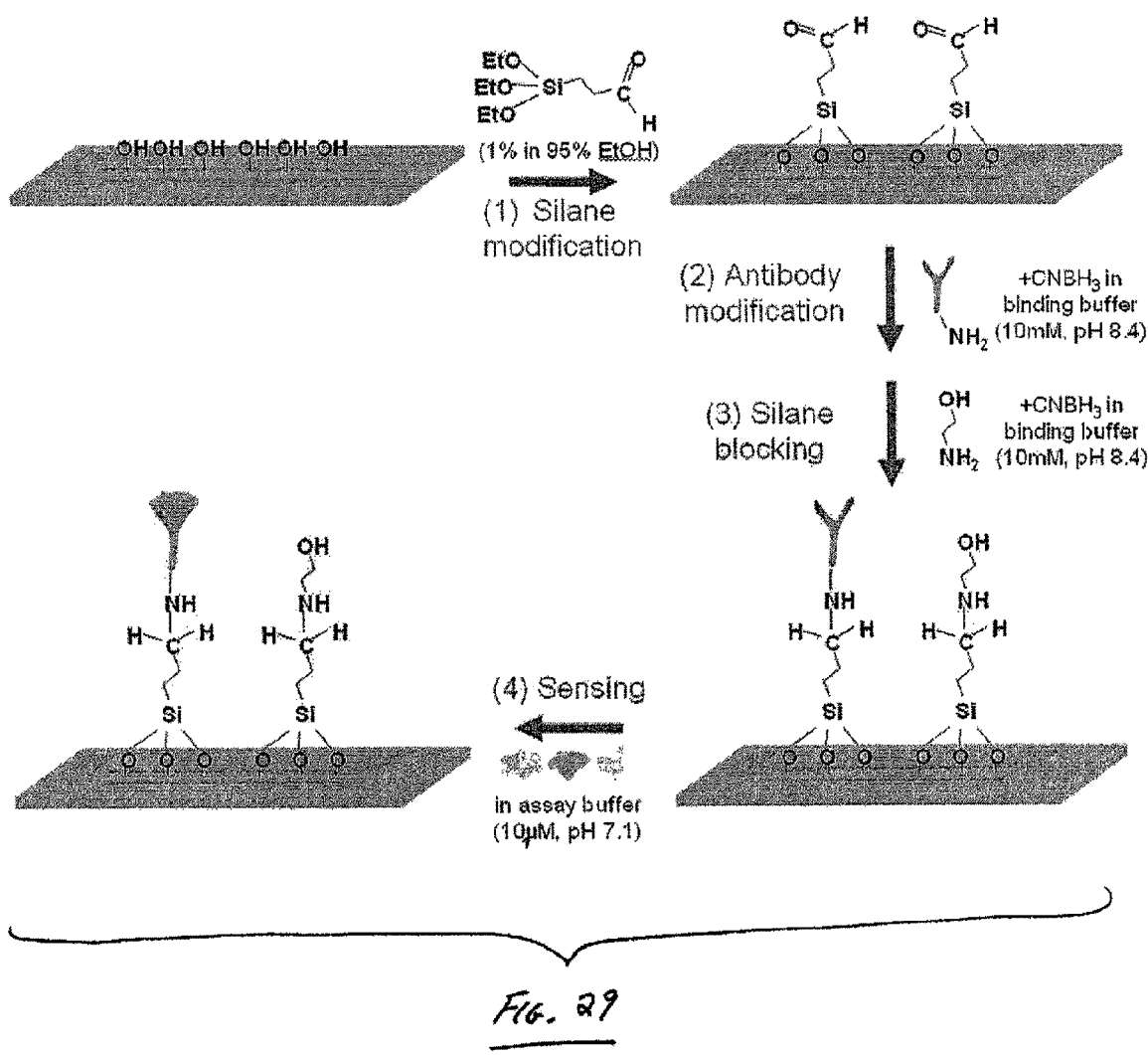
FIG. 29 is a schematic diagram indicating antibody modification of a nanowire, in one embodiment of the invention.

The overall steps involved in linking receptors for specific recognition and selective sensing to the SiNW device surfaces are shown in FIGS. 26C and 29. Specific steps for surface modification were as follows.

34. A sensor device chip was cleaned using an oxygen plasma: 30 W and 50 sccm $O_2$ for 60 sec. The plasma cleaned chip was used promptly.

35. The plasma-cleaned sensor chip was immersed in a filtered 1% volume/volume 3-(trimethoxysilyl)propyl aldehyde in ethanol/water (95%/5%) solution for 30 min (FIG. 29). The silane/ethanol solution was prepared and allowed to stand for 20 min before being filtered with a 0.2 micrometer cut-off syringe filter.

36. The sensor chip was washed with ethanol flow for 50 sec, dried in a stream of nitrogen gas, and heated at 110° C. for 10 min. The silanized surfaces were used relatively quickly after preparation, and kept under a dry nitrogen atmosphere until use if stored.

37. The aldehyde-silane-modified SiNW sensor chip was mounted on the chip carrier using double-sided conductive carbon tape, and then wire-bonding was used to connect contact pads of good devices to the 24 output pads of the chip carrier.

38. A single channel microfluidic device was clamped on the chip carrier such that the channel overlapped the central region of the sensor chip, which contained the SiNW devices. The channel (0.5 mm width×0.05 mm height×10 mm length) was made from polydimethylsiloxane (PDMS) using published procedures. The general strategy of covalent linkage of specific receptors to the SiNW device surface involved drawing a solution of receptor into the PDMS channel until the channel was full, allowing the solution to react, and then quenching the reaction. The aldehyde groups can be used to couple proteins (through lysine residues), and other receptors that have free amine groups. As discussed below, monoclonal antibodies were coupled to the SiNW devices and used in sensing experiments.

39. A solution of monoclonal anti-PSA antibody receptor—10-100 microgram/ml antibody in a pH=8.4, 10 mM phosphate buffer solution containing 4 mM sodium cyanoborohydride was drawn into to the PDMS channel and allowed to react for 2-3 h at room temperature.

40. The surface was washed using a continuous flow of 10 mM phosphate buffer (pH=8.4) through the channel for 10 min.

Alternatively, the device arrays for these experiments were made in the same way as described above, except that distinct antibody solutions were spotted on different regions of device array/sensor chip. A 5% v/v glycerol/antibody solution was spotted using a microarrayer (Affymetrix GMS417) with droplet size of about 100 micrometers.

41. Passivate unreacted aldehyde surface groups by drawing a solution of ethanolamine (100 mM ethanolamine in 10 mM phosphate buffer, pH 8.4) in the presence of 4 mM cyanoborohydride into the channel and allow to stand for 1-2 hours.

42. Lastly, the surface was washed using a continuous flow of 10 mM phosphate buffer (pH=8.4) through the channel for 10 min.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or to unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A nanoscale electrical sensor array device, comprising:
a first, n-doped semiconductor nanoscale wire;
a second, p-doped semiconductor nanoscale wire differing in composition from the first nanoscale wire;
a first reaction entity immobilized relative to the first nanoscale wire such that a binding event involving the first reaction entity is detectable by the nanoscale electrical sensor array device, wherein the first reaction entity is an entity that can interact with an analyte to cause a detectable change in an electrical property of the first nanoscale wire; and
a second reaction entity, identical to the first reaction entity, immobilized relative to the second nanoscale wire such that a binding event involving the second reaction entity is detectable by the nanoscale electrical sensor array device independently of detection of a binding event involving the first reaction entity.

2. The nanoscale electrical sensor array device of claim 1, wherein the first reaction entity is able to bind a virus.

3. The nanoscale electrical sensor array device of claim 1, wherein the first reaction entity is an antibody.

4. The nanoscale electrical sensor array device of claim 1, wherein the first reaction entity is a ganglioside.

5. The nanoscale electrical sensor array device of claim 1, wherein the first reaction entity comprises a binding partner of an analyte.

6. The nanoscale electrical sensor array device of claim 1, wherein the first reaction entity is able to bind a nucleic acid.

7. The nanoscale electrical sensor array device of claim 1, wherein the first reaction entity is able to bind a protein.

8. A method of detecting an analyte using a nanoscale wire, the method comprising:
 exposing a first, n-doped semiconductor nanoscale wire and a second, p-doped semiconductor nanoscale wire to a sample suspected of containing an analyte, the first nanoscale wire having immobilized relative thereto a first reaction entity and the second nanoscale wire having immobilized relative thereto a second reaction entity identical to the first reaction entity; and
 determining a first detectable change in an electrical property of the first nanoscale wire in response to a first binding event involving the first reaction entity and a second detectable change in an electrical property of the second nanoscale wire in response to a second binding event involving the second reaction entity, wherein, if the first detectable change and the second detectable change are opposite responses, the sample is determined as containing the analyte.

9. The method of claim 8, wherein, if the first detectable change and the second detectable change are not opposite responses, then the sample is determined as not containing the analyte.

10. The method of claim 8, wherein the first detectable change is conductance and the second detectable change is conductance.

11. The method of claim 8, wherein the analyte is a virus.

12. The method of claim 8, wherein the first reaction entity is an antibody, and the second reaction entity is an antibody.

13. The method of claim 8, wherein the first reaction entity is a specific binding partner of the analyte.

14. The method of claim 8, wherein the first reaction entity is a nucleic acid.

15. The method of claim 8, wherein the first reaction entity is a protein.

\* \* \* \* \*

SEQUENCE LISTING

<160> NUMBER OF SEQ ID NOS: 60

<210> SEQ ID NO 1
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1 ttaggg                                                                      6

<210> SEQ ID NO 2
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2 ttgggg                                                                      6

<210> SEQ ID NO 3
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 ttgggt                                                                      6

<210> SEQ ID NO 4
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 ttttgggg                                                                    8

<210> SEQ ID NO 5
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5 ttagggt                                                                     7

<210> SEQ ID NO 6
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

-continued

```
ttagggc                                                              7

<210> SEQ ID NO 7
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7 tttaggg                                                              7

<210> SEQ ID NO 8
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8 ttttaggg                                                             8

<210> SEQ ID NO 9
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9 ttagg                                                                5

<210> SEQ ID NO 10
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10 ttaggc                                                               6

<210> SEQ ID NO 11
<211> LENGTH: 2
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11 ag                                                                   2

<210> SEQ ID NO 12
<211> LENGTH: 3
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12 agg                                                                  3
```

```
<210> SEQ ID NO 13
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 aggg                                                                      4

<210> SEQ ID NO 14
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14 agggg                                                                     5

<210> SEQ ID NO 15
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15 aggggg                                                                    6

<210> SEQ ID NO 16
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16 agggggg                                                                   7

<210> SEQ ID NO 17
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17 aggggggg                                                                  8

<210> SEQ ID NO 18
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18 agggggggg                                                                 9

<210> SEQ ID NO 19
```

```
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19 ttacg                                                                    5

<210> SEQ ID NO 20
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20 ttacgg                                                                   6

<210> SEQ ID NO 21
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21 ttacggg                                                                  7

<210> SEQ ID NO 22
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22 ttacgggg                                                                 8

<210> SEQ ID NO 23
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23 ttacggggg                                                                9

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ttacgggggg                                                              10

<210> SEQ ID NO 25
<211> LENGTH: 11
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 25
ttacgggggg g                                                          11

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ttacgggggg gg                                                         12

<210> SEQ ID NO 27
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27 ttacag                                                                 6

<210> SEQ ID NO 28
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28 ttacagg                                                                7

<210> SEQ ID NO 29
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29 ttacaggg                                                               8

<210> SEQ ID NO 30
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30 ttacagggg                                                              9

<210> SEQ ID NO 31
<211> LENGTH: 10
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 31
ttacaggggg                                                              10

<210> SEQ ID NO 32
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ttacaggggg g                                                            11

<210> SEQ ID NO 33
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ttacaggggg gg                                                           12

<210> SEQ ID NO 34
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ttacaggggg ggg                                                          13

<210> SEQ ID NO 35
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35 ttaccg                                                                   6

<210> SEQ ID NO 36
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36 ttaccgg                                                                  7

<210> SEQ ID NO 37
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 37 ttaccggg                                                                  8

<210> SEQ ID NO 38
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38 ttaccgggg                                                                 9

<210> SEQ ID NO 39
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ttaccggggg                                                               10

<210> SEQ ID NO 40
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ttaccggggg g                                                             11

<210> SEQ ID NO 41
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttaccggggg gg                                                            12

<210> SEQ ID NO 42
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ttaccggggg ggg                                                           13

<210> SEQ ID NO 43
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
```

```
ttacacg                                                              7

<210> SEQ ID NO 44
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44 ttacacgg                                                             8

<210> SEQ ID NO 45
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45 ttacacggg                                                            9

<210> SEQ ID NO 46
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ttacacgggg                                                          10

<210> SEQ ID NO 47
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ttacacgggg g                                                        11

<210> SEQ ID NO 48
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ttacacgggg gg                                                       12

<210> SEQ ID NO 49
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ttacacgggg ggg                                                      13
```

```
<210> SEQ ID NO 50
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ttacacgggg gggg                                                         14

<210> SEQ ID NO 51
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tgtgggtgtg gtg                                                          13

<210> SEQ ID NO 52
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ggggtctggg tgctg                                                        15

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ggtgtacgga tgtctaactt ctt                                               23

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ggtgtacgga tgtcacgatc att                                               23

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ggtgtaagga tgtcacgatc att                                               23
```

```
<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ggtgtacgga tgcagactcg ctt                                              23

<210> SEQ ID NO 57
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57 ggtgtac                                                                 7

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ggtgtacgga tttgattagt tatgt                                            25

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ggtgtacgga tttgattagg tatgt                                            25

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60 tttttttaatc cgtcgagcag agtt                                            24
```